(12) United States Patent
Kawakami et al.

(10) Patent No.: US 10,370,438 B2
(45) Date of Patent: Aug. 6, 2019

(54) HISTAMINE-RELEASING FACTOR (HRF), HRF-RECEPTOR AND METHODS OF MODULATING INFLAMMATION

(71) Applicant: LA JOLLA INSTITUTE FOR ALLERGY AND IMMUNOLOGY, La Jolla, CA (US)

(72) Inventors: Toshiaki Kawakami, Del Mar, CA (US); Yuko Kawakami, Del Mar, CA (US)

(73) Assignee: LA JOLLA INSTITUTE FOR ALLERGY AND IMMUNOLOGY, La Jolla, CA (US)

( * ) Notice: Subject to any disclaimer, the term of this patent is extended or adjusted under 35 U.S.C. 154(b) by 0 days.

(21) Appl. No.: 14/462,424

(22) Filed: Aug. 18, 2014

(65) Prior Publication Data
US 2015/0037330 A1 Feb. 5, 2015

Related U.S. Application Data

(63) Continuation of application No. 13/631,560, filed on Sep. 28, 2012, now abandoned, which is a continuation of application No. PCT/US2011/030809, filed on Mar. 31, 2011.

(60) Provisional application No. 61/326,079, filed on Apr. 20, 2010, provisional application No. 61/319,652, filed on Mar. 31, 2010.

(51) Int. Cl.
| | |
|---|---|
| C07K 7/08 | (2006.01) |
| C07K 14/47 | (2006.01) |
| C07K 14/52 | (2006.01) |
| C07K 16/18 | (2006.01) |
| A61K 38/17 | (2006.01) |
| A61K 39/00 | (2006.01) |
| A61K 39/395 | (2006.01) |

(52) U.S. Cl.
CPC .......... *C07K 16/18* (2013.01); *A61K 38/1709* (2013.01); *A61K 39/3955* (2013.01); *C07K 7/08* (2013.01); *C07K 14/47* (2013.01); *C07K 14/52* (2013.01); *A61K 2039/505* (2013.01); *C07K 2317/24* (2013.01); *C07K 2317/76* (2013.01); *C07K 2319/00* (2013.01); *G01N 2500/02* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 2003/0092616 A1* | 5/2003 | Matsuda ............ | C07K 14/4705 435/6.17 |
| 2006/0140970 A1 | 6/2006 | Telerman et al. | |
| 2006/0165677 A1* | 7/2006 | Lee .................... | C07K 14/52 424/131.1 |
| 2007/0184485 A1 | 8/2007 | Kosugi et al. | |

FOREIGN PATENT DOCUMENTS

WO 1997/46884 12/1997

OTHER PUBLICATIONS

Denardo et al., Inflammation and Breast Cancer. Balancing Immune Response: Crosstalk Between Adaptive and Innage Immune Cells During Breast Cancer Progression, Breast Cancer Research, 2007, 9:212.
Kashiwakura et al., Histamine-Releasing Factor Has a Proinflammatory Role in Mouse Models of Asthma and Allergy, J. Clin. Invest. 2012, 122(1):218-228.
Sampson et al., Spontaneous release of histamine from basophils and histamine-releasing factor in patients with atopic dermatitis and food hypersensitivity, New Engl. J. Med., 1989, 321(4):228-232.
Vonakis et al., Distinct characteristics of signal transduction events by histamine-releasing factor/translationally controlled tumor protein (HRF/TCTP)-induced priming and activation of human basophils, Blood, 2008, 111(4):1789-1796, abstract.
Zhou et al., Administration of recombinant P-selection glycoprotein ligand Fc fusion protein suppresses inflammation and neointimal formation in Zucker diabetic rat mode, Arterioscler. Thromb. Vasc. Biol., 2002, 22(10):1598-1603, abstract.
International Application No. PCT/US11/30809, International Search Report dated Oct. 7, 2011.
Kashiwakura, J-I, et al., Histamine-releasing factor has a proinflammatory role in mouse models of asthma and allergy, The Journal of Clinical Investigation, 2012, 122(1):218-228; Supplementary Information: Proinflammatory role of histamine-releasing factor in mouse models of asthma and allergy, pp. 1-21.

* cited by examiner

Primary Examiner — Nora M Rooney
(74) Attorney, Agent, or Firm — Pillsbury Winthrop Shaw Pittmann LLP

(57) ABSTRACT

Methods of treating a food allergy, allergic reactions, hypersensitivity, inflammatory responses, inflammation are provided. In one method, histamine releasing factor (HRF)/translationally controlled tumor protein (TCTP) is contacted with a compound that inhibits or reduces binding of HRF/TCTP to an immunoglobulin in order to treat the food allergy, allergic reaction, hypersensitivity, inflammatory response, or inflammation. Methods of reducing or decreasing the probability, severity, frequency, duration or preventing a subject from having an acute or chronic food allergy, allergic reaction, hypersensitivity, an inflammatory response or inflammation, are also provided. In one method, histamine releasing factor (HRF)/translationally controlled tumor protein (TCTP) is contacted with a compound that inhibits or reduces binding of HRF/TCTP to an immunoglobulin in order to reduce or decrease the probability, severity, frequency, duration or prevent a subject from having an acute or chronic food allergy, allergic reaction, hypersensitivity, an inflammatory response or inflammation.

10 Claims, 22 Drawing Sheets
Specification includes a Sequence Listing.

Figure 11-Cont
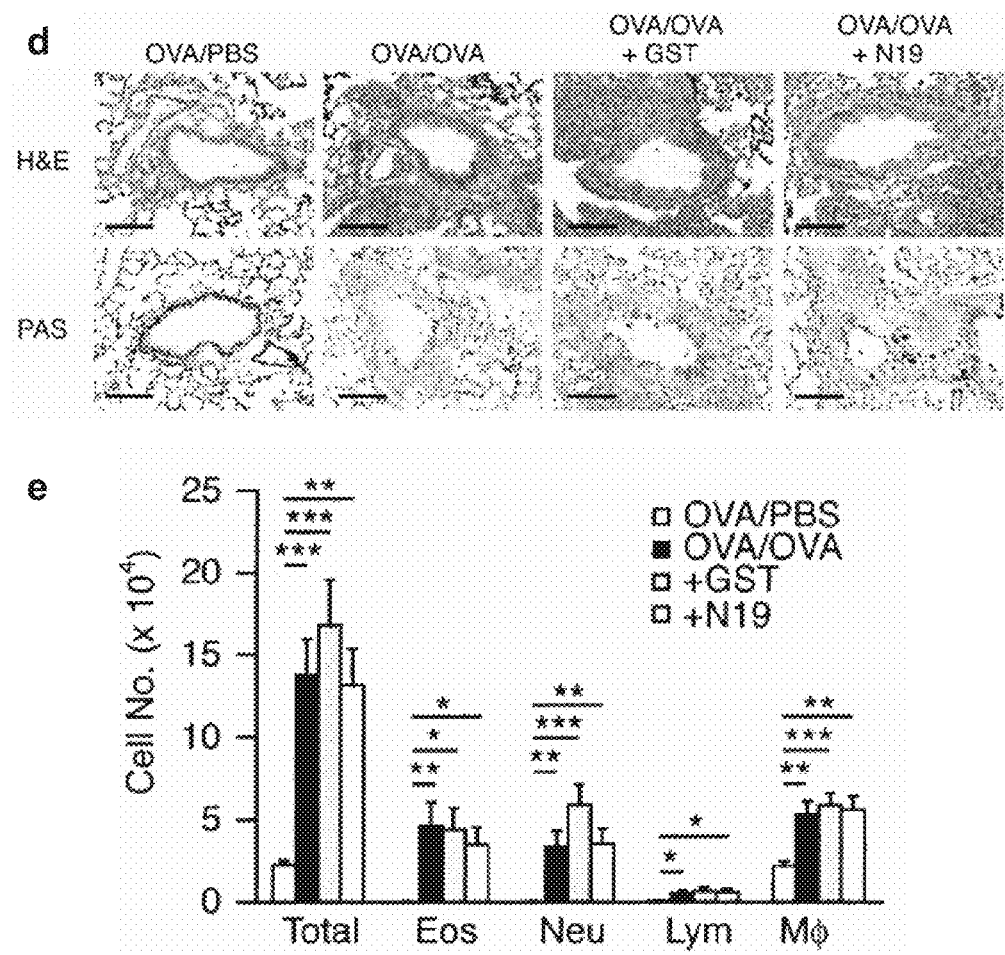

Figure 21

SEQUENCE LISTING

```
<160> NUMBER OF SEQ ID NOS: 24

<210> SEQ ID NO 1
<211> LENGTH: 19
<212> TYPE: PRT
<213> ORGANISM: Homo sapiens
```

```
<400> SEQUENCE: 1

Met Ile Ile Tyr Arg Asp Leu Ile Ser His Asp Glu Met Phe Ser Asp
1               5                   10                  15

Ile Tyr Lys

<210> SEQ ID NO 2
<211> LENGTH: 64
<212> TYPE: PRT
<213> ORGANISM: Homo sapiens

<400> SEQUENCE: 2

Gln Glu Thr Ser Phe Thr Lys Glu Ala Tyr Lys Lys Tyr Ile Lys Asp
1               5                   10                  15

Tyr Met Lys Ser Ile Lys Gly Lys Leu Glu Glu Gln Arg Pro Glu Arg
                20                  25                  30

Val Lys Pro Phe Met Thr Gly Ala Ala Glu Gln Ile Lys His Ile Leu
            35                  40                  45

Ala Asn Phe Lys Asn Tyr Gln Phe Phe Ile Gly Glu Asn Met Asn Pro
        50                  55                  60

<210> SEQ ID NO 3
<211> LENGTH: 172
<212> TYPE: PRT
<213> ORGANISM: Homo sapiens

<400> SEQUENCE: 3

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Met Val Ser Arg Thr Glu Gly Asn Ile Asp Asp Ser Leu Ile
            35                  40                  45

Gly Gly Asn Ala Ser Ala Glu Gly Pro Glu Gly Glu Gly Thr Glu Ser
        50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 4
<211> LENGTH: 172
<212> TYPE: PRT
<213> ORGANISM: Homo sapiens

<400> SEQUENCE: 4

Met Ile Ile Tyr Arg Asp Leu Ile Ser His Asp Glu Met Phe Ser Asp
1               5                   10                  15
```

```
Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 5
<211> LENGTH: 172
<212> TYPE: PRT
<213> ORGANISM: Mus musculus

<400> SEQUENCE: 5

Met Ile Ile Tyr Arg Asp Leu Ile Ser His Asp Glu Leu Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Ala Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Val Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Leu Lys Gly Lys Leu Glu Glu Gln Lys Pro Glu Arg Val Lys
            100                 105                 110

Pro Phe Met Thr Gly Ala Ala Glu Gln Ile Lys His Ile Leu Ala Asn
        115                 120                 125

Phe Asn Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Phe Met
145                 150                 155                 160

Ile Phe Phe Lys Asp Gly Leu Glu Met Glu Lys Cys
                165                 170

<210> SEQ ID NO 6
<211> LENGTH: 172
<212> TYPE: PRT
<213> ORGANISM: Rattus Norvegious

<400> SEQUENCE: 6
```

```
Met Ile Ile Tyr Arg Asp Leu Ile Ser His Asp Glu Leu Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Ala Ile Asp Asp Ser Leu Ile
            35                  40                  45

Gly Gly Asn Ala Ser Ala Glu Gly Pro Glu Gly Gly Thr Glu Ser
        50                  55                  60

Thr Val Val Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Leu Lys Gly Lys Leu Glu Glu Gln Lys Pro Glu Arg Val Lys
            100                 105                 110

Pro Phe Met Thr Gly Ala Ala Glu Gln Ile Lys His Ile Leu Ala Asn
            115                 120                 125

Phe Asn Asn Tyr Gln Phe Phe Ile Gly Glu Asn Met Asn Pro Asp Gly
        130                 135                 140

Met Val Ala Leu Leu Asp Tyr Arg Glu Asp Gly Val Thr Pro Phe Met
145                 150                 155                 160

Ile Phe Phe Lys Asp Gly Leu Glu Met Glu Lys Cys
                165                 170
```

<210> SEQ ID NO 7
<211> LENGTH: 172
<212> TYPE: PRT
<213> ORGANISM: Leporidae

<400> SEQUENCE: 7

```
Met Ile Ile Tyr Arg Asp Leu Ile Ser His Asp Glu Met Phe Ser Asp
1               5                   10                  15

Ile Tyr Lys Ile Arg Glu Ile Ala Gly Gly Leu Cys Leu Glu Val Glu
            20                  25                  30

Gly Lys Met Val Ser Arg Thr Glu Gly Asn Ile Asp Asp Ser Leu Ile
            35                  40                  45

Gly Gly Asn Ala Ser Ala Glu Gly Pro Glu Gly Gly Thr Glu Ser
        50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
            115                 120                 125

Phe Lys Asn Tyr Gln Phe Tyr Ile Gly Glu Asn Met Asn Pro Asp Gly
        130                 135                 140

Met Val Ala Leu Leu Asp Tyr Arg Glu Asp Gly Val Thr Pro Phe Met
145                 150                 155                 160

Ile Phe Phe Lys Asp Gly Leu Glu Met Glu Lys Cys
                165                 170
```

<210> SEQ ID NO 8
<211> LENGTH: 172
<212> TYPE: PRT
<213> ORGANISM: Cavia Porcellus

<400> SEQUENCE: 8

```
Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Ala Asn Met Asn Pro Asp Gly
    130                 135                 140

Met Val Ala Leu Leu Asp Tyr Arg Glu Asp Gly Val Thr Pro Phe Met
145                 150                 155                 160

Ile Phe Phe Lys Asp Gly Leu Glu Met Glu Lys Cys
                165                 170
```

<210> SEQ ID NO 9
<211> LENGTH: 172
<212> TYPE: PRT
<213> ORGANISM: Pan Troglodytes

<400> SEQUENCE: 9

```
Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

<210> SEQ ID NO 10

```
<211> LENGTH: 171
<212> TYPE: PRT
<213> ORGANISM: Cercopithecoid

<400> SEQUENCE: 10

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Val Ser Arg Thr Glu Gly Asn Ile Asp Asp Ser Leu Ile Gly
            35                  40                  45

Gly Asn Ala Ser Ala Glu Gly Pro Glu Gly Glu Gly Thr Glu Ser Thr
    50                  55                  60

Val Ile Thr Gly Val Asp Ile Val Met Asn His His Leu Gln Glu Thr
65                  70                  75                  80

Ser Phe Thr Lys Glu Ala Tyr Lys Lys Tyr Ile Lys Asp Tyr Met Lys
                85                  90                  95

Ser Ile Lys Gly Lys Leu Glu Glu Gln Arg Pro Glu Arg Val Lys Pro
            100                 105                 110

Phe Met Thr Gly Ala Ala Glu Gln Ile Lys His Ile Leu Ala Asn Phe
        115                 120                 125

Lys Asn Tyr Gln Phe Phe Ile Gly Glu Asn Met Asn Pro Asp Gly Met
    130                 135                 140

Val Ala Leu Leu Asp Tyr Arg Glu Asp Gly Val Thr Pro Tyr Met Ile
145                 150                 155                 160

Phe Phe Lys Asp Gly Leu Glu Met Glu Lys Cys
                165                 170

<210> SEQ ID NO 11
<211> LENGTH: 172
<212> TYPE: PRT
<213> ORGANISM: Canis Lupus familiaris

<400> SEQUENCE: 11

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
                20                  25                  30

Gly Lys Met Val Ser Arg Thr Glu Gly Asn Ile Asp Asp Ser Leu Ile
            35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

<210> SEQ ID NO 12
<211> LENGTH: 172
<212> TYPE: PRT
<213> ORGANISM: sus Suinae

<400> SEQUENCE: 12

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 13
<211> LENGTH: 172
<212> TYPE: PRT
<213> ORGANISM: Bovine

<400> SEQUENCE: 13

Met Ile Ile Tyr Arg Asp Leu Ile Ser His Asp Glu Met Phe Ser Asp
1               5                   10                  15

Ile Tyr Lys Ile Arg Glu Val Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
            165                 170

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Forward
      primer for GST fusion proteins

<400> SEQUENCE: 14
aaaaggatcc atgatcatct accgggacc                                      29

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Forward
      primer for GST fusion proteins

<400> SEQUENCE: 15
aaaaggatcc caagaaacca gcttcacaaa                                     30

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Reverse
      primer for GST fusion proteins

<400> SEQUENCE: 16
tttgaattct tactcgtcat ggctgat                                        27

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Reverse
      primer for GST fusion proteins

<400> SEQUENCE: 17
aaagaattct tacttgtaga tgtcggagaa ca                                  32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Reverse
      primer for GST fusion proteins

<400> SEQUENCE: 18
aaagaattct tactccacct ccaggcacag cc                                  32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Reverse
      primer for GST fusion proteins

<400> SEQUENCE: 19

```
aaagaattct tagagcgagt catcgatggc ac                              32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Reverse
      primer for GST fusion proteins

<400> SEQUENCE: 20
aaagaattct tataagtgat ggttcatgac aa                              32

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Reverse
      primer for GST fusion proteins

<400> SEQUENCE: 21
aaagaattct tatggattca tgttttcacc aa                              32

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Reverse
      primer for GST fusion proteins

<400> SEQUENCE: 22
aaaaggatcc caagaaacca gcttcacaaa                                 30

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Forward
      primer for His6-tagged mouse HRF

<400> SEQUENCE: 23
aaaacatatg atcatctacc gggacct                                    27

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Reverse
      primer for His6-tagged mouse HRF

<400> SEQUENCE: 24
ttttctcgag acatttctcc atctctaagc                                 30
```

HISTAMINE-RELEASING FACTOR (HRF), HRF-RECEPTOR AND METHODS OF MODULATING INFLAMMATION

RELATED APPLICATIONS

This application is a continuation application of application Ser. No. 13/631,560, filed Sep. 28, 2012, which is a continuation of International Application No. PCT/US2011/030809, filed Mar. 31, 2011, which claims the benefit of priority to provisional application No. 61/319,652, filed Mar. 31, 2010 and provisional application No. 61/326,079, filed Apr. 20, 2010, all of which applications are expressly incorporated herein by reference in their entirety.

GOVERNMENT SUPPORT

This work was supported in part by Grant AI050209 from the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 18, 2014, is named LIAI0433629_ST25.txt and is 21,069 bytes in size.

INTRODUCTION

Histamine-releasing factor (HRF, also known as translationally controlled tumor protein (TCTP), p21, p23, Q23, and fortilin), is a highly conserved, multifunctional protein with both intracellular and extracellular functions.

HRF exhibits amino acid sequence identities of over 40% between distantly related species (Bommer et al., Int. J. Biochem. Cell Biol. 36:379 (2004); Hinojosa-Moya et al., J. Mol. Evol. 66:472 (2008)). Fifteen of approximately 170 residues are completely or nearly completely conserved in TCTP proteins from yeast, pea, nematode, fruit fly, and mouse (Bommer et al., Int. J. Biochem. Cell Biol. 36:379 (2004)). These invariant residues are largely clustered on one side of the β-stranded 'core' domain. The fold of this domain is similar to that of the Mss4/Dss4 family of proteins, which bind to the GDP/GTP free form of Rab proteins (members of the Ras superfamily) (Thaw et al., Nat. Struct. Biol. 8:701 (2001)). A flexible loop (TCTP1) and the C-terminal loop (TCTP2) following the α-helices comprise the TCTP signatures. The tubulin-binding region and the Ca2+-binding area were mapped to the helical domain. A structural similarity was identified between the H2-H3 helices of TCTP and the H5-H6 helices of Bax, the part of the molecule implicated in the regulation of mitochondrial membrane permeability during apoptosis (Susini et al., Cell Death Differ. 15:1211 (2008)).

As an intracellular protein, TCTP is involved in cell cycle progression, proliferation, survival, and malignant transformation of various cell types (Bommer et al., Int. J. Biochem. Cell Biol. 36:379 (2004)). The name "translationally controlled tumor protein" was given to this protein, because TCTP mRNA levels were high but the protein was not detected in Ehrlich acites tumor cells (Chitpatima et al., Nucleic Acids Res. 16:2350 (1998); Yenofsky et al., Mol. Cell. Biol. 3:1197 (1983)). TCTP is ubiquitously expressed in all tested eukaryotic cells; its expression is active in mitotically active tissues (Thiele et al., Eur. J. Biochem. 267:5473 (2000); Guillaume et al., Proteomics 1:880 (2001)) and subject to both transcriptional and translational control (Bommer et al., RNA 8:478 (2002)). It is involved in the elongation step of protein synthesis by interacting with both eEF1A (a small GTPase) and eEF1Bβ (a guanine nucleotide exchange factor) (Cans et al., Proc. Natl. Acad. Sci. USA 100:13892 (2003); Fleischer et al., Genes Dev. 20:1294 (2006); Langdon et al., Biochim. Biophys. Acta 3:232 (2004)). TCTP inhibits the latter activity, thus slowing down the elongation process, avoiding 'skipping', and resulting in more efficient elongation. G protein binding via the 'core' domain seems to be well conserved among most of TCTPs in various species. Indeed, Drosophila TCTP acts as the guanine nucleotide-exchange factor for Rheb, which regulates the TSC1-TSC2-mTOR pathway (Hsu et al., Nature 445:785 (2007)). Conventional HRF/TCTP KO mice are embryonic lethal (Chen et al., Mol. Biol. Cell 18:2525 (2007)). These Drosophila and mouse studies strongly implicate this protein in the regulation of growth and proliferation as well as in the control of organ size.

Another conserved property of TCTP is its interaction with microtubules and mitochondria (Rinnerthaler et al., Biochim. Biophys. Acta 1757:631 (2006)). TCTP interacts with Mcl-1 (Zhang et al., J. Biol. Chem. 277:37430 (2002); Liu et al., Mol. Cell. Biol. 25:3117-26 (2005)) and Bcl-xL (Yang et al., Oncogene 24:4778 (2005)), anti-apoptotic members of the Bcl-2 family. TCTP antagonizes apoptosis by inserting into the mitochondrial membrane and inhibiting Bax dimerization (Susini et al., Cell Death Differ. 15:1211 (2008)). RNA interference-mediated knockdown of TCTP increases the frequency of tumor reversion apparently consistent with its anti-apoptotic action of the protein (Tuyunder et al., Proc. Natl. Acad. Sci. USA 101:15364 (2004)). By contrast, yeast TCTP displays proapoptotic activity, apparently via an interaction with the outer mitochondrial membrane (Rinnerthaler et al., Biochim. Biophys. Acta 1757:631 (2006)).

HRF can be found in exosomes, suggesting that HRF is secreted through a nonclassical exosome pathway (Amzallag et al., J. Biol. Chem. 279:46104 (2004)). HRF is also a secreted protein and is found in nasal lavages, skin blister fluids, and bronchoalveolar lavage (BAL) fluids during the late phase of allergic reactions (Warner et al., J. Immunol. 136:2583 (1986); MacDonald et al., J. Immunol. 139:506 (1987); MacDonald (1993) in Allergy: Principles and Practice, pp 1-11, "Histamine Releasing Factors and IgE Heterogeneity," Mosby-Year Book Incorporated, St. Louis). HRF secretion is insensitive to brefeldin A or monensin, but can be enhanced by TSAP6, a p53-inducible 5-6 transmembrane protein.

Since human recombinant HRF can stimulate histamine release and cytokine (IL-4 and IL-13) production from IgE-sensitized basophils (MacDonald et al., Science 269:688 (1995); Schroeder et al., J. Exp. Med. 183:1265 (1996); Schroeder et al., J. Immunol. 159:447 (1997)), it is an IgE-dependent cytokine. MacDonald et al. revealed that cell-bound IgE is required for HRF-induced basophil activation and identified functional heterogeneity among human IgE molecules: IgE from HRF-responding (HRF-Responder) basophils derived from ~50% of atopic patients was termed IgE+, and IgE from nonresponders (HRF-Nonresponders) was termed IgE- (MacDonald et al., Int. Arch. Allergy Immunol. 113:187 (1997)).

HRF was also isolated as a B cell growth factor (Kang et al., J. Immunol. 166:6545 (2001)), and can stimulate IL-8 secretion from GM-CSF-primed eosinophils (Bheekha-Escura et al., Blood 96:2191 (2000)). HRF was reported to stimulate bronchial epithelial cells to produce IL-8 and GM-CSF (Yoneda et al., Am. J. Physiol. Lung Cell Mol. Physiol. 286:L174 (2004)). Despite intensive efforts, the exact molecular basis of the IgE+/IgE− dichotomy has remained an enigma. For example, heterogeneity in the carbohydrate portion of IgE molecules fails to distinguish between IgE+ and IgE− (Kleine-Tebbe et al., J. Allergy Clin. Immunol. 98:181 (1996)). On the other hand, the releasability of human basophils in response to anti-IgE was correlated positively with Syk levels (Kepley et al., J. Allergy Clin. Immunol. 104:279 (1999); Lavens-Phillips et al., Am. J. Respir. Cell Mol. Biol. 23:566 (2000); MacGlashan et al., J. Allergy Clin. Immunol. 119:626 (2007)) and negatively with SHIP (SH2 domain-containing phosphatidylinositol 5' phosphatase) levels (MacGlashan et al., J. Allergy Clin. Immunol. 119:626 (2007)). Interestingly, HRF responses in human basophils were shown to negatively correlate with SHIP, but not Syk, levels (Vonakis et al., J Allergy Clin. Immunol. 108:822 (2001)), explaining some HRF-Responder subjects.

HRF-triggered signaling in human basophils was found to be identical or similar to those induced by anti-IgE stimulation of human basophils (Vonakis et al., Blood 111:1789 (2008)) and by antigen stimulation of IgE-sensitized mast cells: 1) stimulation with HRF was not sensitive to pertussis toxin, similar to anti-IgE/IgE-induced basophil activation. 2) Tyrosine phosphorylation of Syk was induced, and a Syk inhibitor blocked HRF-induced histamine release. A recent study also showed loss of Syk protein in human basophils stimulated with HRF similar to that induced by anti-IgE (MacGlashan et al., J. Immunol. 180:4208 (2008)). 3) Increased intracellular Ca2+ and Ca2+/MEK-dependent leukotriene C4 release (MacGlashan and Hubbard, J. Immunol. 151:6358 (1999)) were induced by HRF in HRF-Responder, but not HRF-Nonresponder, basophils. 4) HRF-induced histamine release was inhibited by the phosphatidylinositol 3-kinase (PI3K) inhibitor Ly294002 (Vonakis et al., J. Allergy Clin. Immunol. 108:822 (2001)), and phosphorylation of Akt, a PI3K-dependent event, was induced by HRF in HRF-Responder, but not HRF-Nonresponder, basophils. 5) MEK and ERK phosphorylation was induced by HRF in HRF-Responders, but not HRF-Nonresponder, basophils.

Consistent with the similarities in signaling between HRF-receptor and FcεRI, glucocorticoids were shown to inhibit IL-4 production from HRF-stimulated human basophils at the transcriptional level (Schroeder et al., J. Immunol. 158:5448 (1997)). However, differences were also reported in that no phosphorylation of FcεRIγ (=FcRγ) was found in HRF-stimulated basophils (Vonakis et al., Blood 111:1789 (2008)). However, this failure may be due to low levels of phosphorylation and limited cell numbers used. A pharmacological study showed that rottlerin, which inhibits protein kinase C (PKC)-δ and PKC-θ (Coudronniere et al., Proc. Natl. Acad. Sci. USA 97:3394 (2000)), enhances HRF-mediated histamine release without affecting basophil activation by either anti-IgE or antigen, although staurosporine, Bis II, Gö 6976, or pertussis toxin cannot differentiate histamine release induced by anti-IgE or antigen from that induced by HRF (Bheekha-Escura et al., J. Allergy Clin. Immunol. 103:937 (1999)).

Most studies on HRF have been performed with human basophils. However, the role of HRF, if any, in allergic and other immune diseases has been elusive for decades. For example, a clinical study failed to find a correlation between bronchial late-phase responses to *Dermatophagoides pteronyssinus* (a house dust mite) and IgE reactivity to HRF produced from PBMCs (Budde et al., Ann. Allergy Asthma Immunol. 89:606 (2002)).

The lack of understanding of HRF in allergic and other immune diseases may derive from factors such as that the HRF receptor has not been identified, functional validation with animal models of allergic disease has not verified HRF in allergic and other immune diseases, or has an analysis of the HRF gene been performed on a large population of allergic patients. In addition to these, the study of HRF has another formidable obstacle: how can the extracellular (=cytokine) and intracellular functions of HRF be distinguished? Simple overexpression (by transgenic approach), knockout, or knockdown of the HRF gene cannot resolve this problem. Even conditional knockout techniques will not provide an answer, as the intracellular function of HRF/TCTP in the targeted cells might be affected at the same time. Little is known about how HRF, which does not have a signal sequence, is secreted.

As disclosed herein, one way in which to determine whether HRF has a role, if any, in allergic and other immune diseases, is by potentiation of HRF function or activity, and the other could be inhibition of HRF function or activity. As disclosed herein, identification of an HRF receptor (HRF-R) and a representative inhibitor of HRF/HRF-R (R=receptor) interaction has been identified, and is a representative modulator of HRF's cytokine function, and has revealed the role of HRF in allergic and other immune diseases.

The prevalence of asthma and other allergic diseases has increased dramatically for the last few decades and has reached epidemic proportions in the western populations (Eder, W. et al., N Engl. J. Med. 355:2226 (2006)). Allergic patients suffer from organ-specific manifestations, while the same pathogenic mechanism appears to underlie these diseases. For example, asthma is characterised by lung inflammation, airway hyper-responsiveness (AHR), airway remodeling, and reversible bronchoconstriction; food allergy is manifested by various gastrointestinal, pulmonary and cutaneous signs and symptoms. After binding of allergen-specific IgE to mast cells, susceptible individuals respond to allergens by releasing mast cell-derived mediators. Subsequent allergen exposure produces a cascade of events orchestrated by immune effector cells such as T-helper type 2 (Th2) cells, eosinophils, and mast cells (Gould, H. J. et al. Nat. Rev. Immunol. 8:205 (2008)). Indeed, the pathogenic role of Th2 cytokines such as IL-4, IL-5, IL-9, and IL-13 in various aspects of asthma has been shown in mouse and human studies (Boyce, J. A. et al. J. Exp. Med. 201:1869 (2005)). IgE, produced by B cells stimulated by IL-4 or IL-13, (Geha, R. S., et al. Nat. Rev. Immunol. 3:721 (2003)) also plays a significant role in asthma, as anti-IgE therapy is efficacious in treating asthmatics (Barnes, P. J. Int. Arch. Allergy Immunol. 123:196 (2000)). Further, the high-affinity receptor (FcERI) of IgE and mast cells play a significant role in some asthma models (Kobayashi, T. et al. J. Immunol. 164:3855 (2000); Williams, C. M. et al. J. Exp. Med. 192:455 (2000); Taube, C. et al. J. Immunol. 172:6398 (2004)).

Food allergies typically affect ~6% of young children and 3-4% of adults (Sampson et al., J. Allergy Clin. Immunol. 113:805 (2004); Sicherer et al., J. Allergy Clin. Immunol. 114:159 (2004)). In the US, food allergy alone accounts for about 30,000 anaphylactic reactions, 2,000 hospital admissions, and 200 deaths each year (Yocum et al., J. Allergy Clin. Immunol. 104:452 (1999); Burks, Lancet 371:1538 (2008)). Peanuts, tree nuts, fish, and shellfish are common allergens in both children and adults, while children also often react to eggs, wheat, and soy.

Food-induced allergic reactions result from immunologic pathways that include activation of effector cells through food specific IgE antibodies, cell-mediated (non-IgE-mediated) reactions resulting in subacute or chronic inflammation, or the combination of these pathways. The significance of IgE-mediated arm of reactions in human was demonstrated by anti-IgE therapy in patients with peanut allergy, which significantly and substantially increased the threshold of sensitivity to peanut on oral food challenge (Leung et al., N. Engl. J. Med. 348:986 (2003)). Furthermore, histamine has been reported to increase in food allergy patients after allergen challenge (Sampson and Jolie, N. Engl. J. Med. 311:372 (1984)), suggesting the involvement of mast cell or basophil activation downstream of IgE-mediated pathways. On the other hand, celiac disease, which is a representative of the cell-mediated arm of food hypersensitivity, is mediated by gluten-reactive T cells, and the symptoms are confined to gut, often mild and chronic (Sollid and Lundin, Mucosal Immunol. 2:3 (2009)).

Systemic anaphylaxis mouse models revealed two major pathways (Finkelman, J. Allergy Clin. Immunol. 120:506 (2007)), both of which depend on immunoglobulins (Igs). The signals of the classic pathway start from IgE and its high-affinity receptor, FcεRI, on mast cells, and the subsequent release of histamine and platelet activating factor (PAF) causes the anaphylactic symptoms. Indeed, blockade of histamine can prevent the hypothermia triggered by this pathway of anaphylaxis (Makabe-Kobayashi et al., J. Allergy Clin. Immunol. 110:298 (2002)). The alternative pathway depends upon IgG/FcγRIII signaling on macrophages or basophils, which leads to PAF release (Strait et al., J. Allergy Clin. Immunol. 109:658 (2002)). Small doses of antigen favor the classic pathway, while the large doses are required for the alternative pathway (Strait et al., J. Clin. Invest. 116:833 (2006)). Since only a small proportion of orally administered antigen participates in the systemic circulation in an immunologically intact form (Warshaw et al., Lab Invest. 25:675 (1971)), the contribution of the alternative pathway towards food allergy should be interpreted with caution (Berin and Mayer, Mucosal Immunol. 2:24 (2009)). In a cholera toxin-induced model of peanut allergy (Li et al., J. Allergy Clin. Immunol. 106:150 (2000)) in C57BL/6 background mice (Sun et al., J. Immunol. 179:6696 (2007)), anaphylaxis was completely abolished in B-cell-deficient or mast cell-deficient mice, whereas FcεRIα-deficient mice showed significantly milder anaphylactic responses (Sun et al., J. Immunol. 179:6696 (2007)).

There are also two major food-induced diarrhea models, in at least one of which the Ig/mast cell axis was shown to play a role. In that model, mice were sensitized with OVA plus alum injected intraperitoneally, and fed with OVA (Brandt et al., J. Clin. Invest. 112:1666 (2003)). This model has increased mast cells in the small intestine, especially in jejunum. Mast cell depletion by anti-c-Kit antibody abrogated the diarrhea, while FcεRIα knockout mice showed delayed and decreased incidence of diarrhea development (Brandt et al., J. Clin. Invest. 112:1666 (2003)). Adoptive transfer of mesenteric lymph node CD4$^+$ T cells could transfer the sensitization to naïve mice. However, several challenges of OVA were needed for mast cell accumulation and diarrhea development after transfer (Knight et al., Am. J. Physiol. Gastrointest. Liver Physiol. 293:G1234 (2007)). IL-9 was shown to be important for mast cell accumulation and diarrhea development (Forbes et al., J. Exp. Med. 205:897 (2008)). The other model uses OVA plus CFA injected subcutaneously, and fed with OVA (Kweon et al., J. Clin. Invest. 106:199 (2000)). In this model, the increase of mast cells was observed in colon, not in the small intestine. IL-4 and Stat6 were shown to be indispensable for diarrhea occurrence (Kweon et al., J. Clin. Invest. 106:199 (2000)). When signaling of sphingosine 1-phosphate was blocked by FTY 720, the recruitment of mast cells and Th2 cells were inhibited, and diarrhea was abolished without affecting increased IgE level (Kurashima et al., J. Immunol. 179:1577 (2007)).

Mononuclear cells from food allergy patients have been reported to secrete HRF, and the spontaneous ex vivo histamine release from basophils were reportedly increased in those patients (May, J. Allergy Clin. Immunol. 58:432 (1976); May and Remigio, Clin. Allergy 12:299 (1982); Sampson et al., N. Engl. J. Med. 321:228 (1989)). This spontaneous histamine release decreased after elimination of allergenic food, and patients who adhered to a restricted diet had an apparently declined rate of spontaneous generation of HRF in mononuclear cells (Sampson et al., N. Engl. J. Med. 321:228 (1989)). However, these studies were based on histamine releasing activity of serum on basophils, not on direct measurement of HRF. In addition, the impact of spontaneous release of histamine from basophils on food allergy pathogenesis has not been studied. Thus, the role of HRF in food allergy remains unclear.

New manifestations of food allergy are also increasing in recognition and prevalence. The most common of these is eosinophilic esophagitis (EoE) (Furuta et al., Gastroenterology 133:1342 (2007)). Symptoms of EoE include vomiting, abdominal pain, and failure to thrive in young children which progress to predominant complaints of dysphagia in adolescents and adults (Furuta et al., Gastroenterology 133: 1342 (2007)). Clinically, EoE is difficult to distinguish from other forms of esophagitis, specifically gastroesophageal reflux disease (GERD) (Furuta et al., Gastroenterology 133:1342 (2007)). However, in stark contrast to GERD, EoE is successfully treated using empiric or skin prick/skin patch-directed elimination diets and elemental formulas (Kagalwalla et al., Clin. Gasteroenterol. Hepatol. 4:1097 (2006); Spergel et al., Ann. Allergy Asthma Immunol. 95:336 (2005); Spergel et al., J. Allergy Clin. Immunol. 119:509 (2007)). Indeed, elemental formula is one of the most effective therapeutic regimens in EoE with patients demonstrating >96% response rates (Markowitz et al., Am. J. Gastroenterol. 98:777 (2003)). The most significant complication of EoE is esophageal stricture formation due to tissue remodeling (Aceves et al., J. Allergy Clin. Immunol. 119:206 (2007); Fruman et al., Immunity 13:1 (2000)). However, food impactions can occur even in the absence of strictures, likely due to the significant esophageal dysmotility described in both adult and pediatric EoE patients (Furuta et al., Gastroenterology 133:1342 (2007); Korsapati et al., Gut 58:1056 (2009); Nurko et al., Am. J. Gastroenterol. 104:3050 (2009); Remedios et al., Gastrointest. Endosc. 63:3 (2006)).

Although the majority of patients with EoE (approximately 70%) have food sensitization, the role of IgE mediated food allergy in EoE remains relatively unclear (Furuta et al., Gastroenterology 133:1342 (2007)). Recent reports suggest that there is increased local IgE production in addition to the systemic sensitizations that occur in EoE (Vicario et al., Gut 59:12 (2010)). In addition, delayed type hypersensitivity and a dependence on T cells also play a role in EoE (Mishra et al., J. Leukoc. Biol. 81:916 (2007)). Although defined by the presence of a diffuse eosinophilia of the esophagus (>15 eosinophils per high power field despite adequate acid blockade), EoE is accompanied by a significant esophageal mastocytosis (Kirsh et al., *J. Pediatric Gastroenterol. Nutrition* 44:20 (2007)). Mast cells tend to be degranulated in EoE patients (Kirsh et al., *J. Pediatric Gastroenterol. Nutrition* 44:20 (2007)). As such, the previously unstudied role of mast cell activating factors such as HRF in EoE patients is important and may lend new therapeutic options in these patients.

Thus, there is a need for compounds and methods of treating immune diseases and allergic reactions, such as food allergies, airway inflammation, and hypersensitivity. This invention addresses this need and provides related benefits.

SUMMARY

The invention provides methods of treating a food allergy. In one embodiment, a method includes contacting histamine releasing factor (HRF)/translationally controlled tumor protein (TCTP) with a compound that inhibits or reduces binding of HRF/TCTP to an immunoglobulin thereby treating a food allergy.

The invention also provides methods of treating an allergic reaction, hypersensitivity, an inflammatory response or inflammation. In one embodiment, a method includes contacting histamine releasing factor (HRF)/translationally controlled tumor protein (TCTP) with a compound that inhibits or reduces binding of HRF/TCTP to an immunoglobulin thereby treating the allergic reaction, hypersensitivity, inflammatory response or inflammation.

The invention further provides methods of reducing or decreasing the probability, severity, frequency, duration or preventing a subject from having an acute or chronic food allergy, allergic reaction, hypersensitivity, an inflammatory response or inflammation. In one embodiment, a method includes administering to a subject a compound that inhibits or reduces binding of HRF/TCTP to an immunoglobulin thereby decreasing the probability, severity, frequency, duration or preventing the subject from having an acute or chronic food allergy, allergic reaction, hypersensitivity, inflammatory response or inflammation.

Compounds include peptides and polypeptides. Non-limiting exemplary peptides and polypeptides include antibody and antibody subsequences (polyclonal and monoclonal). Antibodies include mammalian antibodies, such as human and humanized antibodies and subsequences. Additional non-limiting exemplary peptides and polypeptides include an HRF/TCTP (e.g., mammalian) polypeptide, or a subsequence or fragment of an HRF/TCTP (e.g., mammalian) polypeptide, that binds to an immunoglobulin. In particular aspects, a subsequence or fragment of HRF/TCTP polypeptide that binds to an immunoglobulin includes or consists of amino acids 1-19 or amino acids 79-142 of a HRH/TCTP sequence (e.g., mammalian), or a subsequence thereof. In additional particular aspects, a subsequence or fragment of HRF/TCTP polypeptide that binds to an immunoglobulin includes or consists of MIIYRDLISHDEMFSDIYK (SEQ ID NO:1), or QETSFTKEAYKKYIKDYMKSIKGKLEEQRPERVKPFMTGAAEQIKHILANFKNYQ FFIGENMNP (SEQ ID NO:2) sequence, or a subsequence thereof. Immunoglobulins to which HRH/TCTP sequence bind include, IgG, IgE, IgA, IgM, or IgD.

Methods of the invention are useful for treatment of a food allergy, allergic reaction, hypersensitivity, inflammatory response or inflammation, chronic or acute. Methods of the invention include those sufficient to protect against the food allergy, allergic reaction, hypersensitivity, inflammatory response or inflammation, decrease, reduce, inhibit, suppress, limit or control susceptibility to the food allergy, allergic reaction or hypersensitivity, or decrease, reduce, inhibit, suppress, limit or control the food allergy, allergic reaction, hypersensitivity, inflammatory response or inflammation. Methods of the invention also include those sufficient to decrease, reduce, inhibit, suppress, limit, control or improve the probability, severity, frequency, or duration of one or more adverse symptoms, disorders, illnesses, pathologies, diseases, or complications caused by or associated with the food allergy, allergic reaction, hypersensitivity, inflammatory response or inflammation. Methods of the invention further include those sufficient to reduce or inhibit progression, severity, frequency, duration or probability of an adverse symptom of the food allergy, allergic reaction, hypersensitivity, inflammatory response or inflammation.

Methods of the invention are also useful for treatment of more particular allergic reactions, such as extrinsic or intrinsic bronchial asthma; Allergic rhinitis; Onchocercal dermatitis; Atopic dermatitis; eczema; rash; allergic urticaria (e.g. hives); allergic conjunctivitis; Drug reactions; Nodules, eosinophilia, rheumatism, dermatitis, and swelling (NERDS); Eosophageal and a gastrointestinal allergy. Methods of the invention are also useful for treatment of more types of hypersensitivity, inflammatory response or inflammation, such as a respiratory disease or disorder (e.g., that affects the upper or lower respiratory tract). Non-limiting exemplary respiratory diseases and disorders include asthma, allergic asthma, bronchiolitis, pleuritis, Airway Obstruction, Apnea, Asbestosis, Atelectasis, Berylliosis, Bronchiectasis, Bronchiolitis, Bronchiolitis Obliterans Organizing Pneumonia, Bronchitis, Bronchopulmonary Dysplasia, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Rhinoscleroma, Scimitar Syndrome, Severe Acute Respiratory Syndrome, Silicosis, Tracheal Stenosis, eosinophilic pleural effusions, Histiocytosis; chronic eosinophilic pneumonia; hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease (COPD); Interstitial Lung Disease; allergic rhinoconjunctivitis; allergic conjunctivitis and Topical eosinophilia.

Methods of the invention are further useful for treatment of more particular allergic reactions, hypersensitivity, inflammatory response or inflammation, such as a skin or eye allergic reaction, hypersensitivity, inflammatory response or inflammation.

The invention moreover provides methods of increasing, enhancing or stimulating airway-dilation. In one embodiment, a method includes administering to a subject in need of increasing airway-dilation an amount of a compound that inhibits or reduces binding of HRF/TCTP to an immunoglobulin sufficient to increase, enhance or stimulate airway-dilation in the subject.

The invention additionally provides methods of reducing or inhibiting airway-constriction. In one embodiment, a method includes administering to a subject in need thereof an amount of a compound that inhibits or reduces binding of HRF/TCTP to an immunoglobulin sufficient to reduce or inhibit airway-constriction in the subject.

Compounds may be administered at any time relative to the condition to be treated. In particular embodiments, a compound is administered prior to, substantially contemporaneously with or following one or more adverse symptoms, disorders, illnesses, pathologies, diseases, or complications caused by or associated with the disease or disorder, for example, food allergy, allergic reaction or hypersensitivity. In more particular embodiments, a compound is administered to a subject substantially contemporaneously with, or within about 1-60 minutes, hours, or days of the onset of an adverse symptom associated with the disease or disorder, for example, a food allergy, allergic reaction or hypersensitivity.

Compounds may be administered by any route, locally, regionally or systemically. In particular embodiments, a compound is administered via ingestion, via inhalation, or topically. A compound can be administered one, two, three, four or more times daily, weekly, monthly, bi-monthly, or annually, to a subject.

The amount of compound administered can be in an amount likely sufficient or effective to provide a response to a subject. In particular embodiments, a compound is from about 0.00001 mg/kg to about 10,000 mg/kg, from about 0.0001 mg/kg to about 1000 mg/kg, from about 0.001 mg/kg to about 100 mg/kg, from about 0.01 mg/kg to about 10 mg/kg, or from about 0.1 mg/kg, about 1 mg/kg body weight.

The invention still also provides methods of diagnosing a subject having or at risk of a food allergy. In one embodiment, a method includes measuring histamine releasing factor (HRF)/translationally controlled tumor protein (TCTP) in a sample from a subject, wherein an amount of HRF/TCTP in the sample greater than normal diagnoses the subject as having or at risk of a food allergy. Non-limiting examples of measuring include, for example, determining the amount of HRF/TCTP protein or nucleic acid encoding HRF/TCTP in the sample; contacting the sample with an agent or tag that binds to HRF/TCTP protein or nucleic acid encoding HRF/TCTP and ascertaining the amount of HRF/TCTP protein or nucleic acid encoding HRF/TCTP, or the amount of agent or tag bound to the HRF/TCTP protein or nucleic acid encoding HRF/TCTP.

The invention yet further provides methods of identifying an agent that reduces or inhibits a food allergy, allergic reaction, hypersensitivity, inflammatory response or inflammation. In one embodiment, a method includes contacting histamine releasing factor (HRF)/translationally controlled tumor protein (TCTP) with a test compound in the presence of an immunoglobulin that binds to HRF/TCTP; and determining if the compound inhibits or reduces binding of HRF/TCTP to the immunoglobulin, wherein a reduction or inhibition of binding identifies the test compound as an agent that reduces or inhibits a food allergy, allergic reaction, hypersensitivity, inflammatory response or inflammation.

Subjects include any animal in need of treatment, such as a subject in need of treatment for a food allergy, allergic reaction, hypersensitivity, an inflammatory response or inflammation. In particular embodiments, a subject is a mammal (e.g., a human).

The invention still moreover provides subsequences of mammalian HRF/TCTP sequence less than full length HRF, wherein the subsequence binds to an immunoglobulin. In one embodiment, a subsequence includes or consists of amino acids 1-19 (e.g., MIIYRDLISHDEMFSDIYK (SEQ ID NO:1)) or amino acids 79-142 (e.g., QETSFTKEAYK-KYIKDYMKSIKGKLEEQRPERVKPFMTGAAEQIKHI-LANFKNYQ FFIGENMNP (SEQ ID NO:2)) of a mammalian HRF. In another embodiment, a subsequence includes or consists of a subsequence of a mammalian HRF/TCTP set forth as: MIIYRDLISHDEMFSDIYKIREIADGLCLEV-EGKMVSRTEGNIDDSLIGGNASAE GPEGEGTESTVIT-GVDIVMNHHLQETSFTKEAYKKYIKDYMKSIK-GKLEEQRPER VKPFMTGAAEQIKHILANFKNYQFFIGENMNPDGM-VALLDYREDGVTPYMIFFK DGLEMEKC (SEQ ID NO:3), wherein the subsequence is between about 5-171 amino acid residues in length, and binds to an immunoglobulin. In particular aspects, a subsequence has a length from about 5-10, 10-20, 20-50, 100-150, or 150-171 amino acid residues.

The invention still further provides isolated and purified antibody or antibody subsequence that binds to mammalian HRF/TCTP sequence, which sequence includes or consists of amino acids 1-19 (MIIYRDLISHDEMFSDIYK (SEQ ID NO:1)) or amino acids 79-142 (QETSFTKEAYK-KYIKDYMKSIKGKLEEQRPERVKPFMTGAAEQIKHI-LANFKNY QFFIGENMNP (SEQ ID NO:2)), or binds to a fragment of mammalian HRF/TCTP sequence set forth as MIIYRDLISHDEMFSDIYKIREIADGLCLEVEGKMVS-RTEGNIDDSLIGGNASAEGP EGEGTESTVITGVDIVM-NHHLQETSFTKEAYKKYIKDYMKSIKGKLE-EQRPERVK PFMTGAAEQIKHILANFKNYQFFIGENMNPDGM-VALLDYREDGVTPYMIFFKDG LEMEKC (SEQ ID NO:3), wherein the fragment is 5-171 amino acid residues in length. In particular aspects, a subsequence has a length from about 5-10, 10-20, 20-50, 100-150, or 150-171 amino acid residues.

DESCRIPTION OF THE DRAWINGS

FIG. 21 shows an alignment of representative mammalian HRF sequences (SEQ ID NOs:4-10).

DETAILED DESCRIPTION

Figure 1:
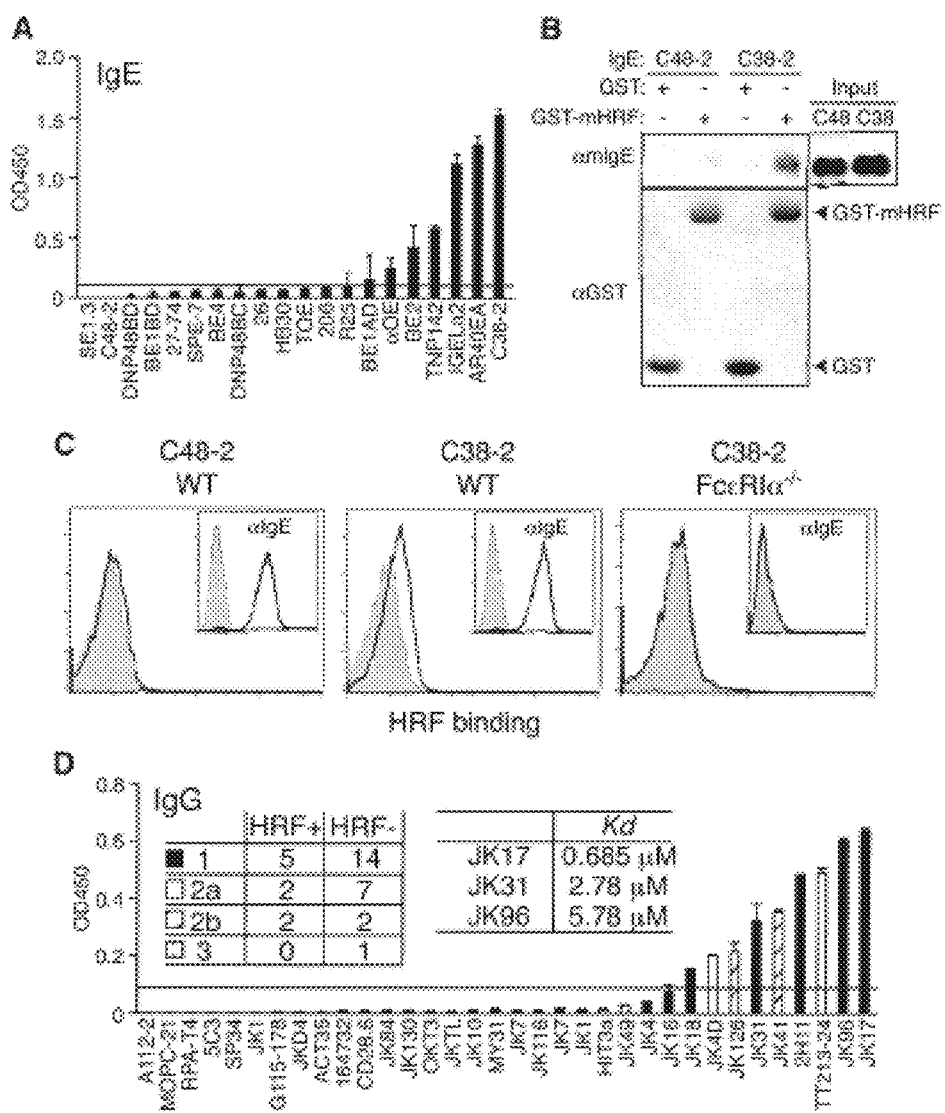
FIGS. 1A-1D show A) HRF-bound mouse IgE by ELISA; B) detection of IgE and GST proteins by immunoblotting with anti-mouse IgE antibody and anti-GST mAb, respectively; C) HRF binding detected by flow cytometry when WT, but not $FcεRIα^{-/-}$, BMMCs were incubated with an HRF-reactive (C38-2), but not a nonreactive (C48-2, left panel), IgE mAb. Insets show IgE binding: BMMCs preincubated with or without (gray) the indicated IgE were incubated with FITC-labeled anti-mouse IgE; and D) the numbers of mAbs classified into IgG subtypes and $K_D$ values of some IgG molecules to HRF are shown as detected by ELISA.

The invention is based, at least in part, on histamine releasing factor (HRF)/translationally controlled tumor protein (TCTP), and the identification of the HRF receptor (HRF-R) and inhibitors of HRF/HRF-R interactions. The invention is also based, at least in part, on identifying the role of HRF in food allergies, airway inflammation and skin or eye hypersensitivity.

In accordance with the invention, polypeptide (e.g., HRF, antibodies) sequences, such as substantially isolated, purified, and recombinant polypeptides, e.g., that bind to an immunoglobulin (Ig), are provided. In one embodiment, a polypeptide sequence is characterized as including or consisting of a subsequence of HRF (e.g., mammalian HRF) which binds to an immunoglobulin. In another embodiment, a polypeptide sequence is characterized as including or consisting of HRF amino acids 1-19 (e.g., MIIYRDLISH-DEMFSDIYK (SEQ ID NO:1)) or HRF amino acids 79-142 (e.g., QETSFTKEAYKKYIKDYMKSIKGKLEEQRPER-VKPFMTGAAEQIKHILANFKNYQ FFIGENMNP (SEQ ID NO:2)), or a subsequence of HRF amino acids 1-19 or HRF amino acids 79-142, and which subsequence binds to an immunoglobulin. In another embodiment, a polypeptide sequence is characterized as including or consisting of a subsequence of mammalian HRF/TCTP HRF amino acids MIIYRDLISHDEMFSDIYKIREIADGLCLEVEGKMVS-RTEGNIDDSLIGGNASAEGP EGEGTESTVITGVDIVM-NHHLQETSFTKEAYKKYIKDYMKSIKGKLE-EQRPERVK PFMTGAAEQIKHILANFKNYQFFIGENMNPDGM-VALLDYREDGVTPYMIFFKDG LEMEKC (SEQ ID NO:3), where the sequence is not full length HRF, and has between about 5-171 HRF amino acid residues in length, and which sequence binds to an immunoglobulin. Non-limiting exemplary sequences less than full length HRF sequence include, for example, 5-10, 10-20, 20-30, 30-40, 40-50, 50-75, 75-100, 100-150, and 150-171 amino acid residues of HRF sequence.

Figure 21:
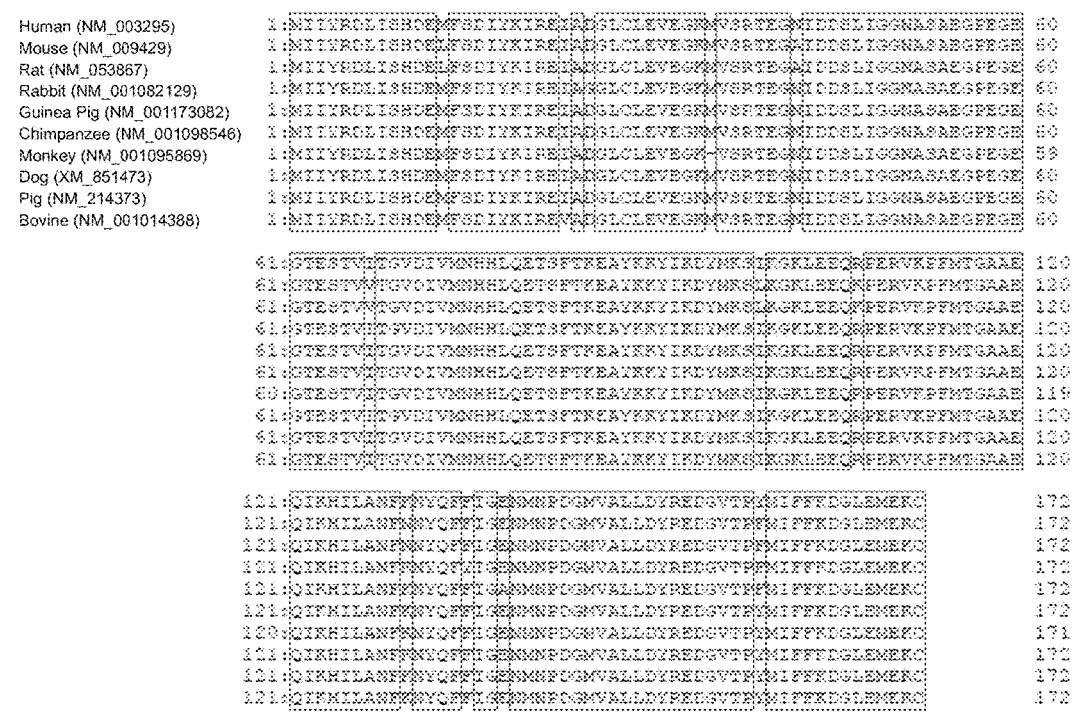

Exemplary mammalian HRF sequences include human and non-human HRF sequences. Exemplary Human (NM_003295), Mouse (NM_009429), Rat (NM_053867), Rabbit (NM_001082129), Guinea Pig (NM_001173082), Chimpanzee (NM_001098546), Monkey (NM_001095869), Dog (NM_851473), Pig (NM_214373), Bovine (NM_001014388), respectively, are set forth, in order, in Table 1 and FIG. 21 (SEQ ID NOs:4-10):

```
  1: MIIYRDLISHDEMFSDIYKIREIADGLCLEVEGKMVSRTEGNIDDSLIGGNASAEGPEGE  60

1: MIIYRDLISHDELFSDIYKIREIADGLCLEVEGKMVSRTEGAIDDSLIGGNASAEGPEGE  60

1: MIIYRDLISHDELFSDIYKIREIADGLCLEVEGKMVSRTEGAIDDSLIGGNASAEGPEGE  60

1: MIIYRDLISHDEMFSDIYKIREIAGGLCLEVEGKMVSRTEGNIDDSLIGGNASAEGPEGE  60

1: MIIYRDLISHDEMFSDIYKIREIADGLCLEVEGKMVSRTEGNIDDSLIGGNASAEGPEGE  60

1: MIIYRDLISHDEMFSDIYKIREIADGLCLEVEGKMVSRTEGNIDDSLIGGNASAEGPEGE  60

1: MIIYRDLISHDEMFSDIYKIREIADGLCLEVEGK-VSRTEGNIDDSLIGGNASAEGPEGE  60

1: MIIYRDLISHDEMFSDIYKIREIADGLCLEVEGKMVSRTEGNIDDSLIGGNASAEGPEGE  60

1: MIIYRDLISHDEMFSDIYKIREIADGLCLEVEGKMVSRTEGNIDDSLIGGNASAEGPEGE  60

1: MIIYRDLISHDEMFSDIYKIREVADGLCLEVEGKMVSRTEGNIDDSLIGGNASAEGPEGE  60

61: GTESTVITGVDIVMNHHLQETSFTKEAYKKYIKDYMKSIKGKLEEQRPERVKPFMTGAAE 120

61: GTESTVVTGVDIVMNHHLQETSFTKEAYKKYIKDYMKSLKGKLEEQKPERVKPFMTGAAE 120

61: GTESTVVTGVDIVMNHHLQETSFTKEAYKKYIKDYMKSLKGKLEEQKPERVKPFMTGAAE 120

61: GTESTVITGVDIVMNHHLQETSFTKEAYKKYIKDYMKSIKGKLEEQRPERVKPFMTGAAE 120

61: GTESTVITGVDIVMNHHLQETSFTKEAYKKYIKDYMKSIKGKLEEQRPERVKPFMTGAAE 120

61: GTESTVITGVDIVMNHHLQETSFTKEAYKKYIKDYMKSIKGKLEEQRPERVKPFMTGAAE 120

61: GTESTVITGVDIVMNHHLQETSFTKEAYKKYIKDYMKSIKGKLEEQRPERVKPFMTGAAE 120

61: GTESTVITGVDIVMNHHLQETSFTKEAYKKYIKDYMKSIKGKLEEQRPERVKPFMTGAAE 120

61: GTESTVITGVDIVMNHHLQETSFTKEAYKKYIKDYMKSIKGKLEEQRPERVKPFMTGAAE 120

61: GTESTVITGVDIVMNHHLQETSFTKEAYKKYIKDYMKSIKGKLEEQRPERVKPFMTGAAE 120

121: QIKHILANFKNYQFFIGENMNPDGMVALLDYREDGVTPYMIFFKDGLEMEKC         172

121: QIKHILANFNNYQFFIGENMNPDGMVALLDYREDGVTPFMIFFKDGLEMEKC         172

121: QIKHILANFNNYQFFIGENMNPDGMVALLDYREDGVTPFMIFFKDGLEMEKC         172

121: QIKHILANFKNYQFYIGENMNPDGMVALLDYREDGVTPFMIFFKDGLEMEKC         172

121: QIKHILANFKNYQFFIGANMNPDGMVALLDYREDGVTPFMIFFKDGLEMEKC         172

121: QIKHILANFKNYQFFIGENMNPDGMVALLDYREDGVTPYMIFFKDGLEMEKC         172

121: QIKHILANFKNYQFFIGENMNPDGMVALLDYREDGVTPYMIFFKDGLEMEKC         172
```

```
121: QIKHILANFKNYQFFIGENMNPDGMVALLDYREDGVTPYMIFFKDGLEMEKC     172

121: QIKHILANFKNYQFFIGENMNPDGMVALLDYREDGVTPYMIFFKDGLEMEKC     172

121: QIKHILANFKNYQFFIGENMNPDGMVALLDYREDGVTPYMIFFKDGLEMEKC     172
```

Exemplary HRF sequences, that bind to an immunoglobulin (Ig) include HRF that binds to one or more of IgM, IgG, IgE, IgA, or IgD. Particular IgE to which HRF binds are associated with immune disorders and diseases such as those associated with allergies (food or other antigens), asthma, hypersensitivity reactions and inflammation.

As used herein, the terms "peptide," "polypeptide" and "protein" are used interchangeably and refer to two or more amino acids covalently linked by an amide bond or equivalent. The polypeptides of the invention are of any length and include L- and D-isomers, and combinations of L- and D-isomers. The polypeptides can include modifications typically associated with post-translational processing of proteins, for example, cyclization (e.g., disulfide bond), phosphorylation, glycosylation, carboxylation, ubiquitination, myristylation, acetylation (N-terminal), amidation (C-terminal), or lipidation. Polypeptides described herein further include compounds having amino acid structural and functional analogues, for example, peptidomimetics having synthetic or non-natural amino acids or amino acid analogues, so long as the mimetic has one or more functions or activities of a native polypeptide set forth herein. Non-natural and non-amide chemical bonds, and other coupling means can also be included, for example, glutaraldehyde, N-hydroxysuccinimide esters, bifunctional maleimides, or N,N'-dicyclohexylcarbodiimide (DCC). Non-amide bonds can include, for example, ketomethylene aminomethylene, olefin, ether, thioether and the like (see, e.g., Spatola (1983) in *Chemistry and Biochemistry of Amino Acids, Peptides and Proteins*, Vol. 7, pp 267-357, "Peptide and Backbone Modifications," Marcel Decker, N.Y.).

The term "isolated," when used as a modifier of a composition (e.g., HRF sequences, antibodies, subsequences, modified forms, nucleic acids encoding same, etc.), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as fusions/chimeras, multimers/oligomers, modifications (e.g., phosphorylation, glycosylation, lipidation) or derivatized forms, or forms expressed in host cells produced by the hand of man.

An "isolated" composition (e.g., an HRF sequence or antibody) can also be "substantially pure" or "purified" when free of most or all of the materials with which it typically associates with in nature. Thus, an isolated sequence that also is substantially pure or purified does not include polypeptides or polynucleotides present among millions of other sequences, such as antibodies of an antibody library or nucleic acids in a genomic or cDNA library, for example. Typically, purity can be at least about 50%, 60% or more by mass. The purity can also be about 70% or 80% or more, and can be greater, for example, 90% or more. Purity can be determined by any appropriate method, including, for example, UV spectroscopy, chromatography (e.g., HPLC, gas phase), gel electrophoresis and sequence analysis (nucleic acid and peptide), and is typically relative to the amount of impurities, which typically does not include inert substances, such as water.

A "substantially pure" or "purified" composition can be combined with one or more other molecules. Thus, "substantially pure" or "purified" does not exclude combinations of compositions, such as combinations of HRF sequences or antibodies, subsequences, and other antibodies, agents, drugs or therapies.

As used herein, the term "recombinant," when used as a modifier of polypeptides, polynucleotides and antibodies, means that the compositions have been manipulated (i.e., engineered) in a fashion that generally does not occur in nature (e.g., in vitro). A particular example of a recombinant polypeptide would be where an HRF polypeptide or antibody is expressed by a cell transfected with a polynucleotide encoding the HRF polypeptide or antibody sequence. A particular example of a recombinant polynucleotide would be where a nucleic acid (e.g., genomic or cDNA) encoding HRF cloned into a plasmid, with or without 5', 3' or intron regions that the gene is normally contiguous with in the genome of the organism. Another example of a recombinant polynucleotide or polypeptide is a hybrid or fusion sequence, such as a chimeric HRF or antibody sequence comprising and a second sequence, such as a heterologous functional domain.

The invention also provides antibodies and subsequences thereof which are useful to bind to or that modulate an HRF activity or function, or HRF expression. The term "antibody" refers to a protein that binds to other molecules (antigens) via heavy and light chain variable domains, $V_H$ and $V_L$, respectively. Antibodies include full-length antibodies that include two heavy and two light chain sequences. Antibodies can have kappa or lambda light chain sequences, either full length as in naturally occurring antibodies, mixtures thereof (i.e., fusions of kappa and lambda chain sequences), and subsequences/fragments thereof. Naturally occurring antibody molecules contain two kappa or two lambda light chains.

In accordance with the invention, there are provided antibodies and subsequences thereof that bind to a HRF/TCTP sequence that includes or consists of a region of HRF that binds to an Ig, such as an IgE. In a particular embodiment, a sequence of HRF to which antibodies or subsequences thereof bind include or consist of amino acids 1-19 (MIIYRDLISHDEMFSDIYK (SEQ ID NO:1)) or amino acids 79-142 (QETSFTKEAYKKYIKDYMKSIKGKLE-EQRPERVKPFMTGAAEQIKHILANFKNY QFFIGEN-MNP (SEQ ID NO:2)) of mammalian HRF. Such antibodies can also bind to any subsequence of the HRF/TCTP sequence that includes or consists of a region of HRF that binds to an Ig, such as an IgE. In a particular embodiment, a subsequence is a portion of amino acids 1-19 (MII-YRDLISHDEMFSDIYK (SEQ ID NO:1)) or a portion of amino acids 79-142 (QETSFTKEAYKKYIKDYMKSIK-GKLEEQRPERVKPFMTGAAEQIKHILANFKNY QFFI-GENMNP (SEQ ID NO:2)) of mammalian HRF, or a portion of MIIYRDLISHDEMFSDIYKIREIADGLCLEVEGKM-VSRTEGNIDDSLIGGNASAEGP EGEGTESTVITGVDI- VMNHHLQETSFTKEAYKKYIKDYMKSIKGKLE-EQRPERVK PFMTGAAEQIKHILANFKNYQFFIGENMNPDGM-VALLDYREDGVTPYMIFFKDG LEMEKC (SEQ ID NO:3), wherein the subsequence is between 5-171 amino acid residues in length, e.g., 5-10, 10-20, 20-50, 100-150, or 150-171 amino acid residues in length.

The term "bind," or "binding," when used in reference to an HRF sequence or antibody, means that the HRF sequence, antibody or subsequence thereof interacts at the molecular level with an Ig, such as an IgE, or a corresponding epitope (antigenic determinant) present on HRF, respectively. Thus, an HRF binds to all or a part of an Ig sequence, and an antibody specifically binds to all or a part of sequence or an antigenic epitope on HRF (e.g., an HRF region that confers binding to an Ig, such as an IgE). Specific binding is that which is selective for the Ig or HRF. Antibodies and subsequences thereof include specific or selective binding to HRF, particularly a region or an epitope within HRF amino acids 1-19 (MIIYRDLISHDEMFSDIYK) or HRF amino acids 79-142 (QETSFTKEAYKKYIKDYMKSIKGKLE-EQRPERVKPFMTGAAEQIKHILANFKNY QFFIGEN-MNP). Specific and selective binding can be distinguished from non-specific binding using assays known in the art (e.g., competition binding, immunoprecipitation, ELISA, flow cytometry, Western blotting).

Antibodies of the invention and invention methods employing antibodies include polyclonal and monoclonal antibodies. The term "monoclonal," when used in reference to an antibody refers to an antibody that is based upon, obtained from or derived from a single clone, including any eukaryotic, prokaryotic, or phage clone. A "monoclonal" antibody is therefore defined herein structurally, and not the method by which it is produced.

Antibodies of the invention and invention methods employing antibodies can belong to any antibody class, IgM, IgG, IgE, IgA, IgD, or subclass. Exemplary subclasses for IgG are $IgG_1$, $IgG_2$, $IgG_3$ and $IgG_4$.

Antibodies of the invention and invention methods employing antibodies include antibody subsequences and fragments. Exemplary antibody subsequences and fragments include Fab, Fab', F(ab')$_2$, Fv, Fd, single-chain Fv (scFv), disulfide-linked Fvs (sdFv), light chain variable region $V_L$, heavy chain variable region $V_H$, trispecific (Fab$_3$), bispecific (Fab$_2$), diabody ((V$_L$-V$_H$)$_2$ or (V$_H$-V$_L$)$_2$), triabody (trivalent), tetrabody (tetravalent), minibody ((scF$_v$-C$_H$)$_2$), bispecific single-chain Fv (Bis-scFv), IgGdeltaCH2, scFv-Fc, (scFv)$_2$-Fc and IgG4PE. Such subsequences and fragments can have the binding affinity as the full length antibody, the binding specificity as the full length antibody, or one or more activities or functions of as a full length antibody, e.g., a function or activity of HRF binding antibody.

Antibody subsequences and fragments can be combined. For example, a $V_L$ or $V_H$ subsequences can be joined by a linker sequence thereby forming a $V_L$-$V_H$ chimera. A combination of single-chain Fvs (scFv) subsequences can be joined by a linker sequence thereby forming a scFv-scFv chimera. Antibody subsequences and fragments include single-chain antibodies or variable region(s) alone or in combination with all or a portion of other subsequences.

Antibody subsequences and fragments can be prepared by proteolytic hydrolysis of the antibody, for example, by pepsin or papain digestion of whole antibodies. Antibody subsequences and fragments produced by enzymatic cleavage with pepsin provide a 5S fragment denoted F(ab')$_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., U.S. Pat. Nos. 4,036,945 and 4,331,647; and Edelman et al., *Methods Enymol.* 1:422 (1967)). Other methods of cleaving antibodies, such as separation of heavy chains to form monovalent light-heavy chain fragments, further cleavage of fragments, or other enzymatic or chemical may also be used.

Epitopes typically are short amino acid sequences, e.g. about five to 15 amino acids in length. Epitopes can be contiguous or non-contiguous. A non-contiguous amino acid sequence epitope forms due to protein folding. For example, an epitope can include a non-contiguous amino acid sequence, such as a 5 amino acid sequence and an 8 amino acid sequence, which are not contiguous with each other, but form an epitope due to protein folding. Techniques for identifying epitopes are known to the skilled artisan and include screening overlapping oligopeptides for binding to antibody (for example, U.S. Pat. No. 4,708,871), phage display peptide library kits, which are commercially available for epitope mapping (New England BioLabs). Epitopes may also be identified by inference when epitope length peptide sequences are used to immunize animals from which antibodies that bind to the peptide sequence are obtained and can be predicted using computer programs, such as BEPITOPE (Odorico et al., *J. Mol. Recognit.* 16:20 (2003)).

Methods of producing polyclonal and monoclonal antibodies are known in the art. For example, HRF, or a subsequence thereof, or an immunogenic fragment thereof, optionally conjugated to a carrier such as keyhole limpet hemocyanin (KLH) or ovalbumin (e.g., BSA), or mixed with an adjuvant such as Freund's complete or incomplete adjuvant, and used to immunize an animal. Using conventional hybridoma technology, splenocytes from immunized animals that respond to HRF can be isolated and fused with myeloma cells. Monoclonal antibodies produced by the hybridomas can be screened for reactivity with HRF or an immunogenic fragment thereof.

Animals that may be immunized include mice, rats, rabbits, goats, sheep, cows or steer, guinea pigs or primates. Initial and any optional subsequent immunization may be through intravenous, intraperitoneal, intramuscular, or subcutaneous routes. Subsequent immunizations may be at the same or at different concentrations of HRF, or a subsequence thereof, preparation, and may be at regular or irregular intervals.

Human antibodies can be produced by immunizing human transchromosomic KM Mice™ (WO 02/43478) or HAC mice (WO 02/092812). KM mice and HAC mice express human immunoglobulin genes. Using conventional hybridoma technology, splenocytes from immunized mice that were high responders to the antigen can be isolated and fused with myeloma cells. A monoclonal antibody can be obtained that binds to the antigen. An overview of the technology for producing human antibodies is described in Lonberg and Huszar (*Int. Rev. Immunol.* 13:65 (1995)). Transgenic animals with one or more human immunoglobulin genes (kappa or lambda) that do not express endogenous immunoglobulins are described, for example in, U.S. Pat. No. 5,939,598. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

Antibodies can also be generated using other techniques including hybridoma, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988).

Antibodies of the invention and invention methods employing antibodies include mammalian, primatized, humanized, fully human antibodies and chimeras. A mammalian antibody is an antibody produced by a mammal, transgenic or non-transgenic, or a non-mammalian organism engineered to produce a mammalian antibody, such as a non-mammalian cell (bacteria, yeast, insect cell), animal or plant.

The term "human" when used in reference to an antibody, means that the amino acid sequence of the antibody is fully human, i.e., human heavy and human light chain variable and human constant regions. Thus, all of the amino acids are human or exist in a human antibody. An antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); Chothia and Lesk (1987). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991). Human antibodies therefore include antibodies in which one or more amino acid residues have been substituted with one or more amino acids present in any other human antibody.

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

Antibodies of the invention and invention methods employing antibodies include those to as "primatized" antibodies, which are "humanized" except that the acceptor human immunoglobulin molecule and framework region amino acid residues may be any primate amino acid residue (e.g., ape, gibbon, gorilla, chimpanzees orangutan, macaque), in addition to any human residue. Human FR residues of the immunoglobulin can be replaced with corresponding non-human residues. Residues in the CDR or human framework regions can therefore be substituted with a corresponding residue from the non-human CDR or framework region donor antibody to alter, generally to improve, antigen affinity or specificity, for example. A humanized antibody may include residues, which are found neither in the human antibody nor in the donor CDR or framework sequences. For example, a FR substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332:323 (1988)).

The term "chimeric" and grammatical variations thereof, when used in reference to an antibody, means that the amino acid sequence of the antibody contains one or more portions that are derived from, obtained or isolated from, or based upon two or more different species. For example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences in any region of the antibody.

Antibodies can be humanized using a variety of techniques known in the art including, for example, CDR-grafting (EP 239,400; WO91/09967; U.S. Pat. Nos. 5,225, 539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have previously used to produce humanized antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Suitable techniques that additionally may be employed in antibody methods include affinity purification, non-denaturing gel purification, HPLC or RP-HPLC, size exclusion, purification on protein A column, or any combination of these techniques. The antibody isotype can be determined using an ELISA assay, for example, a human Ig can be identified using mouse Ig-absorbed anti-human Ig.

HRF or a subsequence thereof, suitable for generating antibodies can be produced by any of a variety of standard protein purification or recombinant expression techniques known in the art. For example, HRF or a subsequence thereof can be recombinantly produced or obtained from cells.

Forms of protein suitable for generating an immune response include peptide subsequences of full length protein, such as an immunogenic fragment. Additional forms of protein include preparations or cell extracts or fractions, partially purified HRF or a subsequence thereof, as well as whole cells that express HRF, or a subsequence thereof, or preparations of HRF or a subsequence thereof, expressing cells.

Proteins and antibodies, as well as subsequences and fragments thereof, can be produced by genetic methodology. Such techniques include expression of all or a part of the gene encoding the protein or antibody into a host cell such as Cos cells or *E. coli*. The recombinant host cells synthesize full length or a subsequence, for example, an scFv (see, e.g., Whitlow et al., In: *Methods: A Companion to Methods in Enzymology* 2:97 (1991), Bird et al., *Science* 242:423 (1988); and U.S. Pat. No. 4,946,778). Single-chain Fvs and antibodies can be produced as described in U.S. Pat. Nos. 4,946,778 and 5,258,498; Huston et al., *Methods Enzymol.* 203:46 (1991); Shu et al., *Proc. Natl. Acad. Sci. USA* 90:7995 (1993); and Skerra et al., *Science* 240:1038 (1988).

In accordance with the invention, also provided are modified forms of proteins, antibodies, nucleic acids, and other compositions, provided that the modified form retains, at least a part of, a function or activity of the unmodified or reference protein, nucleic acid, or antibody. For example, a modified HRF (e.g., a subsequence or fragment) can retain at least partial binding to an Ig, such as an IgE. In another non-limiting example, a modified HRF (e.g., a subsequence or fragment) can be used as an immunogen to produce antibodies that specifically bind to HRF. In yet another non-limiting example, a modified HRF or HRF binding antibody (e.g., a subsequence or fragment) can be used in an invention method.

The invention therefore includes modified forms of proteins, antibodies, nucleic acids, and other compositions. Such modified forms typically retain, at least a part of, one or more functions or activities of an unmodified or reference protein, nucleic acid, or antibody. Such activities include, for example, for HRF, binding to a receptor, such as an Ig, such as an IgE, or modulating HRF activity, function or expression, etc., and for an HRF antibody, binding to HRF and inhibiting interactions between HRF and Igs, such as IgE.

As used herein, the term "modify" and grammatical variations thereof, means that the composition deviates from a reference composition. Such modified proteins, nucleic acids and other compositions may have greater or less activity or function, or have a distinct function or activity compared with a reference unmodified protein, nucleic acid, or composition.

A "functional polypeptide" or "active polypeptide" refers to a modified polypeptide that possesses at least one partial function or biological activity characteristic of a native wild type or full length counterpart polypeptide as described herein, which can be identified through an assay. As described herein, a particular example of a biological activity of HRF is to bind to an Ig, such as an IgE. Another example of a biological activity is the ability of an antibody to bind to HRF sequences, such as antibody fragments that can bind to HRF, such as the sequence region of HRF that confers binding to an Ig, such as an IgE. Yet another example is an HRF subsequence that modulates (e.g., decrease, reduce, inhibit, suppress, limit or control) native (endogenous) HRF activity, function or expression in vitro, ex vivo or in vivo, presumably by binding to HRF-R which in turn limits activity or function or downstream signaling that occurs between native HRF and native HRF-R.

Modifications include, for example, substitutions, additions, insertions and deletions to the amino acid sequences set forth herein, which can be referred to as "variants." Exemplary sequence substitutions, additions, and insertions include a full length or a portion of a sequence with one or more amino acids substituted, added or inserted, for example of an HRF sequence, wherein the modified HRF binds to an Ig, such as an IgE, or of an antibody that binds to HRF, such as the sequence region of HRF that confers binding to an Ig, such as an IgE.

Modified polypeptides include, for example, non-conservative and conservative substitutions of the HRF or antibody amino acid sequences. In particular embodiments, a modified protein has one or a few (e.g., 10-20% of the residues of total protein length, or 2-10 residues, substituted) conservative or non-conservative substitutions.

As used herein, the term "conservative substitution" denotes the replacement of an amino acid residue by another, chemically or biologically similar residue. Biologically similar means that the substitution does not destroy a biological activity or function, e.g., HRF binding activity to an Ig, or antibody binding to HRF. Structurally similar means that the amino acids have side chains with similar length, such as alanine, glycine and serine, or a similar size. Chemical similarity means that the residues have the same charge or are both hydrophilic or hydrophobic. Particular examples of conservative substitutions include the substitution of a hydrophobic residue such as isoleucine, valine, leucine or methionine for another, the substitution of a polar residue for another, such as the substitution of arginine for lysine, glutamic for aspartic acids, or glutamine for asparagine, and the like. The term "conservative substitution" also includes the use of a substituted amino acid in place of an unsubstituted parent amino acid. Such proteins that include amino acid substitutions can be encoded by a nucleic acid. Consequently, nucleic acid sequences encoding proteins that include amino acid substitutions are also provided.

Modified proteins also include one or more D-amino acids substituted for L-amino acids (and mixtures thereof), structural and functional analogues, for example, peptidomimetics having synthetic or non-natural amino acids or amino acid analogues and derivatized forms. Modifications include cyclic structures such as an end-to-end amide bond between the amino and carboxy-terminus of the molecule or intra- or inter-molecular disulfide bond.

Modified forms further include "chemical derivatives," in which one or more amino acids has a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxl groups that form O-acyl or O-alkyl derivatives as well as naturally occurring amino acid derivatives, for example, 4-hydroxyproline, for proline, 5-hydroxylysine for lysine, homoserine for serine, ornithine for lysine etc. Also included are amino acid derivatives that can alter covalent bonding, for example, the disulfide linkage that forms between two cysteine residues that produces a cyclized polypeptide.

Modified forms of protein (e.g., HRF, HRF fragment or antibody), nucleic acid, and other compositions include additions and insertions, such as of heterologous domains. For example, an addition (e.g., heterologous domain) can be the covalent or non-covalent attachment of any type of molecule to a protein (e.g., HRF, HRF fragment or HRF antibody), nucleic acid or other composition. Typically additions and insertions (e.g., a heterologous domain) confer a complementary or a distinct function or activity.

Additions and insertions include chimeric and fusion polypeptide or nucleic acid sequences, which is a sequence having one or more molecules not normally present in a reference native (wild type) sequence covalently attached to the sequence. The terms "fusion" or "chimeric" and grammatical variations thereof, when used in reference to a molecule, such as a HRF, means that a portions or part of the molecule contains a different entity distinct (heterologous) from the molecule (e.g., HRF, HRF fragment or antibody) as they do not typically exist together in nature. That is, for example, one portion of the fusion or chimera, such as HRF, includes or consists of a portion that does not exist together in nature, and is structurally distinct. A particular example is a molecule, such as an amino acid sequence of another protein (e.g., immunoglobulin such as an Fc domain, or antibody) attached to HRF to produce a chimera, or a chimeric polypeptide, to impart a distinct function (e.g., increased solubility, in vivo half life, etc.). Another particular example is an amino acid sequence of another protein to produce a multifunctional protein (e.g., multifunctional HRF or multispecific antibody).

Additions and insertions also include label or a tag, which can be used to provide an agent that is detectable or that is useful for isolating the tagged entity (e.g., HRF, HRF fragment or HRF antibody). A detectable label can be attached, for example, to (e.g., linked conjugated) HRF, HRF fragment or HRF antibody, or be within or be one or more atoms that comprise the molecule.

Non-limiting exemplary detectable labels also include a radioactive material, such as a radioisotope, a metal or a metal oxide. Radioisotopes include radionuclides emitting alpha, beta or gamma radiation. In particular embodiments, a radioisotope can be one or more of: $^{3}H$, $^{10}B$, $^{18}F$, $^{11}C$, $^{14}C$, $^{13}N$, $^{18}O$, $^{15}O$, $^{32}P$, $P^{33}$, $^{35}S$, $^{35}Cl$, $^{45}Ti$, $^{46}Sc$, $^{47}Sc$, $^{51}Cr$, $^{52}Fe$, $^{59}Fe$, $^{57}Co$, $^{60}Cu$, $^{61}Cu$, $^{62}Cu$, $^{64}Cu$, $^{67}Cu$, $^{67}Ga$, $^{68}Ga$, $^{72}As$, $^{76}Br$, $^{77}Br$, $^{81m}Kr$, $^{82}Rb$, $^{85}Sr$, $^{89}Sr$, $^{86}Y$, $^{90}Y$, $^{95}Nb$, $^{94m}Tc$, $^{99m}Tc$, $^{97}Ru$, $^{103}Ru$, $^{105}Rh$, $^{109}Cd$, $^{111}In$, $^{113}Sn$, $^{113m}In$, $^{114}In$, $I^{125}$, $I^{131}$, $^{140}La$, $^{141}Ce$, $^{149}Pm$, $^{153}Gd$, $^{157}Gd$, $^{153}Sm$, $^{161}Tb$, $^{166}Dy$, $^{166}Ho$, $^{169}Er$, $^{169}Y$, $^{175}Yb$, $^{177}Lu$, $^{186}Re$, $^{188}Re$, $^{201}Tl$, $^{203}Pb$, $^{211}At$, $^{212}Bi$ or $^{225}Ac$.

Additional non-limiting exemplary detectable labels include a metal or a metal oxide. In particular embodiments, a metal or metal oxide is one or more of: gold, silver, copper, boron, manganese, gadolinium, iron, chromium, barium, europium, erbium, praseodymium, indium, or technetium. In additional embodiments, a metal oxide includes one or more of: Gd(III), Mn(II), Mn(III), Cr(II), Cr(III), Cu(II), Fe (III), Pr(III), Nd(III) Sm(III), Tb(III), Yb(III) Dy(III), Ho(III), Eu(II), Eu(III), or Er(III).

Further non-limiting exemplary detectable labels include contrast agents (e.g., gadolinium; manganese; barium sulfate; an iodinated or noniodinated agent; an ionic agent or nonionic agent); magnetic and paramagnetic agents (e.g., iron-oxide chelate); nanoparticles; an enzyme (horseradish peroxidase, alkaline phosphatase, β-galactosidase, or acetylcholinesterase); a prosthetic group (e.g., streptavidin/biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); or a bioluminescent material (e.g., luciferase, luciferin, aequorin).

Additional non-limiting examples of tags and/or detectable labels include enzymes (horseradish peroxidase, urease, catalase, alkaline phosphatase, beta-galactosidase, chloramphenicol transferase); enzyme substrates; ligands (e.g., biotin); receptors (avidin); GST-, T7-, His-, myc-, HA- and FLAG-tags; electron-dense reagents; energy transfer molecules; paramagnetic labels; fluorophores (fluorescein, fluorscamine, rhodamine, phycoerthrin, phycocyanin, allophycocyanin); chromophores; chemi-luminescent (imidazole, luciferase, acridinium, oxalate); and bio-luminescent agents.

As set forth herein, a detectable label or tag can be linked or conjugated (e.g., covalently) to the molecule (e.g., HRF, HRF fragment or antibody). In various embodiments a detectable label, such as a radionuclide or metal or metal oxide can be bound or conjugated to the agent, either directly or indirectly. A linker or an intermediary functional group can be used to link the molecule to a detectable label or tag. Linkers include amino acid or peptidomimetic sequences inserted between the molecule and a label or tag so that the two entities maintain, at least in part, a distinct function or activity. Linkers may have one or more properties that include a flexible conformation, an inability to form an ordered secondary structure or a hydrophobic or charged character which could promote or interact with either domain. Amino acids typically found in flexible protein regions include Gly, Asn and Ser. The length of the linker sequence may vary without significantly affecting a function or activity.

Linkers further include chemical moieties, conjugating agents, and intermediary functional groups. Examples include moieties that react with free or semi-free amines, oxygen, sulfur, hydroxy or carboxy groups. Such functional groups therefore include mono and bifunctional cross-linkers, such as sulfo-succinimidyl derivatives (sulfo-SMCC, sulfo-SMPB), in particular, disuccinimidyl suberate (DSS), BS3 (Sulfo-DSS), disuccinimidyl glutarate (DSG) and disuccinimidyl tartrate (DST). Non-limiting examples include diethylenetriaminepentaacetic acid (DTPA) and ethylene diaminetetracetic acid.

Additional non-limiting examples of amino acid modifications include protein subsequences and fragments. Exemplary HRF subsequences and fragments include a portion of the HRF sequence that binds to an Ig, such as an IgE. Exemplary HRF subsequences and fragments also include an immunogenic portion of HRF.

As used herein, the term "subsequence" or "fragment" means a portion of the full length molecule. A subsequence of a polypeptide sequence, such as HRF or an antibody sequence, has one or more less amino acids than a full length HRF (e.g. one or more internal or terminal amino acid deletions from either amino or carboxy-termini). A subsequence of an antibody has one or more less amino acids than a full length antibody heavy or light chain or constant region. A nucleic acid subsequence has at least one less nucleotide than a full length comparison nucleic acid sequence. Subsequences therefore can be any length up to the full length native molecule.

Functional subsequences can vary in size from a polypeptide as small as an epitope capable of binding an antibody molecule (i.e., about five amino acids) up to the entire length of a reference polypeptide. Functional HRF subsequences are at least 5-10, 10-20, 20-30, 30-40, 40-50, 50-75, 75-100, 100-150, or 150-171 amino acid residues. Functional antibody subsequences are at least 5-10, 10-20, 20-30, 30-40, 40-50, 50-75, 75-100, 100-125 amino acid residues.

Thus, in another embodiment, the invention provides functional polypeptides or functional subsequences thereof. In particular embodiments, a functional polypeptide or functional subsequence shares at least 50% identity with a reference sequence, for example, an HRF polypeptide sequence and that binds to an Ig, such as an IgE, or is capable of modulating HRF activity, function or expression, or an antibody that binds to the HRF sequence region that mediates HRF binding to an Ig, such as an IgE. In other embodiments, the polypeptides have at least 60%, 70%, 75% or more identity (e.g., 80%, 85% 90%, 95%, 96%, 97%, 98%, 99% or more identity) to a reference sequence, such as an HRF polypeptide sequence that binds to an Ig, such as an IgE, or is capable of modulating HRF activity, function or expression. The functional polypeptides or functional subsequences thereof including modified forms of the invention, such as HRF and antibodies that bind to HRF, may have one or more of the functions or biological activities described herein.

The term "identity" and grammatical variations thereof, mean that two or more referenced entities are the same. Thus, where two polypeptide (e.g., HRF or antibody) sequences are identical, they have the same amino acid sequence, at least within the referenced region or portion. Where two nucleic acid sequences are identical, they have the same polynucleotide sequence, at least within the referenced region or portion. The identity can be over a defined area (region or domain) of the sequence. An "area of identity" refers to a portion of two or more referenced entities that are the same. Thus, where two protein or nucleic acid sequences are identical over one or more sequence regions they share identity within that region.

The percent identity can extend over the entire sequence length of the polypeptide (e.g., HRF). In particular aspects, the length of the sequence sharing the percent identity is 5 or more contiguous amino acids, e.g., 5, 6, 7, 8, 9, 10, 11, 12, 13, 14, 15, 16, 17, 18, 19, 20, 21, 22, 23, 24, 25, etc. contiguous amino acids. In additional particular aspects, the length of the sequence sharing the percent identity is 25 or more contiguous amino acids, e.g., 26, 27, 28, 29, 30, 31, 32, 33, 34, 35, etc. contiguous amino acids. In further particular aspects, the length of the sequence sharing the percent identity is 35 or more contiguous amino acids, e.g., 35, 36, 37, 38, 39, 40, 41, 42, 43, 44, 45, 45, 47, 48, 49, 50, etc., contiguous amino acids. In yet additional particular aspects, the length of the sequence sharing the percent identity is 50 or more contiguous amino acids, e.g., 50-55, 55-60, 60-65, 65-70, 70-75, 75-80, 80-85, 85-90, 90-95, 95-100, 100-110, etc. contiguous amino acids.

The terms "homologous" or "homology" mean that two or more referenced entities share at least partial identity over a given region or portion. "Areas, regions or domains" of homology or identity mean that a portion of two or more referenced entities share homology or are the same. Thus, where two sequences are identical over one or more sequence regions they share identity in these regions. "Substantial homology" means that a molecule is structurally or functionally conserved such that it has or is predicted to have at least partial structure or function of one or more of the structures or functions (e.g., a biological function or activity) of the reference molecule, or relevant/corresponding region or portion of the reference molecule to which it shares homology. An HRF sequence or an antibody or subsequence with substantial homology has or is predicted to have at least partial activity or function as the reference HRF sequence or antibody.

The extent of identity (homology) between two sequences can be ascertained using a computer program and mathematical algorithm known in the art. Such algorithms that calculate percent sequence identity (homology) generally account for sequence gaps and mismatches over the comparison region or area. For example, a BLAST (e.g., BLAST 2.0) search algorithm (see, e.g., Altschul et al., J. Mol. Biol. 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., Proc. Natl. Acad. Sci. USA 85:2444 (1988); Pearson, Methods Mol. Biol. 132:185 (2000); and Smith et al., J. Mol. Biol. 147:195 (1981)). Programs for quantitating protein structural similarity using Delaunay-based topological mapping have also been developed (Bostick et al., Biochem Biophys Res Commun. 304:320 (2003)).

Modifications can be produced using methods known in the art (e.g., PCR based site-directed, deletion and insertion mutagenesis, chemical modification and mutagenesis, cross-linking, etc.), or may be spontaneous or naturally occurring (e.g. random mutagenesis). For example, naturally occurring allelic variants can occur by alternative RNA splicing, polymorphisms, or spontaneous mutations of a nucleic acid encoding HRF polypeptide. Further, deletion of one or more amino acids can also result in a modification of the structure of the resultant polypeptide without significantly altering a biological function or activity. Deletion of amino acids can lead to a smaller active molecule. For example, as set forth herein, removal of HRF amino or carboxy terminal or internal amino acids does not destroy Ig binding activity.

Modified HRF sequences, antibodies and subsequences fragment of the invention may have an affinity greater or less than 2-5, 5-10, 10-100, 100-1000 or 1000-10,000-fold affinity, or any numerical value or range within or encompassing such values, than a comparison HRF sequence or antibody. In one embodiment, an HRF sequence has a binding affinity for an Ig, such as an IgE, within about 1-5000 fold of the binding affinity of HRF amino acids 1-19 (MIIYRDLISH-DEMFSDIYK (SEQ ID NO:1)) or HRF amino acids 79-142 (QETSFTKEAYKKYIKDYMKSIKGKLEEQRPERVKPF-MTGAAEQIKHILANFKNY QFFIGENMNP (SEQ ID NO:2)), for binding to an Ig, such as an IgE.

The term "substantially the same" when used in reference to an HRF sequence or subsequence thereof that binds to an Ig, or an antibody or subsequence thereof that binds to HRF, means that the relative binding affinity or avidity for binding to an Ig, such as an IgE, means that the binding is within 100 fold (greater or less than) of the binding affinity of a reference HRF sequence or antibody (e.g., an Ig, such as an IgE, or HRF). Binding affinity can be determined by association ($K_a$) and dissociation ($K_D$ or $K_d$) rate. Equilibrium affinity constant, K, is the ratio of $K_a/K_d$. Association ($K_a$) and dissociation ($K_D$ or $K_d$) rates can be measured using surface plasmon resonance (SPR) (Rich and Myszka, Curr. Opin. Biotechnol. 11:54 (2000); Englebienne, Analyst. 123: 1599 (1998)). Instrumentation and methods for real time detection and monitoring of binding rates are known and are commercially available (BiaCore 2000, Biacore AB, Upsala, Sweden; and Malmqvist, Biochem. Soc. Trans. 27:335 (1999)). Thus, for example, if binding of a reference HRF antibody to HRF has a $K_D$ of $10^{-9}$ M, then an antibody which has substantially the same binding affinity as the reference antibody will have a $K_D$ within the range of $10^{-7}$ M to $K_D$ $10^{-11}$ M for binding to HRF.

The invention also provides polynucleotides encoding HRF polypeptides and antibodies that bind to HRF. In one embodiment, a polynucleotide sequence has about 65% or more identity (e.g., 70%, 75%, 80%, 85%, 90%, 95%, 96%, 97%, 98%, 99% or more) to a sequence encoding an HRF subsequence that binds to an Ig, such as an IgE. In particular embodiments, a nucleic acid encodes all or a portion of amino acids 1-19 (MIIYRDLISHDEMFSDIYK (SEQ ID NO:1)) or amino acids 79-142 (QETSFTKEAYK- KYIKDYMKSIKGKLEEQRPERVKPFMTGAAEQIKHI-LANFKNY QFFIGENMNP (SEQ ID NO:2)) of mammalian HRF. Such polynucleotides can therefore encode any subsequence of the HRF/TCTP sequence that includes or consists of a region of HRF that binds to an Ig, such as an IgE. Such encoded subsequences can be between 5-171 amino acid residues in length, e.g., 5-10, 10-20, 20-50, 100-150, or 150-171 amino acid residues in length.

As used herein, the terms "polynucleotide" and "nucleic acid" are used interchangeably to refer to all forms of nucleic acid, oligonucleotides, primers, and probes, including deoxyribonucleic acid (DNA) and ribonucleic acid (RNA). Polynucleotides include genomic DNA, cDNA and antisense DNA, and spliced or unspliced mRNA, rRNA tRNA and antisense RNA (e.g., RNAi). Polynucleotides include naturally occurring, synthetic, and intentionally altered or modified polynucleotides as well as analogues and derivatives. Alterations can result in increased stability due to resistance to nuclease digestion, for example. Polynucleotides can be double, single or triplex, linear or circular, and can be of any length.

Polynucleotides of the invention include sequences that are degenerate as a result of the genetic code. There are 20 natural amino acids, most of which are specified by more than one codon. Degenerate sequences may not selectively hybridize to other invention nucleic acids; however, they are nonetheless included as they encode invention HRF polypeptides and modified forms including subsequences thereof. Thus, in another embodiment, degenerate nucleotide sequences that encode HRF polypeptides and modified forms including subsequences thereof as set forth herein, are provided.

Polynucleotide sequences include sequences having 15-20, 20-30, 30-40, 50-50, or more contiguous nucleotides. In additional aspects, the polynucleotide sequence includes a sequence having 60 or more, 70 or more, 80 or more, 100 or more, 120 or more, 140 or more, 160 or more contiguous nucleotides, up to the full length coding sequence.

Polynucleotide sequences for HRF include complementary sequences (e.g., antisense to all or a part of HRF). Antisense polynucleotides, to decrease activity, function or expression of HRF, for example, do not require expression control elements to function in vivo. However, antisense may be encoded by a nucleic acid and such a nucleic acid may be operatively linked to an expression control element for sustained or increased expression of the encoded antisense in cells or in vivo. Sequences encoding HRF subsequences that bind to an Ig, such as an IgE also are included. Such HRF forms may decrease, reduce, inhibit, suppress, limit or control binding or interaction of the native endogenous HRF with HRF-R thereby modulating signaling.

Further included are double stranded RNA sequences from an HRF coding region. The use of double stranded RNA sequences (known as "RNAi") for inhibiting gene expression, for example, in insects and in other organisms is known in the art (Kennerdell et al., *Cell* 95:1017 (1998); Fire et al., *Nature,* 391:806 (1998)).

Such complementary, antisense and RNAi sequences can interfere with HRF activity, function or expression and be useful for modulating HRF. An effective amount of complementary, antisense or RNAi sequences from the coding region of HRF can inhibit HRF activity, function or expression and are therefore useful in the therapeutic and other methods of treatment as described herein. Such invention polynucleotides can be further contained within carriers or vectors suitable for passing through a cell membrane for cytoplasmic delivery, and can be modified so as to be nuclease resistant in order to enhance their stability or efficacy in the invention methods and compositions, for example.

Thus, in another embodiment, polynucleotides encoding HRF including the nucleotide sequence encoding full length or a subsequence of: MIIYRDLISHDEMFSDIYKIRE-IADGLCLEVEGKMVSRTEGNIDDSLIGGNASAEGP EGEGTESTVITGVDIVMNHHLQETSFTKEAYK-KYIKDYMKSIKGKLEEQRPERVK PFMTGAAEQIKHI-LANFKNYQFFIGENMNPDGMVALLDYREDGVT-PYMIFFKDG LEMEKC, (SEQ ID NO:3) as well as nucleic acid sequences complementary to the sequence or subsequence (e.g., complementary, antisense polynucleotides), are provided.

Polynucleotides encoding full length or subsequences of HRF polypeptide are included herein. Particular examples are nucleic acid sequences that encode HRF functional subsequences. As used herein, the term "functional polynucleotide" denotes a polynucleotide that encodes a functional polypeptide as described herein. Thus, the invention includes polynucleotides encoding a polypeptide having a function or activity of an amino acid sequence set forth in HRF, e.g., MIIYRDLISHDEMFSDIYKIREIADGLCLEV-EGKMVSRTEGNIDDSLIGGNASAEGP EGEGTESTVIT-GVDIVMNHHLQETSFTKEAYKKYIKDYMKSIK-GKLEEQRPERVK PFMTGAAEQIKHILANFKNYQFFIGENMNPDGM-VALLDYREDGVTPYMIFFKDG LEMEKC.

Additional polynucleotides include fragments of the above-described nucleic acid sequences that are at least 15 bases in length, which is of sufficient length to permit a selective hybridization to an HRF nucleic acid. Polynucleotide fragments of at least 15 bases in length can be used to screen for HRF related genes in other organisms, such as mammals or insects, and are referred to herein as "probes."

Invention probes and agents additionally can have a "tag" or "label" or "detectable moiety" linked thereto that provides a means of isolation or identification, or a detection signal (e.g., radionuclides, fluorescent, chemi- or other luminescent moieties). If necessary, additional reagents can be used in combination with the detectable moieties to provide or enhance the detection signal. Such labels and detectable moieties also can be linked to invention HRF polypeptides, nucleic acids, antibodies, and modified forms disclosed herein.

Thus, in accordance with the invention there are provided isolated polynucleotides that selectively hybridize to the polynucleotides described herein. In one embodiment, an isolated polynucleotide sequence hybridizes under stringent conditions to a polynucleotide encoding full length or a subsequence of HRF, e.g., encoding all or a subsequence of: MIIYRDLISHDEMFSDIYKIREIADGLCLEVEGKMVS-RTEGNIDDSLIGGNASAEGP EGEGTESTVITGVDIVM-NHHLQETSFTKEAYKKYIKDYMKSIKGKLE-EQRPERVK PFMTGAAEQIKHILANFKNYQFFIGENMNPDGM-VALLDYREDGVTPYMIFFKDG LEMEKC (SEQ ID NO:3). In another embodiment, an isolated polynucleotide sequence hybridizes under stringent conditions to a polynucleotide encoding full length or a subsequence of HRF sequence set forth herein.

Hybridization refers to binding between complementary nucleic acid sequences (e.g., sense/antisense). As used herein, the term "selective hybridization" refers to hybridization under moderately stringent or highly stringent conditions, which can distinguish HRF related nucleotide sequences from unrelated sequences. Screening procedures which rely on hybridization allow isolation of related nucleic acid sequences, from any organism.

In nucleic acid hybridization reactions, conditions used in order to achieve a particular level of stringency will vary, depending on the nature of the nucleic acids being hybridized. For example, the length, degree of sequence complementarity, sequence composition (e.g., the GC v. AT content), and type (e.g., RNA v. DNA) of the hybridizing regions can be considered in selecting particular hybridization conditions. An additional consideration is whether one of the nucleic acids is immobilized, for example, on a filter. As is understood by those skilled in the art, the Tm (melting temperature) refers to the temperature at which the binding between two sequences is no longer stable. For two sequences to form a stable hybrid, the temperature of the reaction must be less than the Tm for the particular hybridization conditions. In general, the stability of a nucleic acid hybrid decreases as the sodium ion decreases and the temperature of the hybridization reaction increases.

Typically, wash conditions are adjusted so as to attain the desired degree of stringency. Thus, hybridization stringency can be determined, for example, by washing at a particular condition, e.g., at low stringency conditions or high stringency conditions, or by using each of the conditions, e.g., for 10-15 minutes each, in the order listed below, repeating any or all of the steps listed. Optimal conditions for selective hybridization will vary depending on the particular hybridization reaction involved.

An example of a moderately stringent hybridization condition is as follows: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of a moderately-high stringent hybridization condition is as follows: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash); and 0.1×SSC/0.1% SDS at about 52° C. (moderately-high stringency wash). An example of high stringency hybridization conditions is as follows: 2×SSC/0.1% SDS at about room temperature (hybridization conditions); 0.5×SSC/0.1% SDS at about room temperature (low stringency wash); 0.5×SSC/0.1% SDS at about 42° C. (moderate stringency wash); and 0.1×SSC/0.1% SDS at about 65° C. (high stringency wash).

Polynucleotides of the invention can be obtained using various standard cloning and chemical synthesis techniques. Purity of polynucleotides can be determined through sequencing, gel electrophoresis and the like. For example, nucleic acids can be isolated using hybridization as set forth herein or computer-based database screening techniques known in the art. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

The invention HRF polynucleotides can include an expression control element distinct from the endogenous HRF gene (e.g., a non-native element), or exclude a control element from the native HRF gene to control expression of an operatively linked HRF nucleic acid. Such polynucleotides containing an expression control element controlling expression of a nucleic acid can be modified or altered as set forth herein, so long as the modified or altered polynucleotide has one or more functions or activities.

For expression in cells, invention polynucleotides, if desired, may be inserted into a vector. Accordingly, invention compositions and methods further include polynucleotide sequences inserted into a vector. The term "vector" refers to a plasmid, virus or other vehicle known in the art that can be manipulated by insertion or incorporation of a polynucleotide. Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including expression control elements as set forth herein, present within a vector are included to facilitate proper transcription and translation (e.g., splicing signal for introns, maintenance of the correct reading frame of the gene to permit in-frame translation of mRNA and, stop codons etc.).

Compositions and methods of the invention are applicable to treating numerous disorders. Disorders treatable in accordance with the invention include disorders in which decreasing, reducing, inhibiting, suppressing, limiting or controlling a response mediated or associated with HRF activity, function or expression can provide a subject with a benefit. Disorders include undesirable or aberrant immune responses, immune disorders and immune diseases including, for example, food allergy, allergic reaction, hypersensitivity, inflammatory response, inflammation, and airway constriction.

As used herein, an "undesirable immune response" or "aberrant immune response" refers to any immune response, activity or function that is greater or less than desired or physiologically normal. An undesirable immune response, function or activity can be a normal response, function or activity. Thus, normal immune responses so long as they are undesirable, even if not considered aberrant, are included within the meaning of these terms. An undesirable immune response, function or activity can also be an abnormal response, function or activity. An abnormal (aberrant) immune response, function or activity deviates from normal. Undesirable and aberrant immune responses can be humoral, cell-mediated or a combination thereof, either chronic or acute.

One non-limiting example of an undesirable or aberrant immune response is where the immune response is hyper-responsive, such as in the case of an autoimmune disorder or disease. Another example of an undesirable or aberrant immune response is where an immune response leads to acute or chronic inflammatory response or inflammation in any tissue or organ, such as an allergy (e.g., food allergy or asthma).

The terms "immune disorder" and "immune disease" mean, an immune function or activity, that is greater than (e.g., autoimmunity) or less than (e.g., immunodeficiency) desired, and which is characterized by different physiological symptoms or abnormalities, depending upon the disorder or disease. Particular non-limiting examples of immune disorders and diseases to which the invention applies include, for example, food allergy, allergic reaction, hypersensitivity, inflammatory response, inflammation, and airway constriction. Additional disorders are generally characterized as an undesirable or aberrant increased or inappropriate response, activity or function of the immune system. Disorders and diseases that can be treated in accordance with the invention include, but are not limited to, disorders and disease that cause cell or tissue/organ damage in the subject.

In accordance with the invention, there are provided methods of treating a food allergy. In one embodiment, a method includes contacting histamine releasing factor (HRF)/translationally controlled tumor protein (TCTP) with a compound that inhibits or reduces binding of HRF/TCTP to an immunoglobulin thereby treating the food allergy.

As used herein, the term "food allergy" refers to an adverse immune response to food proteins, which is unlike lactose intolerance, food poisoning or food aversions. A particular type of food allergy is a "rapid" type of food allergy, often called as "IgE-mediated" food hypersensitivity. Symptoms of food allergy may include systemic anaphylaxis (e.g., hypotension, loss of consciousness, and death), skin (e.g., flushing, urticaria, angioedema, and worsening eczema), eye (e.g., allergic conjunctivitis), gut (e.g., nausea, cramping, vomiting, diarrhea, and abdominal pain), and respiratory tract reactions (e.g., rhinitis and asthma) (Sicherer et al., Pediatrics 102:e6 (1998); Atkins et al., J. Allergy Clin. Immunol. 75:356 (1985); Lack, N. Engl. J. Med. 359:1252 (2008)). Examples of known food allergens include peanuts, tree nuts, fish, and shellfish are common allergens in both children and adults, while children also often react to eggs, wheat, and soy.

Food-induced allergic reactions result from immunologic pathways that include activation of effector cells through food specific IgE antibodies, cell-mediated (non-IgE-mediated) reactions resulting in subacute or chronic inflammation, or the combination of these pathways. The significance of IgE-mediated arm of reactions in human was demonstrated by anti-IgE therapy in patients with peanut allergy, which significantly and substantially increased the threshold of sensitivity to peanut on oral food challenge (Leung et al., N. Engl. J. Med. 348:986 (2003)). Furthermore, histamine has been reported to increase in food allergy patients after allergen challenge (Sampson and Jolie, N. Engl. J. Med. 311:372 (1984)), suggesting involvement of mast cell or basophil activation downstream of IgE-mediated pathways. On the other hand, celiac disease, which is a representative of the cell-mediated arm of food hypersensitivity, is mediated by gluten-reactive T cells, and the symptoms are confined to gut, often mild and chronic (Sollid and Lundin, Mucosal Immunol. 2:3 (2009)).

Consequently, methods of the invention include modulating (e.g., decrease, reduce, inhibit, suppress, limit or control) immunologic pathways that include activation of effector cells through food specific IgE antibodies, cell-mediated (non-IgE-mediated) reactions resulting in subacute or chronic inflammation, or a combination of these pathways. Methods of the invention also include modulating (e.g., decrease, reduce, inhibit, suppress, limit or control) IgE-mediated reactions thereby treating, inhibiting, reducing or decreasing sensitivity to food allergies. Methods of the invention further include modulating (e.g., decrease, reduce, inhibit, suppress, limit or control) histamine release or activation of downstream IgE-mediated pathways, such as by, but not limited to, mast cells or basophils.

As disclosed herein, animal models indicate that food allergy may be elicited by classic or alternative pathways, both of which appear to depend on immunoglobulins (Igs). Methods of the invention therefore also include modulating (e.g., decrease, reduce, inhibit, suppress, limit or control) either or both pathways that appear to contribute to food allergy. Such methods include, for example, modulating (e.g., decrease, reduce, inhibit, suppress, limit or control) B cells or mast cells, or release of histamine and platelet activating factor (PAF), which is believed to cause anaphylactic symptoms. Such methods also include, for example, modulating (e.g., decrease, reduce, inhibit, suppress, limit or control) hypothermia.

As also disclosed herein, animal models indicate that the Ig/mast cell axis plays a role in food allergy. The food-induced anaphylaxis and diarrhea models reveal the role of B cells and mast cells, and a contributory role of FcεRI, suggesting a central role of Ig/mast cell interaction in the effecter phase of food allergy. As disclosed herein, a subset of IgE and IgG molecules have been identified as HRF receptors, and the HRF reactivity of Igs could modulate the effecter phase of food allergy.

Methods of the invention therefore also include modulating numbers or activity of mast cells or B cells in the small intestine, such as in the jejunum, or in the colon (large intestine). Such methods include, for example, decreasing, reducing, inhibiting, suppressing, limiting or controlling numbers or activity of mast cells or B cells in the small intestine, such as in the jejunum. Such methods also include, for example, inhibiting, reducing or decreasing numbers or activity of mast cells or B cells in the colon (large intestine). Such methods further include treating diarrhea.

As further disclosed herein, food allergy is prevalent in patients with eosinophilic esophagitis (EoE), and HRF appears to play a role in food allergy or the underlying eosinophilic esophagitis (EoE). HRF therefore plays a role in food allergy and EoE.

Methods of the invention are therefore applicable to treatment of food allergy in subjects with eosinophilic esophagitis (EoE). Methods of the invention therefore include treatment (e.g., decrease, reduce, inhibit, suppress, limit or control) of one or more symptoms, such as vomiting, abdominal pain, or failure to thrive, for example, in young children, or, for example, dysphagia in adolescents or adults. Methods of the invention also include treatment (e.g., decrease, reduce, inhibit, suppress, limit or control) of esophageal stricture formation and tissue remodeling. Methods of the invention further include treatment of (e.g., decrease, reduce, inhibit, suppress, limit or control) esophageal dysmotility in a subject, such as in an adult or pediatric EoE subject. Methods of the invention additionally include treatment of (e.g., decrease, reduce, inhibit, suppress, limit or control) local IgE production and systemic sensitization that occur in EoE. Methods of the invention moreover include treatment (e.g., decrease, reduce, inhibit, suppress, limit or control) of delayed type hypersensitivity and esophageal mastocytosis, such as in patients suffering from EoE (Kirsh et al., J. Pediatric Gastroenterol. Nutrition 44:20 (2007)).

The term "contacting" means direct or indirect binding or interaction between two or more entities (e.g., between an HRF sequence and native endogenous HRF, or between an antibody and endogenous HRF). A particular example of direct interaction is binding. A particular example of an indirect interaction is where one entity acts upon an intermediary molecule, which in turn acts upon the second referenced entity. Thus, for example, contacting HRF with an antibody includes allowing the antibody to bind to HRF, or allowing the antibody to act upon an intermediary that in turn binds to HRF. Contacting as used herein includes in solution, in solid phase, in vitro, ex vivo, in a cell and in vivo. Contacting in vivo can be referred to as administering, or administration.

In accordance with the invention, there are provided methods of treating an allergic reaction, hypersensitivity, an inflammatory response or inflammation. In one embodiment, a method includes contacting histamine releasing factor (HRF)/translationally controlled tumor protein (TCTP) with a compound that inhibits or reduces binding of HRF/TCTP to an immunoglobulin thereby treating the allergic reaction, hypersensitivity, inflammatory response or inflammation.

In accordance with the invention, there are also provided methods for decreasing, reducing, inhibiting, suppressing, limiting or controlling the probability, severity, frequency, duration or preventing a subject from having an acute or chronic food allergy, allergic reaction, hypersensitivity, an inflammatory response or inflammation. In one embodiment, a method includes administering to a subject a compound that decreases, reduces, inhibits, suppresses, limits or controls binding of HRF/TCTP to an immunoglobulin thereby decreasing, reducing, inhibiting, suppressing, limiting or controlling the probability, severity, frequency, duration or preventing the subject from having an acute or chronic food allergy, allergic reaction, hypersensitivity, inflammatory response or inflammation.

Methods of the invention include modulating (e.g., decrease, reduce, inhibit, suppress, limit or control) one or more functions, activities or expression of HRF, in vitro, ex vivo or in vivo. As used herein, the term "modulate," means an alteration or effect of the term modified. For example, the term modulate can be used in various contexts to refer to an alteration or effect of an activity, a function, or expression of a polypeptide, gene or signaling pathway, or a physiological condition or response of an organism. Thus, where the term "modulate" is used to modify the term "HRF" this means that an HRF activity, function, or expression is altered or affected (e.g., decreased, reduced, inhibited, suppressed, limited, controlled or prevented, etc.) Detecting an alteration or an effect on HRF activity, function or expression can be determined as set forth herein using in vitro assays or an animal model.

Compounds useful in practicing the methods of the invention include peptides and polypeptides, such as HRF sequences, HRF subsequences or fragments (e.g., a sequence that binds to an Ig, such as an IgE), antibodies and antibody subsequences (e.g., polyclonal or monoclonal and any of IgM, IgG, IgA, IgD or IgE isotypes) known to the skilled artisan and as set forth herein. Such sequences can be mammalian, humanized, human or chimeric.

Particular examples include a fragment of HRF/TCTP polypeptide that binds to an immunoglobulin, such as an IgE. An exemplary HRF sequence includes or consists of amino acids 1-19 or amino acids 79-142 of a mammalian HRH/TCTP sequence, for example, all or a portion of a MIIYRDLISHDEMFSDIYK (SEQ ID NO:1) sequence, or all or a portion of a QETSFTKEAYKKYIKDYMKSIK-GKLEEQRPERVKPFMTGAAEQIKHILANFKNYQ FFI-GENMNP (SEQ ID NO:2) sequence.

Particular non-limiting examples of HRF binding antibodies include commercial antibodies from Santa Cruz Biotechnology, Inc. (Santa Cruz, Calif.), as set forth in Table 2 below:

TABLE 2

| HRF (B-3) Antibody sc-133131 | mouse IgG$_1$ | 1-172 (h) |
| HRF (FL-172) Antibody sc-30124 | rabbit IgG | FL (h) |
| HRF (L-20) Antibody sc-20427 | goat IgG | internal (h) |
| HRF (N-20) Antibody sc-20426 | goat IgG | N-terminus (h) |
| HRF (23-Y) Antibody sc-100763 | mouse IgG$_1$ | FL (h) |
| HRF (20) Antibody sc-135940 | mouse IgG$_1$ | N/A |

Additional particular non-limiting examples of HRF binding antibodies include commercial antibodies from Assay Designs/Stressgen (Ann Arbor, Mich.), Proteintech Group (Chicago, Ill.), R and D Systems, Inc. (Minneapolis, Minn.), Sigma-Aldrich Corp. (St. Louis, Mo.), AbDSerotec/MorphoSys UK Ltd. (Oxford, UK), Strategic Diagnostics (SDIX) (Newark, Del.), Abcam (Cambridge, Mass.) and Novus Biologicals, LLC (Littleton, Colo.) as set forth in Table 3 below:

TABLE 3

Tumor protein (TPT1) Monoclonal Antibody (3C7), Assay Designs/Stressgen, reactivity: human; clonality: monoclonal; host: mouse
TPT1, Proteintech Group, reactivity: human; clonality: polyclonal; host: rabbit
Human/Mouse/Rat TPT1/TCTP MAb (Clone 488411), R& D Systems, reactivity: human; clonality: monoclonal; host: mouse
Monoclonal Anti-TPT1 antibody produced in mouse, Sigma-Aldrich, reactivity: human; clonality: monoclonal; host: mouse
Mouse anti-human TPT1: Azide Free, AbDSerotec, reactivity: human; clonality: monoclonal; host: mouse
TPT1 antibody, Strategic Diagnostics, reactivity: human; clonality: polyclonal; host: rabbit
TCTP antibody, Abcam, reactivity: human, rat, mouse; clonality: polyclonal; host: rabbit
TCTP antibody, Abcam, reactivity: human; clonality: monoclonal; host: mouse
TCTP antibody, Abcam, reactivity: human; clonality: monoclonal; host: mouse
TCTP Antibody, Novus Biologicals, reactivity: human, rat; clonality: polyclonal; host: rabbit
TCTP Antibody (3C7), Novus Biologicals, reactivity: human; clonality: monoclonal; host: mouse
TCTP Antibody (2C4), Novus Biologicals, reactivity: human; clonality: monoclonal; host: mouse The condition treated in accordance with the methods can be chronic or acute. For example the food allergy, allergic reaction, hypersensitivity, inflammatory response, inflammation, or airway constriction can be chronic or acute.

Methods (e.g., treatment) according to the invention can result in a reduction in occurrence, frequency, severity, progression, or duration of a symptom of the condition. For example, methods of the invention can protect against or decrease, reduce, inhibit, suppress, limit or control progression, severity, frequency, duration or probability of an adverse symptom of the food allergy, allergic reaction, hypersensitivity, inflammatory response or inflammation.

In particular embodiments, treatment according to a method of the invention is sufficient to protect against or decrease, reduce, inhibit, suppress, limit or control the food allergy, allergic reaction, hypersensitivity, inflammatory response or inflammation, decrease, reduce, inhibit, suppress, limit or control susceptibility to the food allergy, allergic reaction or hypersensitivity, or decrease, reduce, inhibit, suppress, limit or control a food allergy, allergic reaction, hypersensitivity, inflammatory response or inflammation.

In additional particular embodiments, treatment according to a method of the invention is sufficient to decrease, reduce, inhibit, suppress, limit, control or improve the probability, severity, frequency, or duration of one or more adverse symptoms, disorders, illnesses, pathologies, diseases, or complications caused by or associated with the food allergy, allergic reaction, hypersensitivity, inflammatory response or inflammation.

Exemplary symptoms include one or more of diarrhea, bloat, swelling, pain, rash, headache, fever, nausea, lethargy, airway constriction, skeletal joint stiffness, or tissue or cell damage. Exemplary symptoms also include tissue, organ or cellular damage or remodeling. Exemplary tissues and organs that can exhibit damage include epidermal or mucosal tissue, gut, bowel, pancreas, thymus, liver, kidney, spleen, skin, eye, or a skeletal joint (e.g., knee, ankle, hip, shoulder, wrist, finger, toe, or elbow), and airway. Treatment can result in decreasing, reducing, inhibiting, suppressing, limiting, controlling or preventing progression or worsening of tissue, organ or cellular damage or remodeling.

Methods of the invention that include treatment include protecting against or decreasing, reducing, inhibiting, suppressing, limiting or controlling occurrence, progression, severity, frequency or duration of a symptom or characteristic of the condition treated. At the whole body, regional or local level, a symptom of an inflammatory response or inflammation is generally characterized by swelling, pain, headache, fever, nausea, skeletal joint stiffness or lack of mobility, rash, redness or other discoloration. At the whole body level, an adverse symptom can also include shortness of breath (dyspnea), wheezing, stridor, coughing, airway remodeling, rapid breathing (tachypnea), prolonged expiration, runny nose, rapid or increased heart rate (tachycardia), rhonchous lung, lung or airway constriction, over-inflation of the chest or chest-tightness, decreased lung capacity, an acute asthmatic episode, lung, airway or respiratory mucosum inflammation, or lung, airway or respiratory mucosum tissue damage.

At the cellular level, a symptom of an inflammatory response or inflammation is characterized by one or more of cell infiltration of the region, production of antibodies, production of cytokines, lymphokines, chemokines, interferons and interleukins, cell growth and maturation factors (e.g., differentiation factors), cell proliferation, cell differentiation, cell accumulation or migration and cell, tissue or organ damage or remodeling. Thus, treatment according to a method of the invention can protect against or decrease, reduce, inhibit, suppress, limit or control occurrence, progression, severity, frequency or duration of any one or more of such symptoms or characteristics of the condition.

Allergic reactions in which treatment according to a method of the invention can protect against or decrease, reduce, inhibit, suppress, limit or control include bronchial asthma (extrinsic or intrinsic); Allergic rhinitis; Onchocercal dermatitis; Atopic dermatitis; allergic conjunctivitis; Drug reactions; Nodules, eosinophilia, rheumatism, dermatitis, and swelling (NERDS); Esophageal and a gastrointestinal allergy (e.g., a food allergy).

Conditions in which treatment according to a method of the invention can protect against or decrease, reduce, inhibit, suppress, limit or control include hypersensitivity, inflammatory response or inflammation of a respiratory disease or disorder. Such disorders can affect the skin, or upper or lower respiratory tract, and include, for example, asthma, allergic asthma, bronchiolitis and pleuritis, as well as Airway Obstruction, Apnea, Asbestosis, Atelectasis, Berylliosis, Bronchiectasis, Bronchiolitis, Bronchiolitis Obliterans Organizing Pneumonia, Bronchitis, Bronchopulmonary Dysplasia, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Rhinoscleroma, Scimitar Syndrome, Severe Acute Respiratory Syndrome, Silicosis, Tracheal Stenosis, eosinophilic pleural effusions, Histiocytosis; chronic eosinophilic pneumonia; hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease (COPD); Interstitial Lung Disease; and Topical eosinophilia.

In accordance with the invention, there are also provided methods for increasing, enhancing or stimulating airway-dilation, and for reducing or inhibiting airway-constriction. In one embodiment, a method includes administering to a subject in need of increasing airway-dilation an amount of a compound that inhibits or reduces binding of HRF/TCTP to an immunoglobulin sufficient to increase, enhance or stimulate airway-dilation in the subject. In another embodiment, a method includes administering to a subject in need thereof an amount of a compound that inhibits or reduces binding of HRF/TCTP to an immunoglobulin sufficient to reduce or inhibit airway-constriction in the subject.

In methods of the invention, a compound can be administered prior to, substantially contemporaneously with or following one or more adverse symptoms, disorders, illnesses, pathologies, diseases, or complications caused by or associated with development of or manifestation of an acute or chronic symptom, for example, a food allergy, allergic reaction, hypersensitivity, inflammatory response or inflammation. In methods of the invention, a compound can be administered prior to, substantially contemporaneously with or following administering a second drug or treatment.

Non-limiting examples of classes of second drugs or treatments include an anti-food allergy, anti-allergic reaction, anti-hypersensitivity, anti-inflammatory, anti-asthmatic or anti-allergy drug. More particular examples of a second drug include a hormone, a steroid, an anti-histamine, anti-leukotriene, anti-IgE, anti-$\alpha$4 integrin, anti-$\beta$2 integrin, anti-CCR3 antagonist, $\beta$2 agonist or an anti-selectin.

Methods of the invention may be practiced prior to (i.e. prophylaxis), concurrently with or after evidence of the disorder, disease or condition beginning (e.g., one or more symptoms). Administering a composition prior to, concurrently with or immediately following development of a symptom may decrease, reduce, inhibit, suppress, limit or control the occurrence, frequency, severity, progression, or duration of one or more adverse symptoms, disorders, illnesses, pathologies, diseases, or complications caused by or associated with the food allergy, allergic reaction, hypersensitivity, inflammatory response or inflammation in the subject. In addition, administering a composition prior to, concurrently with or immediately following development of one or more symptoms may decrease, reduce, inhibit, suppress, limit, control or prevent damage to cells, tissues or organs that occurs, for example, due to one or more adverse symptoms, disorders, illnesses, pathologies, diseases, or complications caused by or associated with a food allergy, allergic reaction, hypersensitivity, inflammatory response or inflammation.

Compositions and the methods of the invention, such as treatment methods, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, or one or more adverse symptoms, disorders, illnesses, pathologies, diseases, or complications caused by or associated with the food allergy, allergic reaction, hypersensitivity, inflammatory response or inflammation. Therapeutic benefits and improvements include, but are not limited to, decreasing, reducing, inhibiting, suppressing, limiting or controlling the occurrence, frequency, severity, progression, or duration of one or more symptoms or complications associated with disorders, illnesses, pathologies, diseases, or complications caused by or associated with the food allergy, allergic reaction, hypersensitivity, inflammatory response or inflammation. Compositions and methods of the invention therefore include providing a therapeutic benefit or improvement to a subject.

In the methods of the invention in which a therapeutic benefit or improvement is a desired outcome, a composition of the invention such as an HRF polypeptide or an antibody that binds to HRF, can be administered in a sufficient or effective amount to a subject in need thereof. An "amount sufficient" or "amount effective" refers to an amount that provides, in single or multiple doses, alone or in combination, with one or more other compositions (therapeutic agents such as a drug), treatments, protocols, or therapeutic regimens agents, a detectable response of any duration of time (long or short term), an expected desired outcome in or a benefit to a subject of any measurable or detectable degree or for any duration of time (e.g., for minutes, hours, days, months, years, or cured). For example, a sufficient amount of an HRF sequence, or an antibody or subsequence that binds to HRF, is considered as having a therapeutic effect if administration results in a decreased or reduced amount or frequency of immunotherapy being required for treatment of a one or more adverse symptoms, disorders, illnesses, pathologies, diseases, or complications caused by or associated with the food allergy, allergic reaction, hypersensitivity, inflammatory response or inflammation.

The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, one or more adverse symptoms, disorders, illnesses, pathologies, diseases, or complications, for example, caused by or associated with the food allergy, allergic reaction, hypersensitivity, inflammatory response or inflammation to a measurable extent, although decreasing, reducing, inhibiting, suppressing, limiting or controlling a progression or worsening of the disorder, disease or condition or a symptom, is a satisfactory outcome.

The term "ameliorate" means a detectable improvement in a subject's condition. A detectable improvement includes a subjective or objective decrease, reduction, inhibition, suppression, limit or control in the occurrence, frequency, severity, progression, or duration of a symptom caused by or associated with a disorder, disease or condition, such as one or more adverse symptoms, disorders, illnesses, pathologies, diseases, or complications caused by or associated with the food allergy, allergic reaction, hypersensitivity, inflammatory response or inflammation, or an improvement in an underlying cause or a consequence of the disorder, disease or condition, or a reversal of the disorder, disease or condition.

Treatment can therefore result in decreasing, reducing, inhibiting, suppressing, limiting, controlling or preventing a disorder, disease or condition, or an associated symptom or consequence, or underlying cause; decreasing, reducing, inhibiting, suppressing, limiting, controlling or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" of decreasing, reducing, inhibiting, suppressing, limiting, controlling or preventing the occurrence, frequency, severity, progression, or duration of one or more symptoms or underlying causes or consequences of a condition, disorder, disease or symptom in the subject, such as one or more adverse symptoms, disorders, illnesses, pathologies, diseases, or complications caused by or associated with a food allergy, allergic reaction, hypersensitivity, inflammatory response or inflammation. Treatment methods affecting one or more underlying causes of the condition, disorder, disease or symptom are therefore considered to be beneficial. Stabilizing a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial decrease, reduction, inhibition, suppression, limit, control or prevention in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, such as one or more adverse symptoms, disorders, illnesses, pathologies, diseases, or complications caused by or associated with the food allergy, allergic reaction, hypersensitivity, inflammatory response or inflammation, over a short or long duration of time (hours, days, weeks, months, etc.).

An amount sufficient or an amount effective can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., agent), treatment, protocol or therapeutic regimen, since additional doses, amounts or duration above and beyond such doses, or additional compositions (e.g., agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, or a majority of treated subjects in a given group or population. An amount sufficient or an amount effective means sufficiency or effectiveness in a particular subject, not a group or the general population. As is typical for such methods, some subjects will exhibit a greater response, or less or no response to a treatment method.

Additional examples of a therapeutic benefit for one or more adverse symptoms, disorders, illnesses, pathologies, diseases, or complications caused by or associated with the food allergy, allergic reaction, hypersensitivity, inflammatory response or inflammation is an improvement in one or more such symptoms. For example, decreasing, reducing, inhibiting, suppressing, limiting, controlling or preventing further or reducing an allergic reaction, food allergy, lung or airway constriction or remodeling, tissue or organ infiltration or tissue destruction, or pancreas, thymus, kidney, liver, spleen, eye, epidermal (skin) or mucosal tissue, gut or bowel infiltration or tissue destruction or remodeling.

Particular non-limiting examples of therapeutic benefit or improvement for a pathogen include decreasing, reducing, inhibiting, suppressing, limiting, controlling or preventing occurrence, frequency, severity, progression, or duration of one or more symptoms or complications of a food allergy, allergic reaction, hypersensitivity, inflammatory response or inflammation. Additional particular non-limiting examples of therapeutic benefit or improvement include stabilizing the condition (i.e., decreasing, reducing, inhibiting, suppressing, limiting, controlling or preventing a worsening or progression of a symptom or complication associated with a food allergy, allergic reaction, hypersensitivity, inflammatory response or inflammation). Symptoms or complications associated with a food allergy, allergic reaction, hypersensitivity, inflammatory response or inflammation whose occurrence, frequency, severity, progression, or duration can be decreased, reduced, inhibited, suppressed, limited, controlled or prevented are known in the art. A therapeutic benefit can also include reducing susceptibility of a subject to one or more adverse symptoms, disorders, illnesses, pathologies, diseases, or complications caused by or associated with a food allergy, allergic reaction, hypersensitivity, inflammatory response or inflammation or hastening or accelerating recovery from one or more adverse symptoms, disorders, illnesses, pathologies, diseases, or complications caused by or associated with a food allergy, allergic reaction, hypersensitivity, inflammatory response or inflammation.

As is typical for treatment or therapeutic methods, some subjects will exhibit greater or less response to a given treatment, therapeutic regiment or protocol. Thus, appropriate amounts will depend upon the condition treated (e.g., the type or stage of the tumor), the therapeutic effect desired, as well as the individual subject (e.g., the bioavailability within the subject, gender, age, etc.).

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of food allergy, allergic reaction, hypersensitivity, inflammatory response or inflammation, for studying in vivo a composition of the invention, for example, an HRF sequence or an antibody that binds to HRF.

Subjects appropriate for treatment include those having or at risk of having an undesirable or aberrant immune response, immune disorder or immune disease, those undergoing treatment for an undesirable or aberrant immune response, immune disorder or immune disease as well as those who are undergoing or have undergone treatment or therapy for an undesirable or aberrant immune response, immune disorder or immune disease, including subjects where the undesirable or aberrant immune response, immune disorder or immune disease is in remission. Specific non-limiting examples include subjects having or at risk of having one or more adverse symptoms, disorders, illnesses, pathologies, diseases, or complications caused by or associated with a food allergy, allergic reaction, hypersensitivity, inflammatory response or inflammation.

"At risk" subjects typically have risk factors associated with undesirable or aberrant immune response, immune disorder or immune disease, such as a food allergy, allergic reaction, hypersensitivity, inflammatory response or inflammation. Risk factors include gender, lifestyle (diet, smoking), occupation (medical and clinical personnel, agricultural and livestock workers), environmental factors (allergen exposure), family history (e.g., genetic predisposition), etc.

Compositions and methods of the invention may be contacted or provided in vitro, ex vivo or administered in vivo. Compositions can be administered to provide the intended effect as a single or multiple dosages, for example, in an effective or sufficient amount. Exemplary doses range from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 mg/kg, on consecutive days, alternating days or intermittently.

Single or multiple doses can be administered on the same or consecutive days, alternating days or intermittently. For example, a compound such as an HRF sequence or antibody that binds to HRF can be administered one, two, three, four or more times daily, on alternating days, bi-weekly, weekly, monthly, bi-monthly, or annually.

Compounds can be administered to a subject and methods may be practiced substantially contemporaneously with, or within about 1-60 minutes, hours, or days of the onset of an adverse symptom associated with a food allergy, allergic reaction, hypersensitivity, inflammatory response or inflammation.

Compounds can be administered and methods may be practiced via systemic, regional or local administration, by any route. For example, an HRF sequence or an antibody that binds to HRF may be administered systemically, regionally or locally, via ingestion, via inhalation, topically, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods of the invention including pharmaceutical formulations can be administered via a (micro)encapsulated delivery system or packaged into an implant for administration.

Invention compositions and methods include pharmaceutical compositions, which refer to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin, can prolong absorption of injectable compositions.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays, inhalation devices (e.g., aspirators) or suppositories. For transdermal administration, the active compounds are formulated into ointments, salves, gels, creams or patches.

Additional pharmaceutical formulations and delivery systems are known in the art and are applicable in the methods of the invention (see, e.g., *Remington's Pharmaceutical Sciences* (1990) 18th ed., Mack Publishing Co., Easton, Pa.; The Merck Index (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

The compositions used in accordance with the invention, including proteins (HRF sequences, antibodies), nucleic acid (e.g., inhibitory), treatments, therapies, agents, drugs and pharmaceutical formulations can be packaged in dosage unit form for ease of administration and uniformity of dosage. "Dosage unit form" as used herein refers to physically discrete units suited as unitary dosages treatment; each unit contains a quantity of the composition in association with the carrier, excipient, diluent, or vehicle calculated to produce the desired treatment or therapeutic (e.g., beneficial) effect. The unit dosage forms will depend on a variety of factors including, but not necessarily limited to, the particular composition employed, the effect to be achieved, and the pharmacodynamics and pharmacogenomics of the subject to be treated.

The invention provides cell-free (e.g., in solution, in solid phase) and cell-based (e.g., in vitro or in vivo) methods of screening, detecting and identifying HRF. The methods can be performed in solution, in vitro using a biological material or sample, and in vivo, for example, using a fluid or lavage sample from an animal.

In accordance with the invention, there are provided methods of diagnosing a subject having or at risk of a food allergy. In one embodiment, a method includes measuring histamine releasing factor (HRF)/translationally controlled tumor protein (TCTP) in a sample from a subject, wherein an amount of HRF/TCTP in the sample greater than normal diagnoses the subject as having or at risk of a food allergy.

In one aspect, HRF measuring includes determining the amount of HRF/TCTP protein or nucleic acid encoding HRF/TCTP (RNA, cDNA) in the sample. In another aspect, HRF measuring includes contacting the sample with an agent or tag (e.g., a detectable agent or tag, such as an antibody, protein or nucleic acid that binds to HRF/TCTP protein or nucleic acid encoding HRF/TCTP) that binds to HRF/TCTP protein or nucleic acid encoding HRF/TCTP and ascertaining the amount of HRF/TCTP protein or nucleic acid encoding HRF/TCTP, or the amount of agent or tag (e.g., a detectable agent or tag, such as an antibody, protein or nucleic acid that binds to HRF/TCTP protein or nucleic acid encoding HRF/TCTP) bound to the HRF/TCTP protein or nucleic acid encoding HRF/TCTP.

The invention also provides cell-free (e.g., in solution, in solid phase) and cell-based (e.g., in vitro or in vivo) methods of diagnosing and monitoring progression of a subject having or at increased risk of having a food allergy, allergic reaction, hypersensitivity, inflammatory response, or inflammation, the location, presence or extent of a food allergy, allergic reaction, hypersensitivity, inflammatory response, or inflammation, as well as identifying a subject appropriated for treatment with an HRF sequence, or an antibody that binds to HRF, due to increased probability of responding to treatment. The methods can be performed in solution, in vitro using a biological material or sample, for example, a sample or biopsy of cells, tissue or organ. The methods can also be performed in vivo, for example, in an animal.

In one embodiment, a method includes contacting a biological material or sample (e.g., from a subject) with an HRF sequence, or an antibody that binds to HRF; and assaying for the presence of HRF. The binding to HRF can be used to ascertain the presence or amount of HRF, which can be correlated with increased risk of having a food allergy, allergic reaction, hypersensitivity, inflammatory response, or inflammation, thereby diagnosing the subject. The presence or amount of HRF can also identify a subject appropriate for an anti-HRF treatment, as such subjects will have a greater probability of favorably responding to treatment of a food allergy, allergic reaction, hypersensitivity, inflammatory response, or inflammation, for example, treatment with an HRF sequence (HRF polypeptide or inhibitory nucleic acid) or an anti-HRF antibody. In one aspect, a biological material or sample is obtained from a mammal (e.g., a human) Methods of monitoring progression of a food allergy, allergic reaction, hypersensitivity, inflammatory response, or inflammation can be performed at a regular or irregular intervals, for example, daily, bi-weekly, weekly, bi-monthly, monthly, quarterly, semi- or bi-annually, annually, etc., as appropriate.

Diagnostic methods can be performed on any subject, such as a mammal (e.g., human, primate). Such subjects can have or be at risk of having a condition or disorder associated with HRF activity, function, or expression as set forth herein. For example, a subject can have or be at risk of having a food allergy, allergic reaction, hypersensitivity, inflammatory response or inflammation.

The terms "assaying" and "measuring" and grammatical variations thereof are used interchangeably herein and refer to either qualitative or quantitative determinations, or both qualitative and quantitative determinations. When the terms are used in reference to binding or detection, any means of assessing the relative amount, affinity or specificity of binding is contemplated, including the various methods set forth herein and known in the art. For example, HRF binding can be assayed or measured by an ELISA assay, Western blot or immunoprecipitation assay, or by modulating an activity, function or expression of a native HRF. In another example, antibody binding can be assayed or measured by an ELISA assay, Western blot or immunoprecipitation assay.

The term "correlating" and grammatical variations thereof refers to a relationship or link between two or more entities. For example, as disclosed herein HRF is associated with, among other things, food allergy, allergic reaction, hypersensitivity, inflammatory response or inflammation. Thus, because of this relationship between HRF and a food allergy, allergic reaction, hypersensitivity, inflammatory response or inflammation they correlate with each other. Thus, correlating the presence or quantity of HRF can indicate susceptibility, or the presence and/or extent, or severity of a food allergy, allergic reaction, hypersensitivity, inflammatory response or inflammation in a subject, for example.

In accordance with the invention, there are provided methods of identifying an agent that reduces or inhibits a food allergy, allergic reaction, hypersensitivity, inflammatory response or inflammation. In one embodiment, a method includes contacting histamine releasing factor (HRF)/translationally controlled tumor protein (TCTP) with a test compound in the presence of an immunoglobulin that binds to HRF/TCTP; and determining if the compound inhibits or reduces binding of HRF/TCTP to the immunoglobulin. A reduction or inhibition of binding identifies the test compound as an agent that reduces or inhibits a food allergy, allergic reaction, hypersensitivity, inflammatory response or inflammation. In particular aspects, an immunoglobulin is an IgE, IgG, IgA, IgM or IgD.

The invention provides kits including compositions of the invention (e.g., HRF polypeptides, antibodies that bind to HRF, nucleic acids encoding HRF sequences or hybridizing sequences, etc.), combination compositions and pharmaceutical formulations thereof, packaged into suitable packaging material. Kits can be used in various methods. For example, a kit can determine an anti-N19 antibody or an anti-HRF antibody that recognizes epitopes outside the N19 portion, since anti-N19 antibody is believed to inhibit HRF/Ig interactions, but the latter anti-HRF antibody might not have the same activity. If so, the ratio of anti-N-19 over anti-HRF (outside of N19) in blood or other body fluids would indicate a contribution of HRF/Ig interaction to the disease.

A kit typically includes a label or packaging insert including a description of the components or instructions for use in vitro, in vivo, or ex vivo, of the components therein. A kit can contain a collection of such components, e.g., HRF sequence, antibody that binds to HRF, alone, or in combination with another therapeutically useful composition (e.g., an immune modulatory drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include, instructions for treating an undesirable or aberrant immune response, immune disorder, immune disease, such as a food allergy, allergic reaction, hypersensitivity, inflammatory response or inflammation. Kits of the invention therefore can additionally include labels or instructions for practicing any of the methods of the invention described herein including treatment, or diagnostic methods.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain host cells expressing peptides or antibodies of the invention, or that contain encoding nucleic acids. The cells in the kit can be maintained under appropriate storage conditions until the cells are ready to be used. For example, a kit including one or more cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "an HRF sequence" or an "HRF binding antibody" includes a plurality of such HRF sequences or antibodies or subsequences thereof, and reference to "an HRF activity or function" can include reference to one or more HRF activities or functions, and so forth.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges include integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and any numerical range within such a ranges, such as 1-2, 5-10, 10-50, 50-100, 100-500, 100-1000, 500-1000, 1000-2000, 1000-5000, etc. In a further example, reference to a range of $K_D$ $10^{-5}$ M to about $K_D$ $10^{-13}$ M includes any numerical value or range within or encompassing such values, such as $1 \times 10^{-5}$ M, $1 \times M10^{-6}$ M, $1 \times 10^{-7}$ M, $1 \times 10^{-8}$ M, etc.

As also used herein a series of range formats are used throughout this document. The use of a series of ranges includes combinations of the upper and lower ranges to provide a range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, and 150-171, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-171, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example includes a description of various materials and methods.

Mice

C57BL/6 and Balb/c mice were purchased from the Jackson Laboratory (Maine). FcεRIα$^{-/-}$ mice (Dombrowicz et al., *Cell* 75:969 (1993)) on a Balb/c background, FcεRIγ$^{-/-}$ mice (Takai et al., *Cell* 76:519 (1994)) on a C57BL/6 background, µMT mice (Kitamura et al., *Nature* 350:6317 (1991)) on a C57BL/6 background, and Kit$^{W-sh/W-sh}$ mice (Grimbaldeston et al., *Am. J. Pathol.* 167:835 (2005)) on a C57BL/6 background. Such knockout mice are usually backcrossed to Balb/c or C57BL/6 mice for >10 generations.

Purification and Preparation of IgE and IgG

For purification of IgE, Ishizaka's method (Ishizaka, Methods Enzymol. 116:76 (1985)) was utilized such that IgE was enriched from ascites or culture supernatants by ammonium sulfate precipitation (40-55%). IgE-containing fractions were then purified by DEAE-agarose (GE Healthcare Bio-Sciences AB) column chromatography, followed by gel filtration using Sephacryl S-300 (GE). IgG molecules were first precipitated by 50% ammonium sulfate solution and then purified by protein G column (GE) chromatography, followed by gel filtration using Sephacryl S-300. The IgE and IgG preparations were dialyzed against PBS and ultracentrifuged to remove aggregates before use.

Anti-DNP mouse IgE mAbs (DNP H1-ε-26, DNP H1-ε-206) were provided by Dr. Fu-Tong Liu, University of California, Davis; anti-OVA mouse IgE (αOE) by Dr. Erwin W. Gelfand, National Jewish Medical and Research Center. IgE mAbs or anti-OVA mouse IgE are also available from Condrex, Inc., Redmond, Wash. Anti-TNP mouse IgE mAbs (C48-2 and C38-2) and anti-dansyl mouse IgE mAb (27-74) were purchased from BD Biosciences Pharmingen. Anti-DNP IgE mAb (SPE-7) was purchased from Sigma-Aldrich. IgG mAbs were provided by Stephen P. Shoenberger, LIAI, Rachel S. Soloff, Lilia Koriazova, and Manju Saxena, Kyowa Hakko Kirin Calif., or purchased from BD Pharmingen and eBiosciences. Human IgE molecules from a myeloma patient (IgEκ and IgEλ) were purchased from The Binding Site Inc. Human monoclonal IgE (HE1) was purchased from Diatec Monoclonals AS. Human IgE mAb (SKO-007) was purified from culture supernatants of hybridoma (American Type Culture Collection).

Preparation of Recombinant Mouse Histamine Releasing Factor (mHRF)

Complementary DNAs of full-length and truncated forms of mHRF were amplified by PCR using total RNA derived from BMMCs (mouse bone marrow-derived mast cells) as a template and the primers. After nucleotide sequences of the PCR products were confirmed, they were ligated into the pGEX-3T vector. GST-mHRF and truncated fusion proteins were expressed in *E. coli* DH5a and purified using glutathione-agarose (Sigma-Aldrich). The C-terminally His$_6$-tagged mHRF construct was generated by amplifying the cDNA of the full-length mHRF using the primers. The amplified cDNA was ligated into pET-24a(+) plasmid (Novagen) and mHRF-His$_6$ was expressed in *E. coli* BL21 (DE3) (Invitrogen). The mHRF-His$_6$ protein was purified using ProBond™ Nickel-Chelating Resin (Invitrogen). All recombinants were further purified by Sephacryl S-100 (GE) and extensively dialyzed against PBS.

Primers used were as follows:

```
Forward primers for GST fusion proteins
For N12, N19, N32, N47, N78, N142, N154 and full
length mouse HRF:
                                (SEQ ID NOs:11-12)
AAAAGGATCCATGATCATCTACCGGGACC For N79-142 and N79-172:
AAAAGGATCCCAAGAAACCAGCTTCACAAA Reverse primers for GST fusion proteins
For N12:
                                (SEQ ID NOs:13-21)
TTTGAATTCTTACTCGTCATGGCTGAT

N19:
AAAGAATTCTTACTTGTAGATGTCGGAGAACA

N32:
AAAGAATTCTTACTCCACCTCCAGGCACAGCC

N47:
AAAGAATTCTTAGAGCGAGTCATCGATGGCAC

N78:
AAAGAATTCTTATAAGTGATGGTTCATGACAA
```

-continued

N142 and N79-142:
AAAGAATTCTTATGGATTCATGTTTTCACCAA

Full length and N79-172:
AAAAGGATCCCAAGAAACCAGCTTCACAAA

Forward primer for His6-tagged mouse HRF:
AAAACATATGATCATCTACCGGGACCT

Reverse primer for His6-tagged mouse HRF:
TTTTCTCGAGACATTTCTCCATCTCTAAGC

ELISA

For detection of HRF-reactive mouse IgE and IgG, 96-well ELISA plates (PRO-BIND™ Flat Bottom from BD Labware) were coated with GST, GST-mHRF or mHRF-His$_6$ (each at 10 µg/ml in 0.1 M carbonate buffer (pH 9.5)). The next day, the plates were washed and blocked with 10% FCS or 1% BSA. Then, mouse IgE and IgG molecules (10 µg/ml), plasma (1/100 dilution) and BAL fluids (1/10 dilution) were incubated in the coated wells. Bound IgE was detected by incubation with biotinylated anti-mouse IgE (Pharmingen), followed with HRP-conjugated streptavidin (BD Pharmingen). Bound IgG was detected by incubation with HRP-conjugated anti-mouse IgG (GE). Color was developed using TMB substrate (BD Biosciences) and absorbance at $OD_{450}$ was measured. For detection of HRF-reactive human IgE molecules, biotinylated anti-human IgE mAb (Pharmingen) was used in place of biotinylated anti-mouse IgE mAb.

For OVA-specific IgG detection, OVA (10 µg/ml; Sigma-Aldrich) was coated onto 96-well ELISA plates overnight. BAL fluids (1/100 dilution) and plasma (1/1000 dilution) were incubated, and bound IgG molecules were detected by incubation with HRP-conjugated anti-mouse IgG. The absorbance at 450 nm was measured after color was developed.

IL-5 and IL-13 were measured by ELISA kits purchased from BD Biosciences and R&D Systems, respectively.

Mast Cells

Bone marrow cells from mouse femurs were cultured in IL-3-containing medium for 4 to 6 weeks to generate bone marrow mast cells (BMMCs). Purity of mast cells (≥95%) was checked by flow cytometry (c-Kit$^+$ FcεRI$^+$). For purification of peritoneal mast cells, peritoneal cells were first collected by lavage with 1 ml PBS. Then c-Kit$^+$ cells were purified by labeling with PE-conjugated anti-mouse CD117 mAb (StemCell Technologies Inc), followed by incubation with magnetic bead-conjugated anti-PE mAb (StemCell). The cells were separated using EasySep® magnet (StemCell).

GST Pull-Down Assay

IgE molecules were incubated with either GST or GST-mHRF bound onto glutathione-agarose beads overnight at 4° C. The beads were washed with PBS in the presence of 1% Triton-X and resuspended in SDS sample buffer, then, boiled. Samples were analyzed by SDS-PAGE, followed by immunoblotting using anti-GST (Santa Cruz Biotechnology) and anti-mouse IgE (Southern Biotechnology Associates, Inc.).

Flow Cytometric Analysis

For detection of the interaction between HRF and IgE molecules, BMMCs were first sensitized with 50 µg/ml IgE at 4° C. for 20 minutes, and then were incubated with mHRF-His$_6$ at 4° C. for 2 hours. Cell-bound mHRF was detected by incubation with rabbit anti-His Ab (Santa Cruz Biotechnology), followed with Alexa647-conjugated anti-rabbit IgG (Molecular Probe). FACSCalibur (BD Biosciences) was used for analysis.

Quartz Crystal Microbalance (QCM)

A QCM-based assay was performed as described previously (Ozeki et al., *Anal. Chem.* 79:79 (2007)). GST-mHRF or mHRF-His$_6$ was immobilized onto the chip and the immobilized chip was blocked with 1% BSA-PBS. Then, IgG molecules were injected and measured using Affinix Q$^4$ apparatus (Initium Co. Ltd.).

Degranulation

Mast cells were sensitized with 0.5 µg/ml IgE overnight. The mast cells were stimulated with TNP$_{26}$-BSA or mHRF-His$_6$ for 40 minutes in Tyrode's buffer. The amount of β-hexosaminidase (β-hex) in both supernatants and cell pellets was measured. The percentage of β-hex release was calculated as follows: % release=β-hex in supernatants/β-hex in supernatants+β-hex in cell pellets)

Passive Cutaneous Anaphylaxis

Mouse ears were first sensitized with 0.5 µg anti-TNP (C38-2 in the right ear and C48-2 in the left ear) IgE. After 24 hours, Evans' blue dye was intravenously (i.v.) injected, and TNP$_{26}$-BSA (Ag: 0.1 µg) or mHRF-His$_6$ (10 µg) were immediately injected into the ears. The acute (30 minute) reactions were analyzed by measurement of Evans' blue dye leakage. The ear thickness was measured using a micrometer (Mitutoyo) at 0.5, 1, 2, 4, 6, 8, 12, and 24 hours after mHRF-His$_6$challenge. As a negative control, saline was injected into the ears in place of antigen or HRF challenge. IgG-mediated response was performed by sensitization with 2 µg IgG1 (in place of anti-TNP IgE) and challenge with anti-mouse IgG1 Ab (0.6 µg: Southern Biotechnology, in place of TNP$_{26}$-BSA). Engraftmanet of Kit$^{W-sh/W-sh}$ mice with BMMCs was performed 6 weeks before study (Nakano, T., et al. *J Exp Med* 162:1025-1043 (1985)). In some studies, mice were sensitized and stimulated as described above but without Evans blue.

Airway Inflammation

Mice were sensitized with OVA (10 µg in 0.1 ml saline) at days 0, 7, 14, 21, 28, and 35. Sensitized mice were challenged with OVA (20 µg in 20 µl saline) at days 40, 43 and 46. Some mice were pretreated with GST, GST-N19 (400 µg in PBS), or N19 peptide (40 µg in 2% DMSO-containing PBS) 15 minutes before OVA challenge. Twenty-four hours after the last challenge, lung function in response to methacholine was tested using FlexiVent system (SCIREQ Scientific Respiratory Equipment). Mice were sacrificed and plasma, BAL fluids, and lung tissues were collected. Cells in BAL fluids were counted, and specific cell numbers were calculated after May-Giemsa staining of Cytospin preparations. Immunofluorescence microscopy was performed on membrane-permeabilized and non-permeabilized lung tissues. For staining of lung tissues by staining of H&E and periodic acid-Schiff (PAS), lung tissues were fixed with formalin and embedded in paraffin. For measurement of cytokine levels in lung tissues, lung homogenates were prepared (Oyoshi et al., *Immunol.* 120:303 (2007)) and cytokines quantified by ELISA. HRF in lung homogenates and plasma was SDS-PAGE and immunoblotting with anti-HRF Ab (Santa Cruz Biotechnology).

In the second model (Mathias et al., *J Immunol.* 182:2416 (2009)), BALB/c mice were intranasally treated with *Aspergillus fumigatus* allergen (50 ul, Greer Laboratories) or PBS three times per week for 3 weeks. Some mice were intranasally pretreated with GST or GST-N19 (200 ug/50 ul) from the second week 30 min before each immunization.

Twenty four hours after the last challenge, mice were sacrificed and BAL fluids, blood and lung tissues were collected.

Immunofluorescence Microscopy

For detection of intracellular and extracellular HRF, lung tissues were fixed with 4% paraformaldehyde and embedded in O.C.T. compound (Sakura Finetek U.S.A.). For staining of extracellular HRF, fixed lung sections were incubated with anti-HRF Ab overnight. Washed sections were incubated with Alexa647-conjugated anti-rabbit IgG for 1 hour, then with Alexa555-conjugated wheat germ agglutinin (WGA) for 10 minutes. The specimens were mounted with ProLong® Gold antifade reagent with DAPI (Invitrogen). For staining of intracellular HRF, the sections were stained with Alexa555-conjugated WGA for 10 minutes and treated with cold methanol for permeabilization. Then, the sections were incubated with anti-HRF Ab overnight, incubated with Alexa647-conjugated anti-rabbit IgG Ab for 1 hour, and mounted with ProLong® Gold antigrade reagent with DAPI.

Histology

Lung tissues were fixed with 10% formaldehyde and embedded in paraffin. Six-micrometer sections were stained with H&E. For immunofluorescence, biopsies were fixed in 4% paraformadehyde at 4° C., washed in 10-20% sucrose in phosphate buffered saline, embedded in O.C.T. compound and stored at −80° C. Cryosections were dried, rehydrated, treated with or without methanol, and incubated with anti-HRF (Santa Cruz biotechnology) at 4° C. overnight. After washing, sections were incubated with Alexa Fluor 647-conjugated anti-rabbit IgG (Southern Biotech), and subsequently with Alexa Fluor 555-conjugated wheat germ agglutinin (Invitrogen). Sections were mounted with ProLong Gold antifade reagent with DAPI (Invitrogen). Fluorescent images were acquired using a 3i Marianas™ system (Intelligent Imaging Innovations) microscope.

Food Allergy

BALB/c mice were intraperitoneally sensitised with OVA (50 μg/mouse) plus alum on days 0 and 14. From day 28, mice were intragastrically challenged with OVA (50 mg) three times a week (Brandt, E. B. et al. J. Clin. Invest. 112:1666-1677 (2003)). Before each challenge, mice were starved for 3 h, then pretreated intragastrically with GST or GST-N19 (100 μg), and rested for 30 min. The development of diarrhoea was visually monitored for 90 min after OVA challenge.

Immunofluorescence Microscopic Analysis of Location of GST-N19

Mast cells were incubated at 37° C. with 20 or 200 μg/ml of either TAT-GST, GST, or GST-N19 protein for 0-20 h. Cells were washed three times with PBS and settled on slides glasses. After fixation with 4% paraformaldehyde for 15 min, cells were permeabilised with ice-cold methanol for 10 min., and stained with anti-GST (Santa Cruz biotechnology), followed by Alexa Fluor 488-conjugated anti-mouse IgG (Invitrogen). ProLong Gold antifade reagent with DAPI (Invitrogen) was used to mount the cover classes. Fluorescence was observed with Marianas microscope system (Intelligent Imaging Innovations).

Statistical Analysis

Differences were analyzed by one-way ANOVA and Student's t test. The data indicated mean±SEM. Single, double, and triple asterisks indicate p<0.05, p<0.01 and p<0.001, respectively. The incidence of diarrhea in the food allergy model was analyzed by long-rank test. Spearman's rank correlation coefficient was calculated for correlation between diarrhea occurrence and numbers of mucosal mast cells.

Example 2

This example includes a description of a subset of mouse IgE and IgG molecules, and that human IgE binds to HRF.

A previous report indicated that IgE polyclonal antibody does not interact with HRF (Wantke, et al., *J Allergy Clin Immunol* 103, 642 (April 1999)). To evaluate the possibility of IgE/HRF interactions, a panel of IgE mAbs was examined. N-terminally glutathione S-transferase (GST)-tagged mouse HRF protein (GST-mHRF) or GST were immobilized onto enzyme-linked immunosorbent assay (ELISA) plates and incubated with IgE mAbs. Bound IgE was detected with anti-IgE-biotin and streptavidin-horseradish peroxidase conjugates. GST-mHRF, but not GST, bound C38-2, IGELa2, and 5 other IgE mAbs (FIG. 1A). By contrast, C48-2 and 12 other IgE mAbs failed to bind GST-mHRF using $OD_{450} \leq 0.1$ as an arbitrary cutoff value. Similar results were obtained when mHRF-His$_6$ (C-terminally hexahistidine-tagged mHRF) was used as a capturing agent.

Interaction of the C38-2 and IGELa2 IgE mAbs with mHRF was also demonstrated by co-immunoprecipitation from a mixture of IgE and mHRF. IgEs were incubated with GST- or GST-mHRF-agarose beads. Bead-bound IgEs were pulled down. IgE and GST proteins were detected by immunoblotting with anti-mouse IgE antibody and anti-GST mAb, respectively (FIG. 1B).

Binding of HRF to BMMCs preincubated with or without (gray) the indicated IgE was assessed after cells were incubated with mHRF-His$_6$. Bound mHRF-His$_6$ was detected with rabbit anti-His tag antibody and Alexa647-conjugated anti-rabbit IgG. HRF binding was detected by flow cytometry when WT BMMCs were incubated with an HRF-reactive (C38-2), but not a nonreactive (C48-2 or 206), IgE mAb. (FIG. 1C). No HRF binding was observed in C38-2 IgE-incubated FcεRIα$^{-/-}$ BMMCs that lacked the expression of the high-affinity IgE receptor, FcεRI. Thus, only certain IgEs have the ability to bind mHRF.

Figure 9:
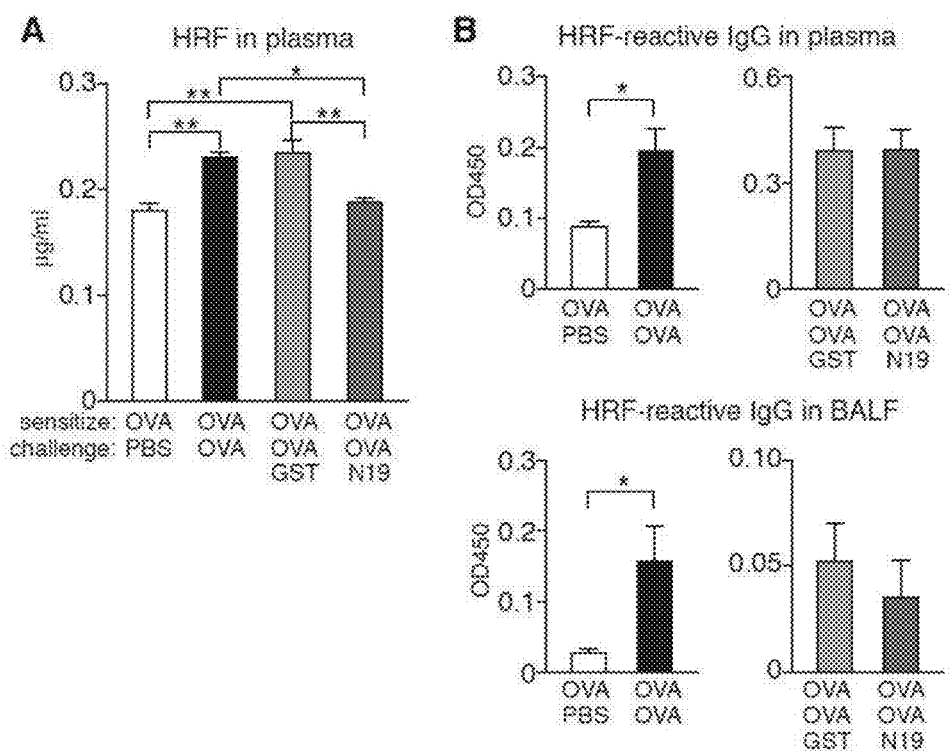
FIGS. 9A-9B show HRF and HRF-reactive IgG measured by ELISA. OVA-immunized mice were intranasally challenged with OVA or PBS. Some mice were pretreated with GST- or GST-N19 before each OVA challenge. Twenty-four hours after the last challenge, the mice were sacrificed and BAL fluids and plasma were collected. HRF in plasma (A) and HRF-reactive IgG (B) in plasma and BAL fluids were measured by ELISA. Data represent mean±SEM. *, $p<0.05$ by Student's t-test.

As both HRF-reactive and HRF-nonreactive IgEs are of allotype a, the HRF-binding site appears to reside in the variable region of IgE. Since the variable region is shared by other Ig isotypes, the interaction of IgG molecules with HRF was studied. IgG molecules were incubated in GST-mHRF-coated wells. HRF-bound IgGs were detected by ELISA. The numbers of mAbs classified into IgG subtypes and $K_D$ values of some IgG molecules to HRF are shown (FIG. 1D). As shown, in FIG. 1D, 9 out of the 34 tested IgG mAbs bound to immobilized GST-mHRF by ELISA. The HRF-binding ability of the IgG mAbs did not correlate with their antigen specificity or isotype. For example, the HRF-binding mAbs, JK31 and JK96, and the non-binding mAb JK116, all recognize the same viral antigen. JK31 and JK116 belong to the IgG1 isotype, while the HRF-binding mAbs, JK126 and JK41, and the non-HRF-binding mAbs, HIT3a and OKT3, belong to the IgG2a isotype. Furthermore, Fab fragments derived from HRF-binding IgE and IgG molecules were found to bind mHRF.

Figure 2:
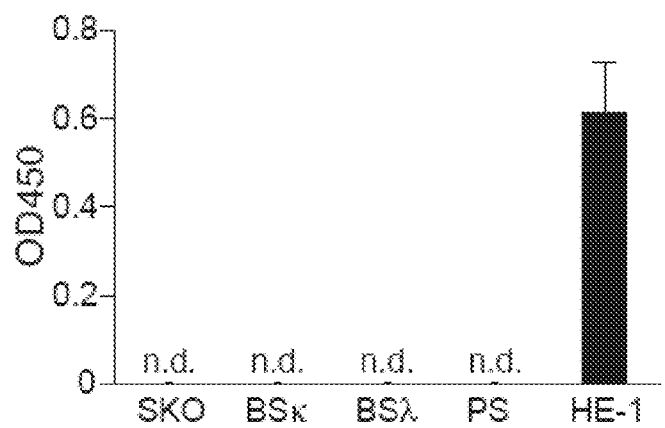
FIG. 2 shows HRF-bound human IgEs detected by incubation with biotin-conjugated anti-human IgE antibody, followed by incubation with horseradish peroxidase-conjugated streptavidin. Absorbance at 450 nm was measured after development of the color. Data indicate mean±SEM. n.d.=not detected.

Human IgE molecules were incubated in GST-mHRF-coated wells. Bound IgEs were detected by incubation with biotin-conjugated anti-human IgE antibody, followed by incubation with horseradish peroxidase-conjugated streptavidin. The absorbance at 450 nm was measured after development of the color. One of the 5 studied human IgEs could bind GST-mHRF (FIG. 2). The results indicate that a considerable proportion of antibodies in immunized mice and humans recognize HRF as a superantigen. GST-hHRF (human HRF) can also bind the Ig molecules that can bind to mHRF, as expected from the 96% identity between hHRF and mHRF proteins.

Binding affinity ($K_D$) between mHRF and IgGs was measured using a quartz crystal microbalance (QCM) method (Mitomo, et al., *J Mol Recognit* 20, 83 (March-April, 2007)). QCM measures a mass per unit area by measuring the change in frequency of a quartz crystal resonator. The results showed that the affinities for three IgG molecules are in the micromolar or submicromolar range (JK17, 0.68 µM; JK31, 2.78 µM; JK96, 5.78 µM) (FIG. 1D).

Example 3

This example includes a description of studies indicating that the N-terminal 19 residue peptide of HRF inhibits the HRF/IgE interaction.

To map the Ig-interaction site within the mHRF molecule, an ELISA panel of N- or C-terminally truncated GST-mHRF proteins (FIG. 3A) was used as capturing agents and two HRF-reactive IgE mAbs (C38-2 and αOE) and two HRF-reactive IgG mAbs (JK18 and JK31) as binding probes. C38-2 and αOE IgE molecules were incubated in wells coated with full-length or truncated forms of GST-mHRF. After blocking, JK18 and JK31 IgGs were incubated. The bound IgGs were detected by incubation with horseradish peroxidase-conjugated anti-mouse IgG antibody. The absorbance at 450 nm was measured after development of the color.

Figure 3:
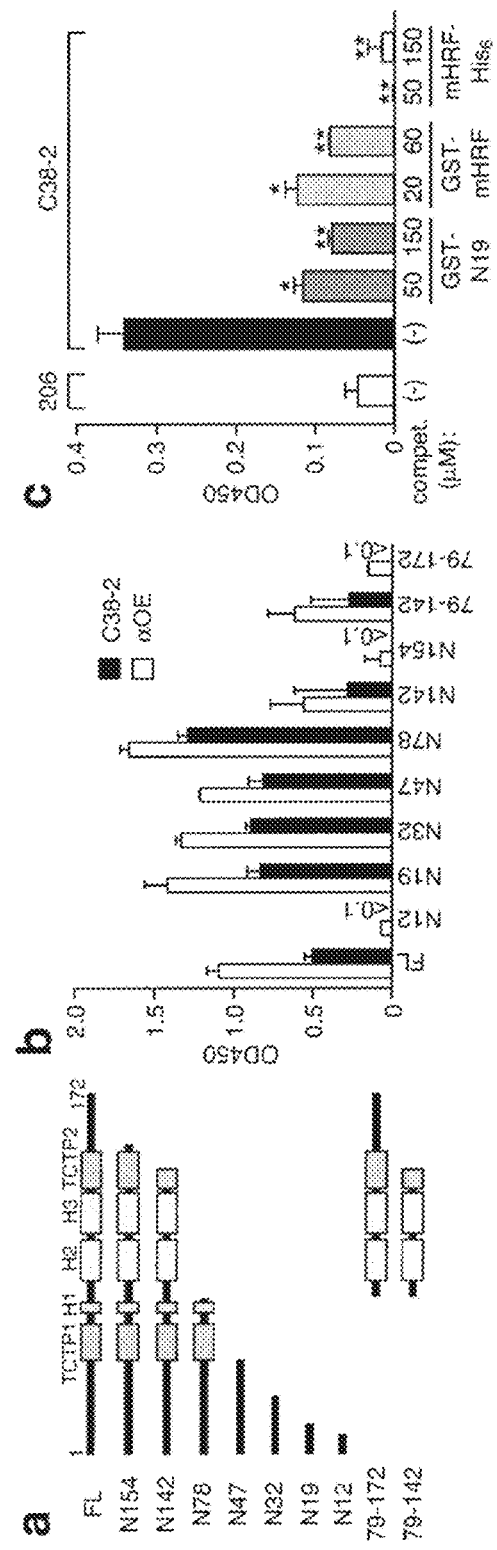
FIGS. 3A-3C show A) the scheme of full-length (FL) and truncated forms of GST-mHRF used for IgE binding; B) HRF-bound IgE detected using anti-mouse IgE by ELISA; and C) HRF-bound-IgE in the absence (−) or presence (+) of competitors as detected by incubation with biotinylated anti-mouse IgE mAb, followed by streptavidin-HRP.
Figure 4:
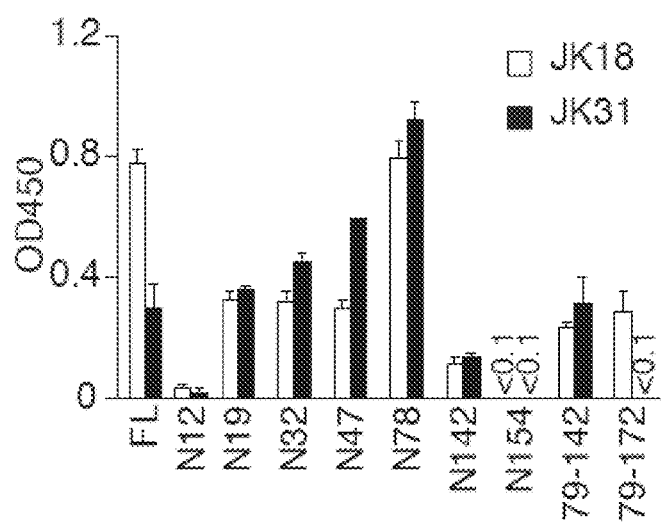
FIG. 4 shows HRF-bound IgGs detected by incubation with horseradish peroxidase-conjugated antimouse IgG antibody. Absorbance at 450 nm was measured after development of the color. Data indicate mean±SEM.

HRF-reactive IgE and IgG mAbs gave similar binding patterns (FIGS. 3B and 4). C-terminal truncations of mHRF up to residue 19 did not affect Ig binding, but a further truncation abrogated Ig binding. Thus, a major Ig-binding site was mapped to the N-terminal part of HRF (residues 1-19). A comparison between GST-N78 and other C-terminally truncated HRF constructs showed that retention of the HRF sequence from position 79 to position 142 or 154 reduces Ig binding. Thus, this HRF sequence inhibits Ig binding via the N-terminal binding site. Binding assays using N-terminally truncated proteins, 79-172 and 79-142, indicated that another Ig-binding site is present at the internal part of HRF (residues 79-142) and that the C-terminal fragment of HRF (residues 155-172) prevents this internal segment of HRF from interacting with the Igs. Thus, HRF can interact with the IgE and IgG molecules via at least two interaction sites with the mHRF's N-terminal interaction site functioning as a predominant interaction site.

Example 4

This example includes a description of studies indicating that GST-N19 does not affect the growth or apoptosis in various cells.

To identify an inhibitor of HRF/Ig interactions to dissect the extracellular function (=HRF function as a cytokine) separate from the intracellular functions in vivo settings, the major Ig-interacting HRF sequence was studied as a specific inhibitor of HRF/Ig interactions. IgE molecules were incubated in GST-mHRF-coated wells in the presence or absence (−) of the indicated concentrations of competitors, GST-N19, GST-mHRF or mHRF-His$_6$ for 2 hours. After incubation, bound-IgE was detected by incubation with biotinylated anti-mouse IgE mAb, followed by streptavidin-HRP. GST-N19 (encoding the first 19 residues of mHRF; designated N19 in FIG. 3A) inhibited IgE binding to immobilized GST-mHRF by ELISA with potency similar to that shown by GST-mHRF and mHRF-His$_6$ (FIG. 3C). By contrast, none of the shorter mHRF peptides tested (residues 1-6, 1-12, 5-19, and 9-19) inhibited HRF/IgE binding. GST-N19 inhibited HRF/IgG binding as well.

Figure 5:
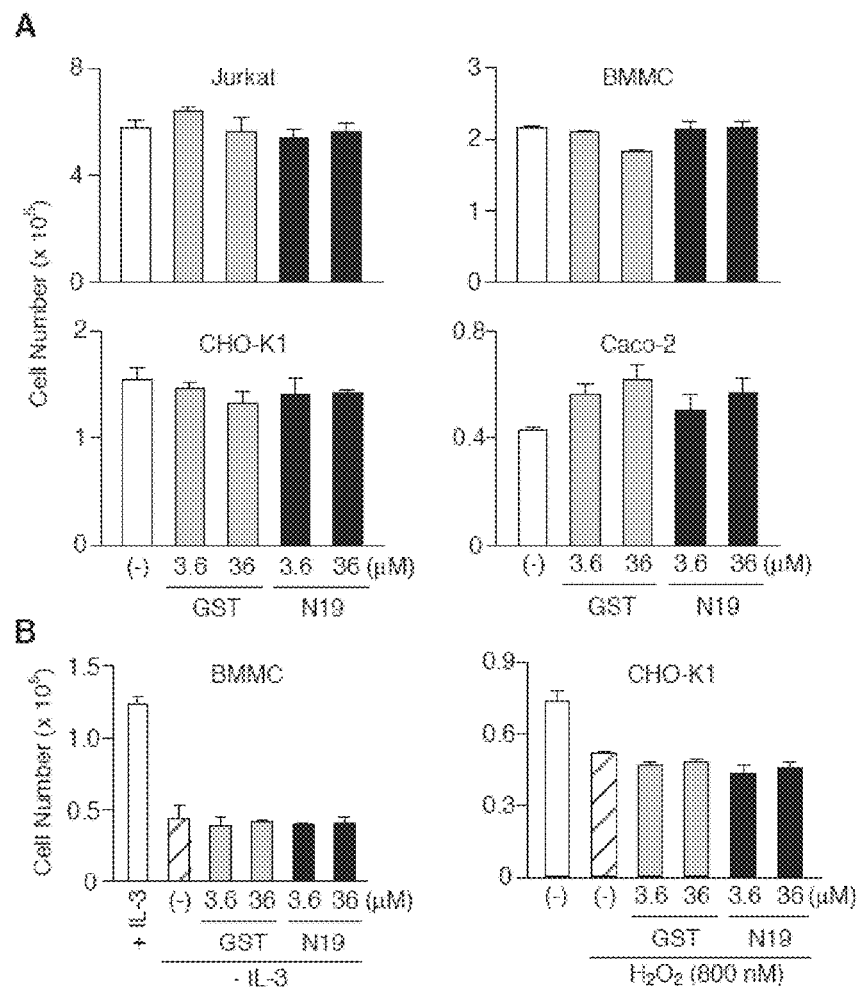
FIGS. 5A-5B show A) cells cultured in the absence (−) or presence of the indicated concentrations of GST or GST-N19 for 2 days, and live cells detected by the exclusion of Trypan blue; and B) live BMMC or CHO-K1 cells after IL-3 withdrawal or $H_2O_2$ induced apoptosis, respectively. Data indicate mean±SEM.

To analyze the effect of GST-N19 on intracellular functions of HRF/TCTP, the indicated cells were cultured in the absence (−) or presence of the indicated concentrations of GST or GST-N19 for 2 days, and live cells were counted in the presence of Trypan blue. Treatment of the cultures of BMMCs, CHO-K1 (Chinese hamster ovary cell), Jurkat (human T cell), Caco-2 (human colonic epithelial cell), A549 (human lung epithelial cell), and HeLa (human cervical epidermal cell) cells with 3.6 or 36 µM of GST-N19, did not affect viability or proliferation of either cells (FIG. 5A, live cells shown by the exclusion of Trypan blue). The usual dose of HRF to stimulate basophils is 1.6-5 µM (Langdon, et al., *J Leukoc Biol* 84, 1151 (October, 2008)). Apoptosis was induced by growth factor withdrawal, IL-3 depletion, in BMMCs for 3 days and by 800 nM $H_2O_2$ in CHO-K1 cells for 2 days, and live cells were counted. The CHO-K1 cells were not affected by GST-N19 (FIG. 5B). Furthermore, confocal microscopy showed that GST-N19 does not enter the interior of cells.

These results indicate that N19 peptide can be used to probe the specific in vivo function of HRF/Ig interactions or the HRF function as an autoantigen. All these and subsequent in vitro and in vivo studies were performed using recombinant proteins (mHRF-His$_6$, GST, and GST-N19) that contained <0.05 pg/µg protein of endotoxin.

Example 5

This example includes a description of studies indicating that HRF can induce weak acute and strong late-phase anaphylactic cutaneous reactions in HRF-reactive IgE-sensitized mice.

Figure 6:
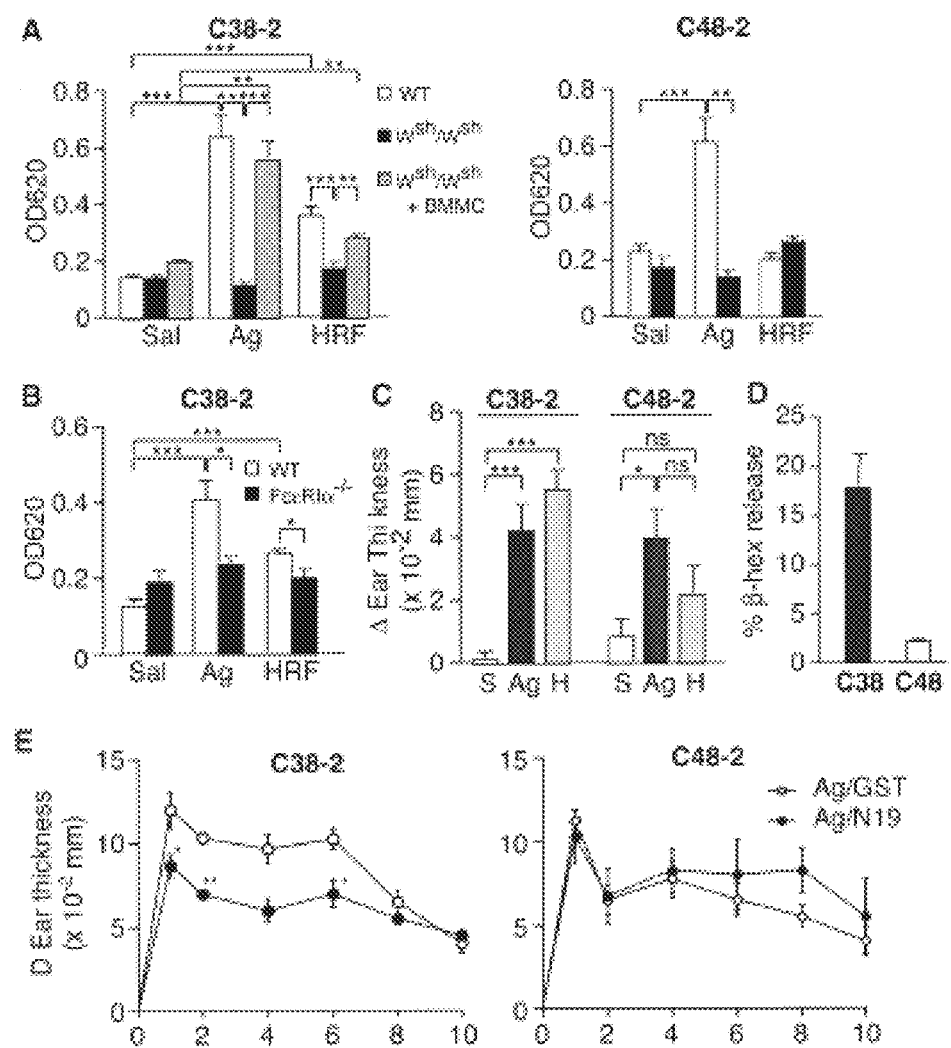
FIGS. 6A-6E show A) BMMC engrafted $W^{sh}/W^{sh}$ mice which were confirmed by Toluidine Blue staining have levels of mast cells similar to those of WT mice. HRF or negative and positive controls, saline (S) and TNP$_{26}$-BSA (Ag), respectively, were injected in IgE (C38-2 or C48-2) sensitized ears and vascular permeability was measured after 30 minutes; B) acute reactions in FcεRIα$^{-/-}$ mice were not induced; C) Late Phase Reactions (LPR) were analyzed by measurement of ear thickness at 8 hours after injection of mHRF-His$_6$ (H) in IgE (C38-2 or C48-2)-sensitized ears. Negative and positive controls, saline (S) and TNP$_{26}$-BSA (Ag), respectively, were injected in sensitized ears; D) β-hexosaminidase release from peritoneal mast cells sensitized with the HRF-reactive, but not the HRF-nonreactive, IgE were activated upon stimulation with HRF; and E) WT mice sensitized with the indicated IgE. Ear thickness was measured over a 10 hour period. *, , *: $p<0.05$, $p<0.01$, $p<0.001$ by Student's t-test.

Acute passive cutaneous anaphylaxis (PCA) reactions, a typical type I hypersensitivity, are usually induced by multivalent antigen in IgE-sensitized mice and mediated mainly by histamine released from activated mast cells, while the late-phase reactions (LPR) in the skin is mediated in part by TNF-α secreted from activated mast cells (Wershil, et al., *J Clin Invest* 87, 446 (February, 1991), Nagai et al., *Inflamm Res* 45, 136 (March, 1996)). Here, mice were sensitized with the IgE. Twenty four hours later, Evans blue was intravenously injected and mHRF-His$_6$ was consecutively injected in IgE-sensitized ears. After 30 minutes, mice were sacrificed, and the amount of Evans blue dye leaked from the ears measured. For negative and positive controls, saline (Sal) and TNP$_{26}$-BSA (Ag), respectively, were injected in sensitized ears. In addition to C57BL/6 (WT), B6-Kit$^{W-sh/W-sh}$ mice were used before or 6 weeks after engraftment of WT BMMCs by intradermal injection. Toluidine Blue staining confirmed that the engrafted mice had levels of mast cells similar to those of WT mice. The intradermal injection of mHRF 24 hours after IgE injection showed that both the acute reactions and LPR are induced by HRF-reactive, but not HRF-nonreactive, IgEs (FIG. 6). The HRF-reactive C38-2 IgE, but not the nonreactive C48-2 IgE, induced increased vascular permeability measured at 30 minutes after mHRF injection (FIG. 6A).

mHRF-His$_6$ (H) was injected in IgE-sensitized ears and LPR was analyzed by measurement of ear thickness at 8 hours after injection. For negative and positive controls, saline (S) and TNP$_{26}$-BSA (Ag), respectively, were injected in sensitized ears. Interestingly, the LPR induced by HRF, as measured by increased ear swelling at 8 hours, was as high as that induced by antigen (FIG. 6C).

Figure 7:
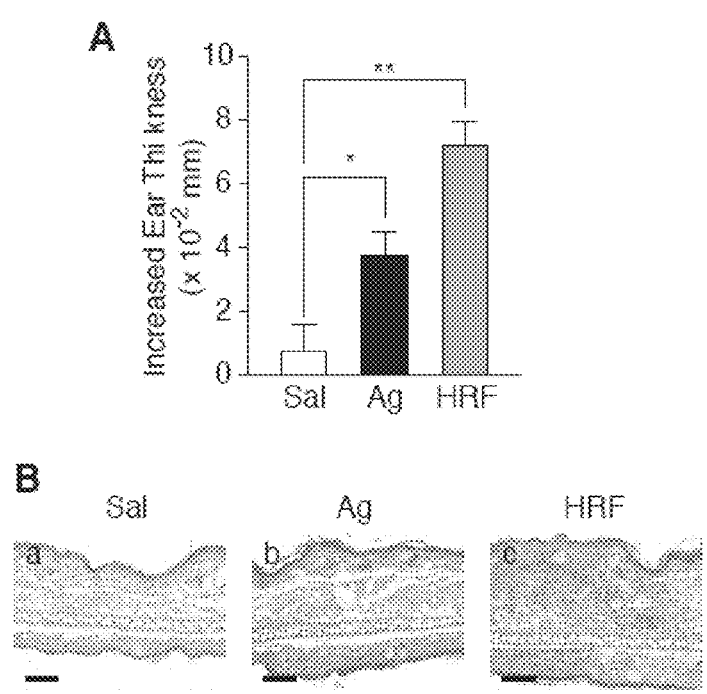
FIGS. 7A-7B show A) ear thickness of mice sensitized with IgE in the presence of saline, TNP$_{26}$-BSA, or HRF B) H&E staining of sensitized mouse ears. Bar=100 μm. Data indicate mean±SEM. *, **: $p<0.05$, $p<0.01$ by Student's t-test.

Similar weak acute and strong late-phase responses were observed using another HRF-reactive IgE, IGELa2, in both C57BL/6 and BALB/c mice (FIG. 7). IGELa2 IgE was intradermally injected into ears. After overnight sensitization, the mice were challenged by intradermal injection of saline (Sal), antigen (Ag), or HRF. Eight hours after injection, the ear thickness was measured (FIG. 7).

These hypersensitivity reactions appear to be dependent on mast cells, as the reactions were abolished in mast cell-deficient Kit$^{W-sh/W-sh}$ mice and restored in Kit$^{W-sh/W-sh}$ mice engrafted with WT BMMCs (FIG. 6A). Furthermore, FcεRIα$^{-/-}$ mice showed neither acute or late-phase responses (FIG. 6B). Therefore, HRF and HRF-reactive IgE can induce anaphylactic responses in a mast cell- and FcεRI-dependent manner. Consistent with this, peritoneal mast cells sensitized with the HRF-reactive, but not the HRF-nonreactive, IgE were activated upon stimulation with HRF (FIG. 6D). After 40 minutes, both supernatants and cell pellets were collected and β-hexosaminidase release was analyzed (FIG. 6D). Similar weak acute and strong late-phase responses were also induced by HRF and HRF-reactive IgG.

To study HRFs involvement in IgE/antigen-induced PCA reactions, WT mice were overnight sensitized the IgE. Left ears were injected with GST and the right ears were injected with GST-N19, and then TNP$_{26}$-BSA were injected in both ears. Ear thickness was measured over a 10 hour period. *, , *: p<0.05, p<0.01, p<0.001 by Student's t-test. As shown in FIG. 6E, both acute reactions and LPR in an HRF-reactive IgE-induced PCA were significantly reduced by GST-N19, but not GST. However, PCA induced by an HRF-nonreactive IgE was insensitive to GST-N19.

Example 6

This example includes a description of studies indicating that HRF is involved as a superantigen in amplifying airway inflammation.

Figure 8:
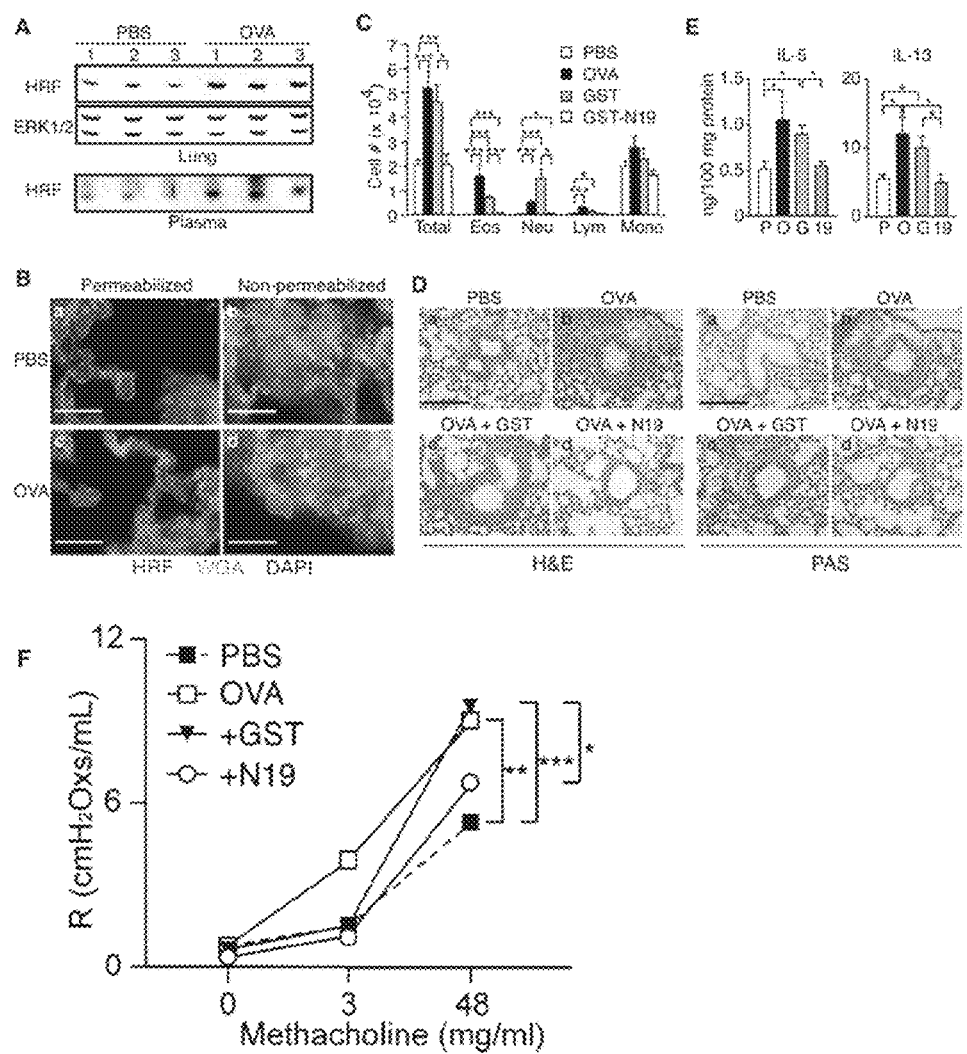
FIGS. 8A-8F show A) immunoblotting on lung homogenates and plasma samples of HRF expression levels. For loading control, ERK1/2 expression was analyzed; B) immunofluorescence microscopy on membrane-permeabilized or non-permeabilized lung tissues. HRF was stained red. The plasma membrane was stained with wheat germ agglutinin (green) and the nuclei with DAPI (blue). Bar=200 μm; C) total and specific immune cell numbers in BAL fluids were enumerated. Eos, eosinophils; Neu, neutrophils; Lym, lymphocytes; Mono, monocytes; D) paraffin-embedded lung tissues stained by H&E and periodic acid-Schiff (PAS). Bar=200 μm; E) IL-5 and IL-13 in lung homogenates (PBS [P], OVA [O], OVA+GST [G], and OVA+N19 [19]) measured by ELISA; and F) that GST-N19 treatment inhibited airway hyper-responsiveness (AHR). Data indicate mean±sem. *, , *: $p<0.05$, $p<0.01$, $p<0.001$ by Student's t-test.
Figure 10:
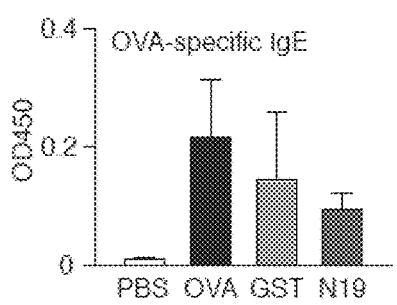
FIG. 10 shows Ig levels in plasma from OVA-immunized mice challenged with OVA or PBS pretreated with GST- or GST-N19, before each OVA challenge. OVA-specific IgE, IgG1, and IgG2a were measured by ELISA. Data represent mean±SEM. *, $p<0.05$ by Student's t-test.
Figure 10:
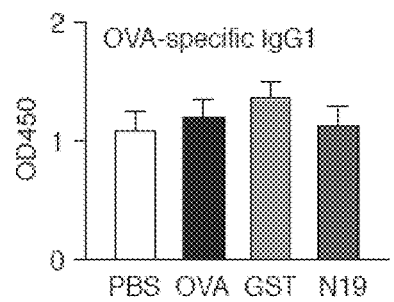
Figure 10:
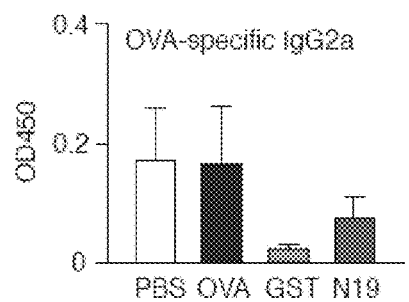
Figure 11:
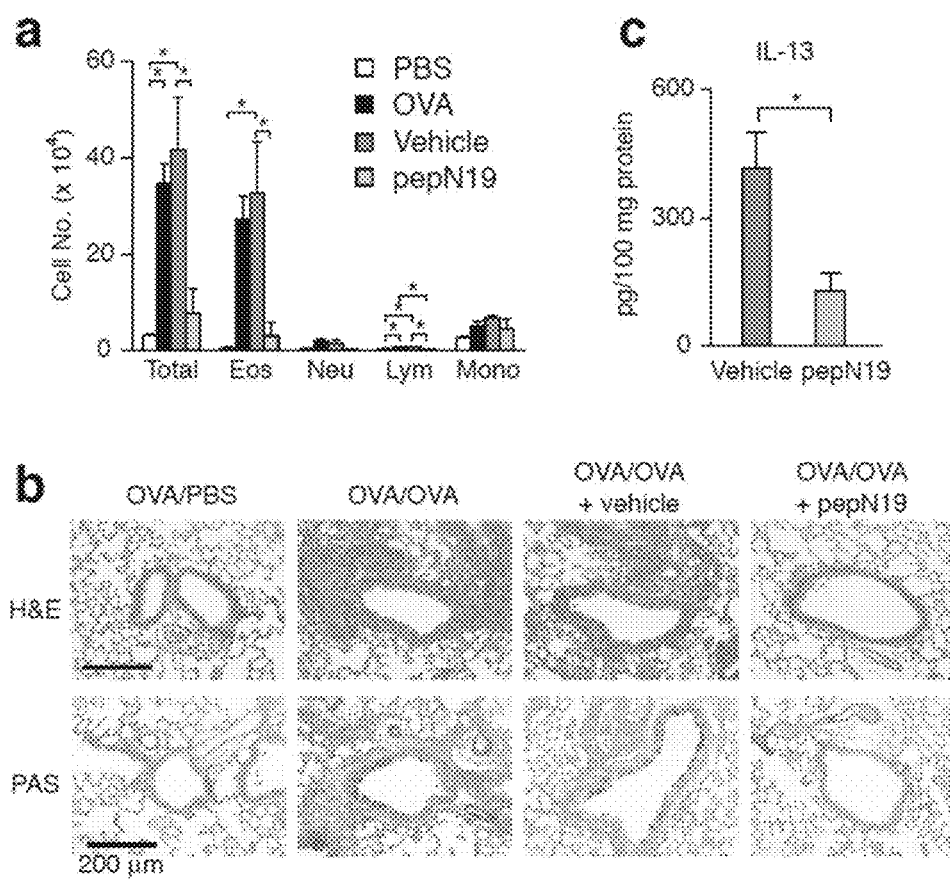
FIGS. 11A-11E show A) total and specific immune cell numbers in BAL fluids. Eos, eosinophils; Neu, neutrophils; Lym, lymphocytes; Mono, monocytes; Mφ, macrophages; B) Paraffin-embedded lung tissues stained by H&E and periodic acid-Schiff (PAS). Bar=200 μm; C) IL-13 suppression by GST-N19; and that GST-N19 does not inhibit T cell-dependent/mast cell-independent airway inflammation. D) Paraffin-embedded lung tissues stained by H&E and periodic acid-Schiff (PAS). Bar=100 μm. E) Total and specific immune cell numbers in BAL fluids were enumerated. Data indicate mean±sem. *, , *: $p<0.05$, $p<0.01$, $p<0.001$ by Student's t-test.
Figure 12:
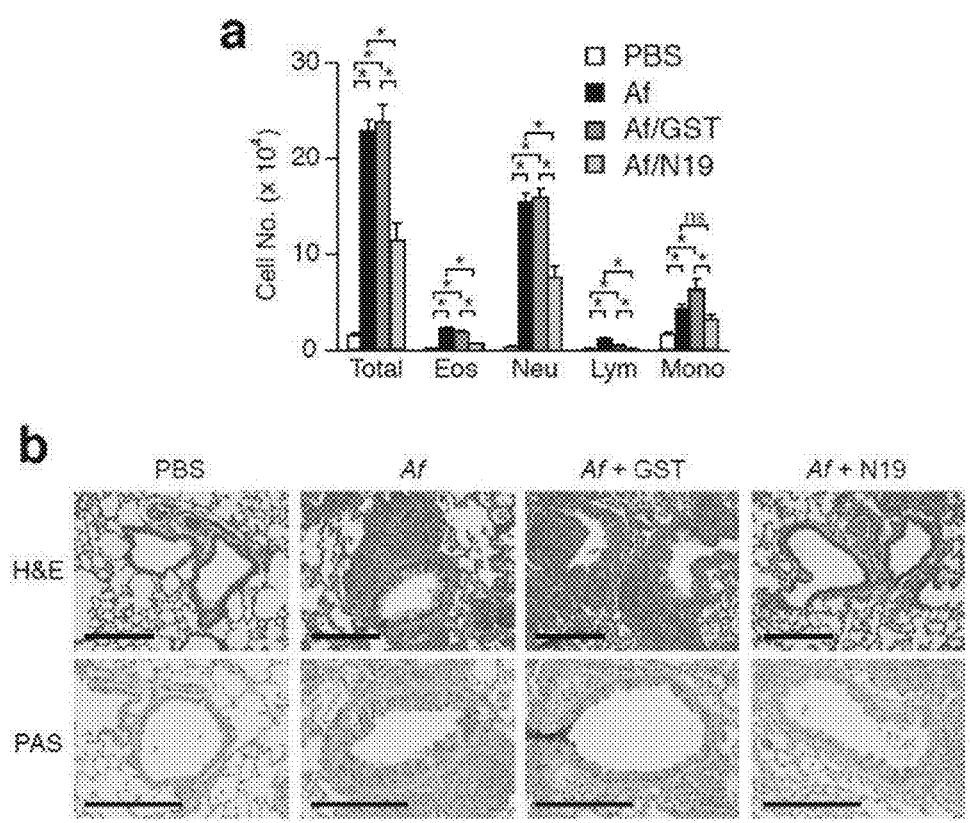
FIGS. 12A-12B show GST-N19 inhibits *Aspergillus fumigatus* allergen-induced airway inflammation. BALB/c mice were lightly anesthetized by isoflurane inhalation, and 50 μl of *Aspergillus* allergen or PBS was applied to the bares. Mice were immunized three times per week for 3 weeks, as described previously (Mathias et al., *J. Immunol.* 182:2416 (2009)). Some mice were intranasally pretreated with GST or GST-N19 (200 mg/50 ml) from the second week 30 min before each immunization. Twenty-four hours after the last challenge, mice were sacrificed and BAL fluids and lung tissues were collected. A) Total and specific immune cell numbers in BAL fluids were enumerated. Eos, eosinophils; Neu, neutrophils; Lym, lymphocytes; Mono, monocytes. B) Paraffin-embedded lung tissues were stained by H&E and periodic acid-Schiff (PAS). Bar=200 μm. Data indicate mean±sem. *, , *: $p<0.05$, $p<0.01$, $p<0.001$ by Student's t-test.

Asthma is a type 2 helper T cell-driven, chronic inflammatory lung disease (Wills-Karp, Annu Rev Immunol 17, 255 (1999)). To study HRF involvement in allergic airway inflammation, an airway inflammation model was utilized, in which mast cells are implicated in amplifying antigen-dependent chronic inflammation (Williams, et al., J Exp Med 192, 455 (Aug. 7, 2000)). C57BL/6 mice were first sensitized with OVA (10 μg) at days 0, 7, 14, 21, 28 and 35. At days 40, 43 and 46, mice were intranasally challenged with OVA (20 μg) or PBS. Some mice were intranasally pretreated with GST or GST-N19 (400 μg) before every OVA challenge. Twenty-four hours after the last challenge, mice were sacrificed and BAL fluids and lung tissues were collected. Lung tissues were homogenized. In addition to the increased HRF levels in lung tissues, BAL fluids, and plasma of OVA-immunized/OVA challenged mice (FIGS. 8A and 9A; plasma HRF: 0.367±0.09 μg/ml in PBS-treated mice vs. 1.32±0.13 μg/ml in OVA-challenged mice, p=0.0036), immunofluorescence microscopy of lung sections showed increased levels of HRF staining in non-permeabilized lung tissues (FIG. 8B), indicating that HRF is secreted into the lung tissues in OVA-immunized/OVA-challenged mice. Levels of HRF-reactive IgG were also increased in plasma and BAL fluids of these mice (FIG. 9B), while HRF-reactive IgE was under detection limits in our assays. Treatment with GST-N19 before each OVA challenge abrogated airway inflammation, as evidenced by reduced inflammatory cells, particularly, eosinophils and neutrophils, in BAL fluids (FIG. 8C) and by reduced inflammatory cells and goblet cell hyperplasia in the lung (FIG. 8D). Production of IL-13 (the cytokine essential for airway hyperresponsiveness, eosinophilia and mucus production (Wills-Karp, et al., Science 282, 2258 (Dec. 18, 1998), Grunig, et al., Science 282, 2261 (Dec. 18, 1998)) and IL-5 (the cytokine critical for eosinophilia and airway hyperresponsiveness (Foster, et al., J Exp Med 183, 195 (Jan. 1, 1996)) in lung tissues was drastically decreased in GST-N19-treated mice (FIG. 8E). Consistent with these observations, GST-N19 treatment inhibited AHR (FIG. 8F). Furthermore, the increased HRF in plasma in OVA-immunized/OVA-challenged mice were reduced by GST-N19 (FIG. 9A). By contrast, HRF-reactive IgG levels (FIG. 9B) or OVA-specific IgE, IgG1, or IgG2a levels (FIG. 10) in plasma were not affected by GST-N19. Administration of the synthetic non-fusion N19 peptide also abrogated airway inflammation (FIG. 11A-11C). By contrast, GST-N19 failed to inhibit airway inflammation in a T cell-dependent/mast cell-independent model (Takeda, et al., J Exp Med 186, 449 (1997)), in which mice were immunized with OVA with alum and challenged with OVA (FIGS. 11D and 11E). The efficacy of GST-N19 was confirmed in another model of asthma, one induced by Aspergillus fumigatus allergens (FIG. 12), which induced dramatic expansion and activation of airway mast cells and recruitment of eosinophils in an IgE-dependent manner. These results strongly indicate that HRF is critically involved as a superantigen in amplifying airway inflammation.

Example 7

This example includes a description of studies indicating that weak lung inflammation is induced by HRF alone in naïve mice.

Figure 13:
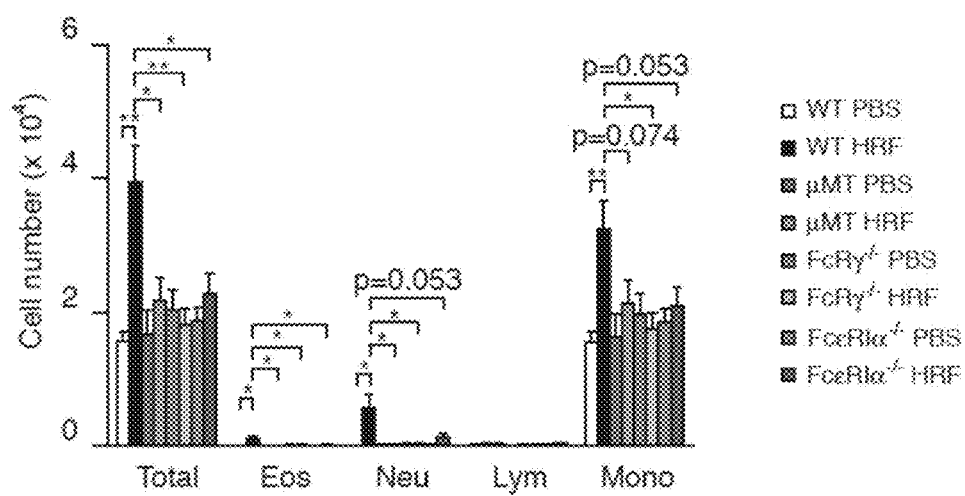
FIG. 13 shows weak lung inflammation is induced by HRF alone in naïve mice. Differential cell counting was performed on cytospin preparations stained with May-Giemsa. P values by Student's t-test are shown.

In light of the presence of HRF-reactive IgG in naïve mice and recent studies reporting the role of mast cells in the initiation of adaptive immune responses (Galli, et al., Nat Immunol 6, 135 (February, 2005)), the effect of HRF on naïve mice was assessed. Unimmunized C57BL/6 (WT), μMT, and FcRγ$^{-/-}$ mice (n=5 per cohort) were treated intranasally with 40 μg mHRF-His$_6$ three times every third day. PBS served as a negative control. BAL procedures were conducted 24 hours after the last HRF administration. Differential cell counting was performed on cytospin preparations stained with May-Giemsa. Intranasal administration of mHRF-His$_6$ induced weak lung inflammation, as shown by increased neutrophils and eosinophils in BAL fluids (FIG. 13). HRF effects were not observed in B cell-deficient (μMT) or FcRγ$^{-/-}$ mice, suggesting that HRF requires Igs and Fc receptors for its proinflammatory function. FcRγ is shared by multiple Fc receptors including FcεRI. Among the candidate Igs and Fc receptors, IgE and its receptor, FcεRI, seemed to play a predominant role, as HRF-induced lung inflammation was abrogated or reduced in naïve FcεRIα$^{-/-}$ mice. Since FcεRI is expressed only in mast cells and basophils in mice, these results are consistent with the effectiveness of N19 peptide in mast cell-dependent asthma models. The failed increase of inflammatory cells in BAL fluids of HRF-challenged naïve μMT or FcRγ$^{-/-}$ mice suggests that HRF does not have receptors other than Igs.

Example 8

This example includes a description of studies indicating that N19 peptide pretreatment prevents development of diarrhea in a mouse model of food allergy.

Figure 14:
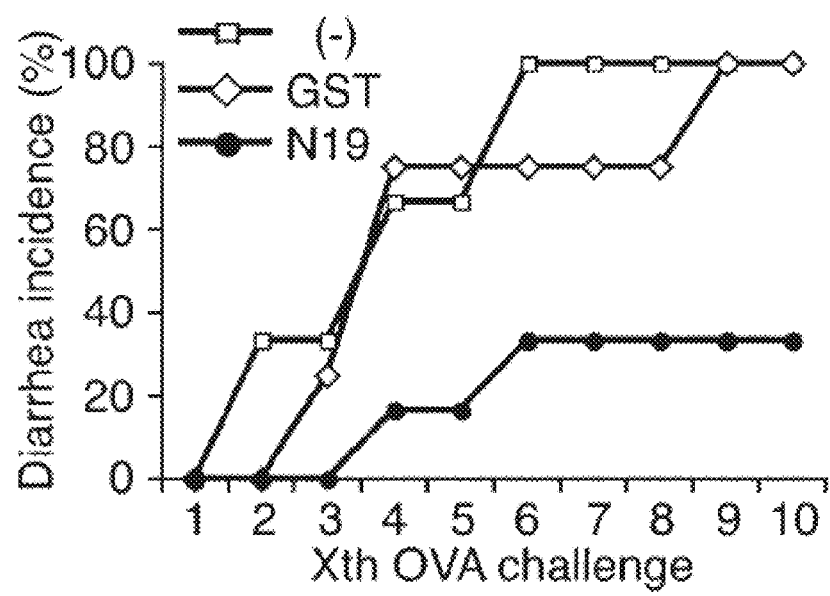
FIG. 14 shows GST-N19 prevents the development of diarrhea. The development of diarrhea was monitored for ninety minutes after OVA challenge. Log-rank test: $p=0.028$ (GST vs. GST-N19), $p=0.036$ (Control vs. GST-N19). Five or six mice per group.
Figure 15:
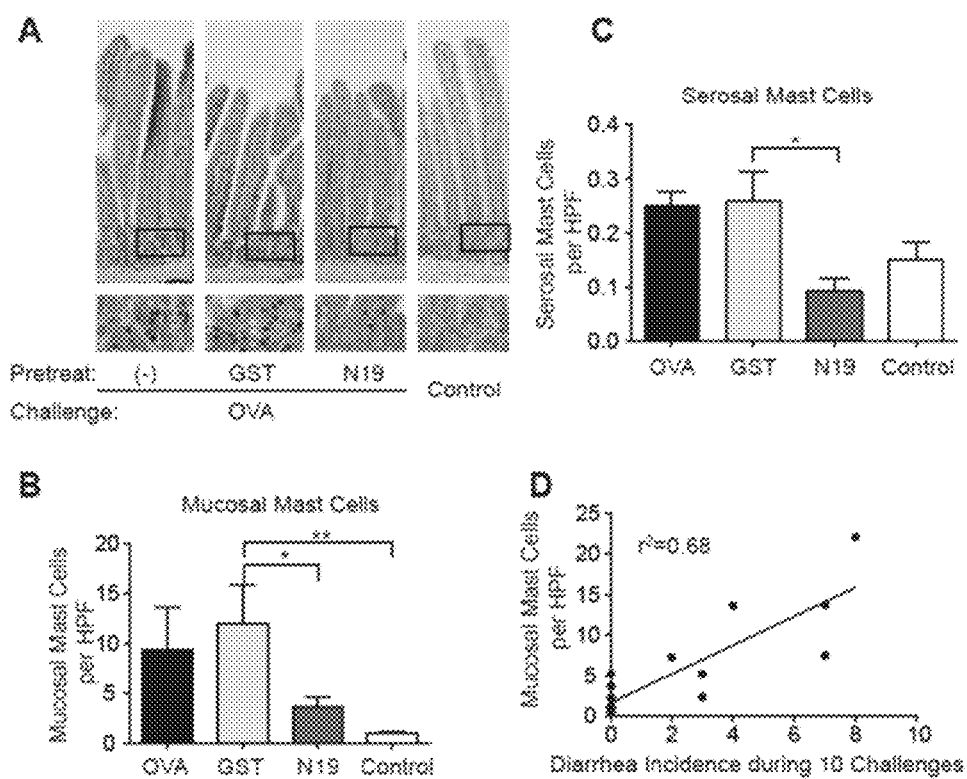
FIGS. 15A-15D show GST-N19 inhibits mastocytosis in the small intestine in the OVA-induced food allergy model. A) representative results of the jejunal sections. Sections indicated by rectangles are enlarged in lower rows; B) mucosal; C) serosal mast cells were enumerated in each high-power field (HPF); and D) correlation was found between diarrhea occurrence and numbers of mucosal mast cells. Spearman's $r=0.8262$ ($r^2=0.68$), $p<0.0001$.
Figure 16:
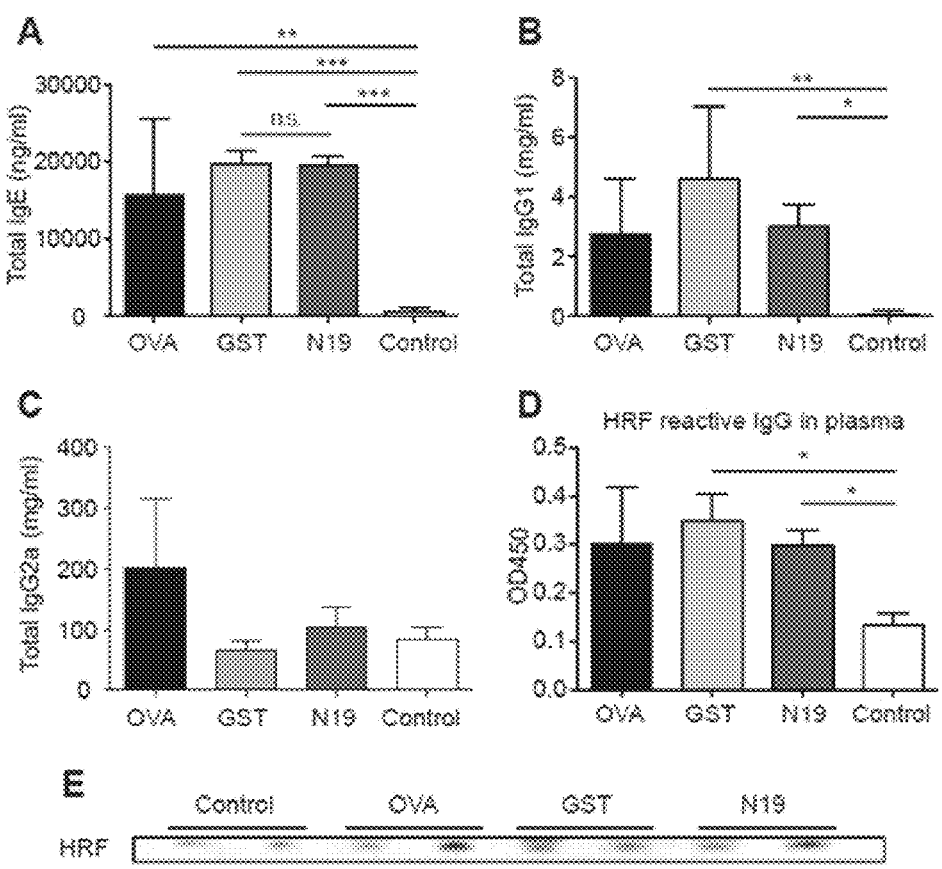
FIGS. 16A-16E show plasma levels of A) IgE; B) IgG1; C) IgG2a measured using commercial ELISA kits; D) HRF-reactive IgG measured in ELISA using mHRF-His$_6$ as a capturing agent. After incubation with plasma (diluted 200 folds), bound IgG was detected with HRP-conjugated anti-mouse IgG. *, , *: $p<0.05$, $0.01$, $p<0.001$ by Student's t-test; and E) Immunoblot analysis of plasma HRF levels. Two samples per group were analyzed.

To evaluate the role of HRF in food allergy, an OVA-induced food allergy model developed by Brandt et al. (Brandt et al., J. Clin. Invest. 112:1666 (2003)) was employed. BALB/c mice that were 6-8-week-old were intraperitoneal (i.p.) immunized twice on days 0 and 14 with 50 µg of OVA in the presence of alum. From day 28, mice were intragastrically challenged with OVA (50 mg) three times a week. Before each challenge, mice were starved for 3 hours, then pretreated with GST or GST-N19 (100 µg/mouse) intragastrically, and rested for 30 minutes. Control mice were sensitized and challenged, but not pretreated. The development of diarrhea was monitored for ninety minutes after OVA challenge. Visual monitoring following each intragastric OVA challenge showed the induction of diarrhea in OVA-immunized, but not PBS control mice (FIG. 14). Sections of jejunum and ileum from mice treated as in FIG. 14 were stained with chloroacetate esterase. These sections of jejunum and ileum revealed increased mucosal mast cells in mice (FIG. 15A-C). There was a good correlation shown between the number of mucosal mast cells and the number of diarrhea occurrence during 10 OVA challenges (FIG. 15D). Increased serum IgE and IgG1, but not IgG2a, levels (FIG. 16) and increased expression of mRNAs encoding Th2 cytokines (IL-4, IL-5, IL-13) and proinflammatory cytokines (IL-6, IL-1β) in the intestines were observed (data not shown). In this Th2-skewed model, the amount of HRF in plasma from diarrhea-induced mice, as measured by immunoblotting, was increased by about 2 fold compared to PBS control mice (FIG. 16E). HRF-reactive IgG levels were also increased in sera of diarrhea-induced mice (FIG. 16D). However, HRF-reactive IgE was not detected under the study conditions.

Importantly, the development of diarrhea was prevented in a much greater percentage of mice pretreated with GST-N19 than in GST-pretreated or PBS-treated control mice (FIG. 14). Increases in both mucosal and serosal mast cells were inhibited by GST-N19 pretreatment (FIG. 15A-C). However, plasma levels of total IgE, total IgG1, total IgG2a, or HRF-reactive IgG were not affected by GST-N19 (FIG. 16). These results indicate that HRF is involved in OVA-induced diarrhea induction and mast cell accumulation in the small intestine. Given the absence of GST-N19 effects on mast cell growth and apoptosis, the inhibition of mast cell accumulation in GST-N19-treated mice might be due to reduced recruitment of mast cells in the inflamed intestines.

Example 9

This example includes a description of studies indicating that human food allergy patients with high serum IgE levels tend to have increased levels of serum HRF and HRF-reactive IgG.

Figure 17:
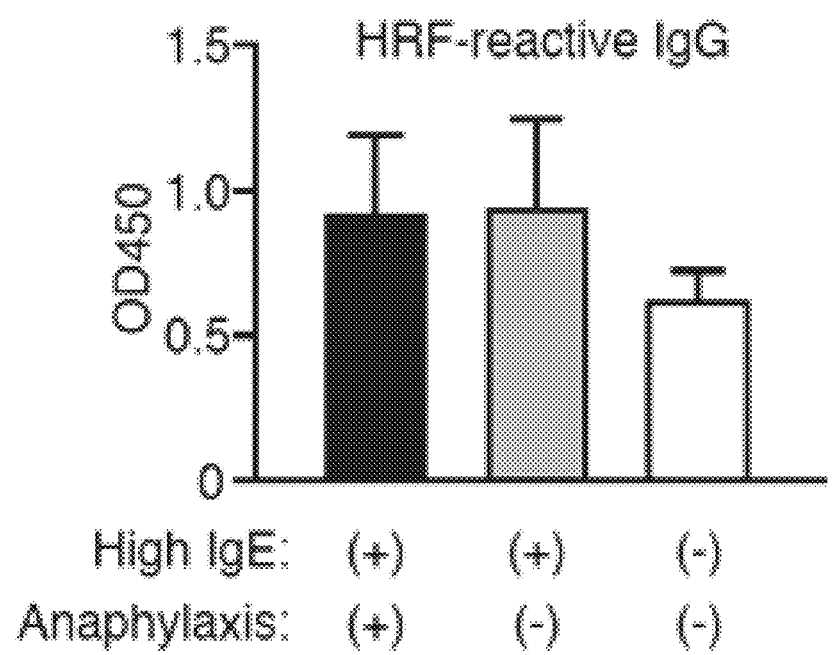
FIG. 17 shows ELISA of sera from food allergy patients stratified by IgE levels (+, ≥0.35 kU/L; −, <0.35 kU/L) and anaphylaxis to measure HRF-reactive IgG. Each cohort consists of 4 or 6 patients.

To determine if the histamine-releasing activity associated with food allergy, which was described 20 years ago (Sampson et al., N. Engl. J. Med. 321:228 (1989)), is due to HRF, serum HRF-reactive IgG levels in small cohorts (n=4 or 6 per cohort) of food allergy patients with increased serum food-specific IgE who showed anaphylaxis or not, and food allergy patients with no increase in food-specific serum IgE, was measured. There were small, although statistically not significant, increases in HRF-reactive IgG levels in patients with high food-specific IgE levels (FIG. 17). The results indicate that food allergy patients tend to have higher levels of serum HRF and HRF-reactive IgG.

Example 10

This example includes a description of studies indicating that an HRF-reactive IgE can bind both monomeric and dimeric forms of HRF.

Figure 18:
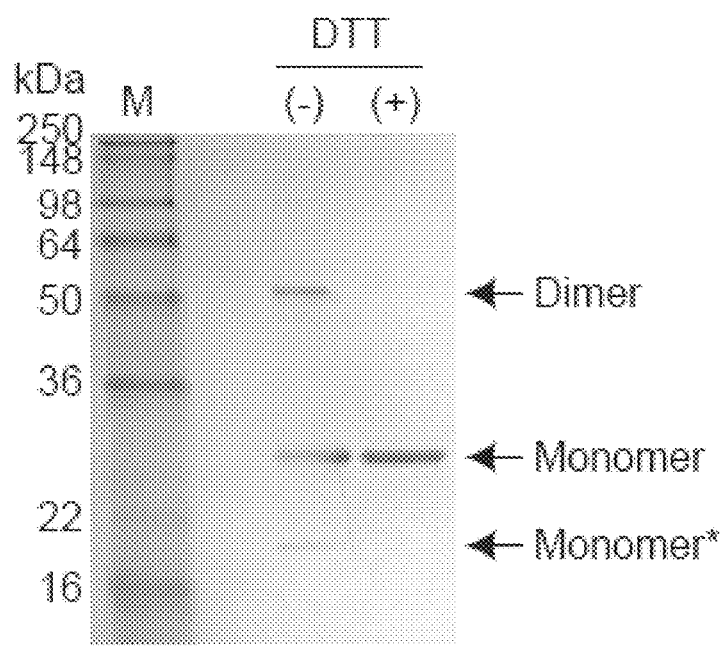
FIG. 18 shows HRF as both monomeric and dimeric forms. Positions of monomer and dimer are indicated. Monomer* may be a form of monomer with intramolecular disulfide bonding.

HRF binding to IgE (or IgG) bound to Fc receptors activates immune cells such as mast cells and basophils. A potential cell activation mechanism by HRF is through HRF interactions with two or more Ig molecules and/or multimerization of HRF molecules, both leading to crosslinking Ig-bound Fc receptors. The former was indicated by the above-mentioned mapping results (FIG. 3B). Analysis of purified recombinant mHRF-His$_6$ on reducing and non-reducing SDS-PAGE yielded direct evidence for dimerization of mHRF (FIG. 18). In this study (FIG. 18), mHRF-His$_6$ protein purified with ProBond™ nickel-chelating resin (Invitrogen) was analyzed by SDS-PAGE under reducing (100 mM DTT) or non-reducing conditions and stained with Coomassie Brilliant Blue. Size exclusion chromatography also indicated that the mHRF protein consists of disulfide-linked homodimers and monomers.

Figure 19:
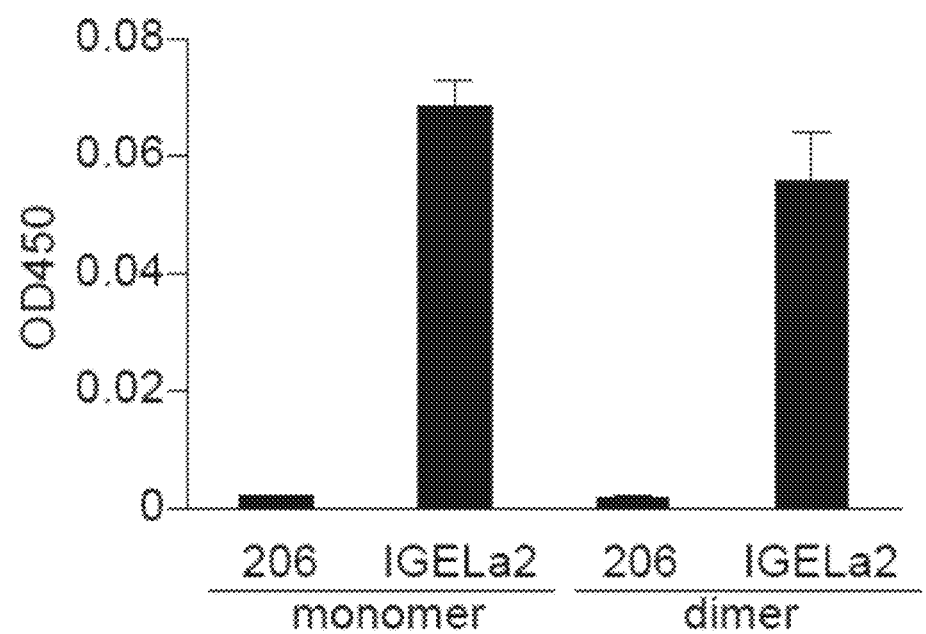
FIG. 19 shows HRF-reactive IgE binding to both monomeric and dimeric forms of HRF. The absorbance at 450 nm was measured after development of the color. Data indicate mean±SEM.

Monomeric and dimeric HRF-His$_6$ proteins purified by HPLC were coated onto plastic wells. After blocking, 206 (HRF-nonreactive) and IGELa2 (HRFreactive) IgEs were incubated. Bound IgEs were detected by incubation with biotin-conjugated anti-mouse IgE antibody, followed by incubation with horseradish peroxidase-conjugated streptavidin. The absorbance at 450 nm was measured after development of the color. This ELISA using purified mHRF monomers or dimers as a capturing agent showed that both monomeric and dimeric forms of mHRF can bind to IgE (FIG. 19). The dimerizing ability of HRF with multiple Ig-binding sites strongly indicates the potential of HRF to crosslink Ig-bound Fc receptors.

Figure 20:
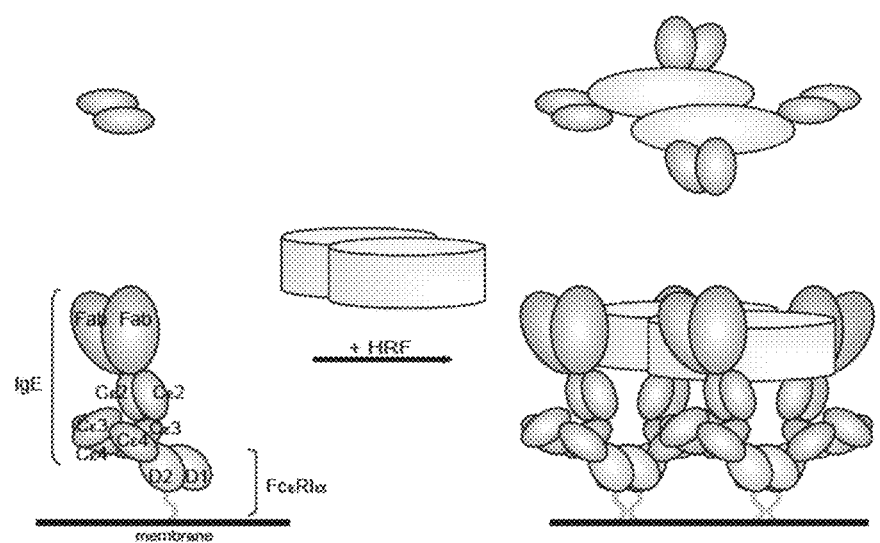
FIG. 20 shows the scheme of HRF-mediated IgE/FcεRI crosslinking. The top view (Top) of IgE at the level of Fab and the side view (Bottom) of IgE and IgE-bound FcεRIα chain are shown on the left. Formed FcεRIα chain-nucleated complexes with HRF are shown on the right. The cytoplasmic portion of FcεRIα as well as β and γ chains of FcεRI are omitted for clarity.

HRF functions as an Ig-interacting pro-inflammatory factor with properties similar to B cell superantigens that can activate mast cells and basophils through antibodies bound to their membrane-bound Fc receptors (Patella et al., J. Immunol. 145:3054 (1990); Patella et al., J. Immunol. 164: 589 (2000); Patella et al., Int. Arch. Allergy Immunol. 118:197 (1999)). Consistent with the notion that HRF could be a B cell superantigen (Silverman and Goodyear, Nat. Rev. Immunol. 6:465 (2006)), HRF binds to a substantial proportion of Igs (this study) and HRF can promote B cell proliferation (Kang et al., J. Immunol. 166:6545 (2001)). We propose that similar to B cell superantigens, which activate target cells by oligomerization of antigen receptors, interaction of dimeric HRF with Fc receptor-bound Igs on mast cells and other immune cells will lead to their activation (FIG. 20).

What is claimed:

1. A method of treating an allergic reaction, hypersensitivity, an inflammatory response or inflammation in a subject, comprising administering to the subject a peptide inhibitor of histamine releasing factor (HRF)/translationally controlled tumor protein (TCTP) receptor interaction, said peptide inhibitor consisting of amino acids 1-19 or amino acids 79-142 of SEQ ID NO:3 thereby treating the allergic reaction, hypersensitivity, inflammatory response or inflammation.

2. The method of claim 1, wherein the peptide inhibitor binds to an immunoglobulin.

3. The method of claim 1, wherein the peptide inhibitor consists of MIIYRDLISHDEMFSDIYK (SEQ ID NO:1) or QETSFTKEAYKKYIKDYMKSIKGKLEEQRPERVKPF-MTGAAEQIKHILANFKNYQ FFIGENMNP (SEQ ID NO:2) sequence.

4. The method of claim 1, wherein the treatment is sufficient to decrease, reduce, inhibit, suppress, limit, control or improve the probability, severity, frequency, or duration of one or more adverse symptoms, disorders, illnesses, pathologies, diseases, or complications caused by or associated with food allergy, allergic reaction, hypersensitivity, inflammatory response or inflammation.

5. The method of claim 1, wherein the method reduces or inhibits progression, severity frequency, duration or probability of an adverse symptom of food allergy, allergic reaction, hypersensitivity, inflammatory response or inflammation.

6. The method of claim 5, wherein the adverse symptom comprises shortness of breath (dyspnea), wheezing, stridor, coughing, airway remodeling, rapid breathing (tachypnea), prolonged expiration, runny nose, rapid or increased heart rate (tachycardia), rhonchous lung, over-inflation of the chest or chest-tightness, decreased lung capacity, an acute asthmatic episode, lung, airway or respiratory mucosum inflammation, or lung, airway or respiratory mucosum tissue damage.

7. The method of claim 1, wherein the allergic reaction is selected from: Extrinsic or intrinsic bronchial asthma; Allergic rhinitis; Onchocercal dermatitis; Atopic dermatitis; eczema; rash; allergic urticaria (e.g. hives); allergic conjunctivitis; Drug reactions; Nodules, eosinophilia, rheumatism, dermatitis, and swelling (NERDS); esophageal and a gastrointestinal allergy.

8. The method of claim 1, wherein the hypersensitivity, inflammatory response or inflammation comprises a respiratory disease or disorder.

9. The method of claim 8, wherein the respiratory disease or disorder comprises asthma, allergic asthma, bronchiolitis or pleuritis.

10. The method of claim 8, wherein the respiratory disease or disorder is selected from: Airway Obstruction, Apnea, Asbestosis, Atelectasis, Berylliosis, Bronchiectasis, Bronchiolitis, Bronchiolitis Obliterans Organizing Pneumonia, Bronchitis, Bronchopulmonary Dysplasia, Empyema, Pleural Empyema, Pleural Epiglottitis, Hemoptysis, Hypertension, Kartagener Syndrome, Meconium Aspiration, Pleural Effusion, Pleurisy, Pneumonia, Pneumothorax, Respiratory Distress Syndrome, Respiratory Hypersensitivity, Rhinoscleroma, Scimitar Syndrome, Severe Acute Respiratory Syndrome, Silicosis, Tracheal Stenosis, eosinophilic pleural effusions, Histiocytosis; chronic eosinophilic pneumonia; hypersensitivity pneumonitis; Allergic bronchopulmonary aspergillosis; Sarcoidosis; Idiopathic pulmonary fibrosis; pulmonary edema; pulmonary embolism; pulmonary emphysema; Pulmonary Hyperventilation; Pulmonary Alveolar Proteinosis; Chronic Obstructive Pulmonary Disease (COPD); Interstitial Lung Disease; allergic rhinoconjunctivitis; allergic conjunctivitis and Topical eosinophilia.

* * * * *